US007332582B2

(12) United States Patent
Hardy et al.

(10) Patent No.: US 7,332,582 B2
(45) Date of Patent: Feb. 19, 2008

(54) HUMANIZED IMMUNOMODULATORY MONOCLONAL ANTIBODIES FOR THE TREATMENT OF NEOPLASTIC DISEASE OR IMMUNODEFICIENCY

(75) Inventors: Britta Hardy, Tel Aviv (IL); Steven Tarran Jones, Radlett (GB); Leah Klapper, Givataim (IL)

(73) Assignees: CureTech Ltd., Yavne (IL); Mor-Research Applications Ltd., Petach Tikva (IL)

( * ) Notice: Subject to any disclaimer, the term of this patent is extended or adjusted under 35 U.S.C. 154(b) by 0 days.

(21) Appl. No.: 10/994,091

(22) Filed: Nov. 19, 2004

(65) Prior Publication Data

US 2005/0180969 A1 Aug. 18, 2005

Related U.S. Application Data

(63) Continuation of application No. PCT/IL03/00425, filed on May 22, 2003.

(30) Foreign Application Priority Data

May 23, 2002 (IL) ...................................... 149820

(51) Int. Cl.
*C12P 21/08* (2006.01)
*C12P 21/04* (2006.01)
*C07K 16/00* (2006.01)
*A61K 39/395* (2006.01)
*C12N 5/06* (2006.01)
*C07H 21/04* (2006.01)
*G01N 33/574* (2006.01)

(52) U.S. Cl. ................... 530/387.3; 530/388.1; 530/388.75; 530/388.8; 424/133.1; 424/141.1; 424/154.1; 424/155.1; 435/69.6; 435/328; 435/343.2

(58) Field of Classification Search ............. 530/387.3, 530/388.8; 424/133.1
See application file for complete search history.

(56) References Cited

U.S. PATENT DOCUMENTS

| 5,225,539 | A | | 7/1993 | Winter |
| 5,530,101 | A | * | 6/1996 | Queen et al. |
| 5,585,089 | A | | 12/1996 | Queen et al. |
| 5,618,920 | A | * | 4/1997 | Robinson et al. |
| 5,658,741 | A | | 8/1997 | Bolton et al. |
| 5,897,862 | A | | 4/1999 | Hardy et al. |
| 6,074,635 | A | | 6/2000 | Abrignani |
| 6,294,654 | B1 | | 9/2001 | Bogen et al. |

FOREIGN PATENT DOCUMENTS

| WO | WO 91/09967 | 7/1991 |
| WO | WO 00/58363 | 10/2000 |
| WO | WO 03/033644 A2 | 4/2003 |

OTHER PUBLICATIONS

William E. Paul. Fundamental Immunology, 3rd Edition, pp. 292-295, 1993.*
Rudikoff et al. Proc. Natl. Acad. Sci. USA, 79(6):1979-1983, Mar. 15, 1982.*
Bendig M. M. Methods: A Companion to Methods in Enzymology, 8:83-93, 1995.*
Jefferson Foote et al., "Antibody Framework Residues Affecting the Conformation of the Hypervariable Loops", J. Mol. Biol, vol. 224, pp. 487-499 (1992).
C. A. Kettleborough et al., "Optimization Of Primers For Cloning Libraries Of Mouse Immunoglobulin Genes Using The Polymerase Chain Reaction", Eur. J. Immunol. vol. 23, pp. 206-211 (1993).
R. E. Bruccoleri et al., "Prediction of the Folding of Short Polypeptide Segments by Uniform Conformational Sampling", Biopolymers, vol. 26, pp. 137-168 (1987).
Cyrus Chothia et al., "Canonical Structures for the Hypervariable Regions of Immunoglobulins" J. Mol. Biol, Biopolymers, vol. 196, pp. 901-914 (1987).
A. C. R. Martin et al. "Structure Families in Loops of Homologous Proteins: Automatic Classification, Modelling and Application to Antibodies", J. Mol. Biol., vol. 263, pp. 800-815 (1996).
Anna Tramontano et al., "Framework Residue 71 is a Major Determinant of the Position and Conformation of the Second Hypervariable Region in the $V_H$ Domains of Immunoglobulins", J. Mol. Biol., vol. 215, pp. 175-185 (1990).
Britta Hardy et al., "A Lymphocyte-Activating Monoclonal Antibody Induces Regression Of Human Tumors In Severe Combined Immunodeficient Mice", Prod. Natl. Acad. Sci., vol. 94, pp. 5756-5760 (1997).
James D. Marks et al., "By-passing Immunization Human Antibodies from V-gene Libraries Displayed on Phage", , J. Mol. Biol., vol. 222, pp. 581-597 (1991).
Cyrus Chothia et al., "Structural Repertoire of the Human VH Segments", J. Mol. Biol., vol. 227, pp. 799-817 (1992).
Qiang Fang et al., "Human Rheumatoid Factors with Restrictive Specificity for Rabbit Immunoglobulin G: Auto-and Multi-reactivity, Diverse $V_H$ Gene Segment Usage and Preferential Usage of $V_\lambda IIIb$", The Journal of Experimental Medicine, vol. 179, pp. 1445-1456 (1994).
Willem P.C. Stemmer et al;. "Single-Step Assembly Of A Gene And Entire Plasmid From Large Numbers Of Oligodeoxyribonucleotides", Gene, vol. 164, pp. 49-53 (1995).
Cyrus Chothia et al., "Conformations Of Immunoglobulin Hypervariable Regions", Nature, vol. 342, pp. 877-883 (1989).
Britta Hardy et al., "Treatment With BAT Monoclonal Antibody Decreases Tumor Burden In A Murine Model Of Leukemia/ Lymphoma", International Journal Of Oncology vol. 19, pp. 897-902 (2001).
Britta Hardy et al., "A Monoclonal antibody to Human B Lymphoblastoid Cells Activates Human and Murine T Lymphocytes", Cellular Immunology, vol. 118, pp. 22-29 (1989).

(Continued)

(74) *Attorney, Agent, or Firm*—Winston & Strawn LLP

*Primary Examiner*—David J. Blanchard

(57) ABSTRACT

The present invention provides to a humanized monoclonal antibody having immunostimulatory effects. This antibody binds specifically to B lymphoblastoid cells, induces proliferation and activation of peripheral blood lymphocytes, and is capable of eliciting an anti-tumor effect upon administration to subjects suffering from cancer.

12 Claims, 31 Drawing Sheets

OTHER PUBLICATIONS

Paul Carter et al., "High Level *Escherichia coli* Expression Mid Production Of A Bivalent Humanized Antibody Fragment", Research, Bio/Technology, vol. 10, (1992).

B. Hardy et al., XP-000915668, "Immune Stimulatory And Anti-Tumor Properties Of Anti-CD3 And BAT Monoclonal Antibodies: A Comparative Study". Human Antibodies, vol. 8, No. 2, pp. 95-98 (1997;).

B. Hardy et al., XP-000910216, "A Monoclonal Antibody Against A Human B Lymphoblastoid Cell Line Induces Tumor Regression In Mice", Cancer Research, vol. 54, No. 22, pp. 5793-5796 (1994).

* cited by examiner

```
ATGGATTTACAGGTGCAGATTATCAGCTTCCTGCTAATCAGTGCCTCAGTCATAATGTCC
1 - - - -+ - - - -+ - - - -+ - - - -+ - - - -+ - - - - 60
TACCTAAATGTCCACGTCTAATAGTCGAAGGACGATTAGTCACGGAGTCAGTATTACAGG
  M  D  L  Q  V  Q  I  I  S  F  L  L  I  S  A  S  V  I  M  S

AGAGGACAAATTGTTCTCACCCAGTCTCCAGCAATCATGTCTGCATCTCCAGGGGAGAAG
61 - - - + - - - -+- - - - -+ - - - - + - - - - + - - - 120
TCTCCTGTTTAACAAGAGTGGGTCAGAGGTCGTTAGTACAGACGTAGAGGTCCCCTCTTC
  R  G  Q  I  V  L  T  Q  S  P  A  I  M  S  A  S  P  G  E  K

GTCACCATAACCTGCAGTGCCAGGTCAAGTGTAAGTTACATGCACTGGTTCCAGCAGAAG
121 - -- -+ - - - -+- - - - -+ - - - -+ - - - -+ - - - -180
CAGTGGTATTGGACGTCACGGTCCAGTTCACATTCAATGTACGTGACCAAGGTCGTCTTC
  V  T  I  T  C  S  A  R  S  S  V  S  Y  M  H  W  F  Q  Q  K

CCAGGCACTTCTCCCAAACTCTGGATTTATAGGACATCCAACCTGGCTTCTGGAGTCCCT
181 - - --+ - - - -+ - - - -+ - -- - -+ - - - - + - - - 240
GGTCCGTGAAGAGGGTTTGAGACCTAAATATCCTGTAGGTTGGACCGAAGACCTCAGGGA
  P  G  T  S  P  K  L  W  I  Y  R  T  S  N  L  A  S  G  V  P

GCTCGCTTCAGTGGCAGTGGATCTGGGACCTCTTACTGTCTCACAATCAGCCGAATGGAG
241 - - -+ - - -- -+- - - - -+- - -- - -+ - - - -+ - - - 300
CGAGCGAAGTCACCGTCACCTAGACCCTGGAGAATGACAGAGTGTTAGTCGGCTTACCTC
  A  R  F  S  G  S  G  S  G  T  S  Y  C  L  T  I  S  R  M  E

GCTGAAGATGCTGCCACTTATTACTGCCAGCAAAGGAGTAGTTTCCCACTCACGTTCGGC
301 - - -+ - - -- -+- - - - -+ - - - -+ - - - -+ - - - 360
CGACTTCTACGACGGTGAATAATGACGGTCGTTTCCTCATCAAAGGGTGAGTGCAAGCCG
  A  E  D  A  A  T  Y  Y  C  Q  Q  R  S  S  F  P  L  T  F  G

TCGGGGACAAAGTTGGAAATAAAA
361 - - -+ - - - -+ - 384
AGCCCCTGTTTCAACCTTTATTTT
  S  G  T  K  L  E  I  K
```

FIGURE 1

Chothia Canonical Classes

L1 (10 amino acids) = Class 1 *
        Key Residues: 2(I); 25(A); 29(VIL); 33(LM); 71(YF)

L2 (7 amino acids) = Class 1
        Key Residues: 48(IV); 51(AT); 52(ST); 64(G)

L3 (9 amino acids) = Class 1
        Key Residues: 90(QNH); 95 (P)

Martin Canonical Classes

L1 (10 amino acids) = Class undefined (though most similar to Class 1/10A*)
        Key Residues: 2(I); 4(L); 23(C); 25(A); 30(V); 33(LM); 35(W); 71(Y); 88(C); 90(Q); 93(SYR)

L2 (7 amino acids) = Class 1/7A
        Key Residues: 23(C)

L3 (9 amino acids) = Class undefined (though most similar to Class 1/9A)
        Key Residues: 2(ILV); 3(VQLE); 4(ML); 28(SNDTE) ✣; 30(DLYVISNFHGT); 31(SNTKG); 32(FYNAHSR); 33(MLVIF); 88(C); 89(QSGFL); 90(QNH); 91(NFGSRDHTYV); 92(NYWTSRQHAD); 93(ENGHTSRAQHAD); 94(DYTVLHNIWPS)✧; 95(P); 96(PLYRIWF); 97(T); 98(F)

* This class is seen only in Kabat mouse kappa subgroup VI.

✣ Since the L1 loop is only 10 amino acids long, there is no residue at this position in the BAT $V_K$ region.

✧ The amino acid Phe (F) is found at this position in the BAT $V_K$ region.

FIGURE 2

```
    ATGGCTTGGGTGTGGACCTTGCTATTCCTGATGGCAGCTGCCCAAAGTATCCAAGCACAG
1   - - - - +- - - - +- - - - -+- - - - -+- - - - -+ - - -  60
    TACCGAACCCACACCTGGAACGATAAGGACTACCGTCGACGGGTTTCATAGGTTCGTGTC
     M   A   W   V   W   T   L   L   F   L   M   A   A   A   Q   S   I   Q   A   Q

ATCCAGTTGGTGCAGTCTGGACCTGAGTTGAAGAAGCCTGGAGAGACAGTCAAGATCTCC
61  - - -  + - - - - +- - - - -+- - - - -+- - - - -+ - - -120
    TAGGTCAACCACGTCAGACCTGGACTCAACTTCTTCGGACCTCTCTGTCAGTTCTAGAGG
     I   Q   L   V   Q   S   G   P   E   L   K   K   P   G   E   T   V   K   I   S

TGCAAGGCTTCTGGATATACTTTCACAAACTATGGAATGAACTGGGTGAAGCAGGCTCCA
121 - - - - + - - - - +- - - - -+- - - - -+- - - - -+ - - -180
    ACGTTCCGAAGACCTATATGAAAGTGTTTGATACCTTACTTGACCCACTTCGTCCGAGGT
     C   K   A   S   G   Y   T   F   T   N   Y   G   M   N   W   V   K   Q   A   P

GGAAAGGGTTTAAAGTGGATGGGCTGGATAAACACCGACAGTGGAGAGTCAACATATGCT
181 - - - - + - - - - +- - - - -+- - - - -+- - - - -+ - - - 240
    CCTTTCCCAAATTTCACCTACCCGACCTATTTGTGGCTGTCACCTCTCAGTTGTATACGA
     G   K   G   L   K   W   M   G   W   I   N   T   D   S   G   E   S   T   Y   A

GAAGAGTTCAAGGGACGGTTTGCCTTCTCTTTGGAAACCTCTGCCAACACTGCCTATTTG
241 - - - - + - - - - +- - - - -+- - - - -+- - - - -+ - - - 300
    CTTCTCAAGTTCCCTGCCAAACGGAAGAGAAACCTTTGGAGACGGTTGTGACGGATAAAC
     E   E   F   K   G   R   F   A   F   S   L   E   T   S   A   N   T   A   Y   L

CAGATCAACAACCTCAACAATGAGGACACGGCTACATATTTCTGTGTGAGAGTCGGCTAC
301 - - - - + - - - - +- - - - -+- - - - -+- - - - -+ - - -360
    GTCTAGTTGTTGGAGTTGTTACTCCTGTGCCGATGTATAAAGACACACTCTCAGCCGATG
     Q   I   N   N   L   N   N   E   D   T   A   T   Y   F   C   V   R   V   G   Y

GATGCTTTGGACTACTGGGGTCAAGGAACCTCAGTCACCGTCTCCTCA
361 - - - - + - - - - +- - - - -+- - - - -+ - - - 408
    CTACGAAACCTGATGACCCCAGTTCCTTGGAGTCAGTGGCAGAGGAGT
     D   A   L   D   Y   W   G   Q   G   T   S   V   T   V   S   S
```

FIGURE 3

Chothia Canonical Classes

H1 (10 amino acids*) = Class 1
                       Key Residues:  24(T<u>A</u>VGS); 26(<u>G</u>);
                                      27;(F<u>Y</u>TG); 29(<u>F</u>LIV);
                                      34(<u>M</u>IVLT); 94(<u>R</u>TKHGL)

H2 (17 amino acids) = Class 2
                        Key Residues:  52a(P<u>T</u>A); 55(<u>G</u>S); 71(A<u>L</u>T)

Martin Canonical Classes

H1 (10 amino acids*) = Class 1/10A
                       Key Residues:  2(V<u>I</u>G); 4(<u>L</u>V); 20(L<u>I</u>MV);
                                    22(<u>C</u>); 24(T<u>A</u>VGS); 26(<u>G</u>);
                                    29(I<u>F</u>LS); 32(IH<u>Y</u>FTNCED);
                                    33(YAW<u>G</u>TLV); 34(IV<u>M</u>W);
                                    35(HE<u>N</u>QSYT); 36(<u>W</u>);
                                    48(I<u>M</u>LV); 51(L<u>I</u>VTSN);
                                    69(IL<u>F</u>MV); 78(<u>A</u>LVYF);
                                    80(<u>L</u>M); 90(<u>Y</u>F); 92(<u>C</u>);
                                    94(<u>R</u>KGSHN); 102(<u>Y</u>HVISDG)

H2 (10 amino acids✱) = Class undefined (though most similar to Class
                                              2/10A)
                        Key Residues:  33(YW<u>G</u>ATL); 47(<u>W</u>Y);
                                    50(RE<u>W</u>YGQVLNKA); 51(L<u>I</u>);
                                    52(DL<u>N</u>SY); 53(AGYSKTN)✧;
                                    54(N<u>S</u>TKDG); 56(YR<u>E</u>DGVSA);
                                    58(KN<u>T</u>SDRGFY); 59(<u>Y</u>);
                                    69(I<u>F</u>LM); 71(VA<u>L</u>); 78(<u>A</u>LV)

\* The H1 loop actually consists of 5 amino acids of CDR1 and 5 amino acids of the N-terminal end of FR1.

✱ AbM defines the H2 loop as only 10 amino acids long, i.e. 7 amino acids shorter than the Kabat definition for CDR2.

✧ The amino acid Asp (D) is found at this position in the BAT $V_H$ region.

FIGURE 4

| CDRs Kabat NO | SEQ ID NO | | | | | | | |
|---|---|---|---|---|---|---|---|---|
| | | | ====L1==== | | ==L2=== | | ===L3=== | |
| | | 1 | 2 | 3 | 4 | 5 | 6 | 7 |
| | | 1234567890123456789012345678901234567890123456789012345678901234567890 |
| Mouse BATVk | 129 | QIVLTQSPAIMSASPGEKVTITCSARSSVSYMHWFQQKPGTSPKLWIYRTSNLASGVPARFSGSGSGTSY |
| Haman TEL9Vk | 130 | E......SSL...V.DR.....R.SQSISN.LN.Y.....KA...L..AA.T.Q....S........D |
| Variants | | |
| BATRK$_A$ | 15 | EIVLTQSPSSLSASVGDRVTITCSARS-SVSYMHWYQQKPGKAPKLLIYRTSNLASGVPSRFSGSGSGTD |
| BATRK$_B$ | 16 | EIVLTQSPSSLSASVGDRVTITCSARS-SVSYMHWFQQKPGKAPKLWIYRTSNLASGVPSRFSGSGSGTD |
| BATRKC | 17 | EIVLTQSPSSLSASVGDRVTITCSÁRS-SVSYMHWFQQKPGKAPKLWIYRTSNLASGVPSRFSGSGSGTD |
| BATRK$_D$ | 18 | EIVLTQSPSSLSASVGDRVTITCSARS-SVSYMHWFQQKPGKAPKLWIYRTSNLASGVPSRFSGSGSGTD |

| CDRs Kabat NO | SEQ ID NO | | | |
|---|---|---|---|---|
| | | 8 | 9 | 10 |
| | | 1234567890123456789012345678901234567 |
| Mouse BATVk | 129 | CLTISRMEAEDAATYYCQQRSSFPLTFGSGTKLEIK |
| Haman TEL9Vk | 130 | FT...NSLQP..F......TN........G...... |
| Variants | | |
| BATRK$_A$ | 15 | FTLTINSLQPEDFATYYCQQRSSFPLTFGGGTKLEIK |
| BATRK$_B$ | 16 | YTLTINSLQPEDFATYYCQQRSSFPLTFGGGTKLEIK |
| BATRKC | 17 | YCLTINSLQPEDFATYYCQQRSSFPLTFGGGTKLEIK |
| BATRK$_D$ | 18 | YCLTINSLQPEDFATYYCQQRSSFPLTFGGGTKLEIK |

FIGURE 5

```
CDRs Kabat Numbers           -----=H1=      ======H2========         ====H3=====
                                                                               H3====
                        1          2         3         4          5          6         7
                   1234567890123456789012345678901234567890123456789012A345678901234567890123456
Mouse BATVH        QIQLVQSGPELKKPGETVKISCKASGYTFTNYGMNWVKQAPGKGLKWMGWINTDSGESTYAEEFKGRFAFSLETSAN
(SEQ ID NO: 145)
hsighv 1295 VH     .V.......S.......AS..........S..SSHAI...R....Q...Q......NT.SP....QG.T...V...D...VS
(SEQ ID NO: 146)
Variant SEQ ID NO.
BATRHA   20        QVQLVQSGSELKKPGASVKISCKASGYSFSNYGMNWVRQAPGQGLQWMGWINTDSGESTYAEEFKGRFVFSLDTSVS
BATRHB   21        QVQLVQSGSELKKPGASVKISCKASGYTFTNYGMNWVRQAPGQGLQWMGWINTDSGESTYAEEFKGRFVFSLDTSVS
BATRHC   22        QVQLVQSGSELKKPGASVKISCKASGYTFTNYGMNWVRQAPGQGLQWMGWINTDSGESTYAEEFKGRFVFSLDTSVN
BATRHD   23        QIQLVQSGSELKKPGASVKISCKASGYTFTNYGMNWVRQAPGQGLQWMGWINTDSGESTYAEEFKGRFVFSLDTSVN
BATRHE   24        QIQLVQSGSELKKPGASVKISCKASGYTFTNYGMNWVKQAPGQGLKWMGWINTDSGESTYAEEFKGRFAFSLDTSVN CDRs Kabat Numbers   H3=====
                            8           9          10         11
                     7890123456789ABC34567890123456789012345678901234567890123
Mouse BATVH          TAYLQINNLNNEDTATYFCVRVGYDAL---DYWGQGTSVTVSS
(SEQ ID NO: 145)
hsighv 1295 VH       ......TS.TA...GM...AKESHSSA LDL.........L.........
(SEQ ID NO: 146)
Variant SEQ ID NO.
BATRHA   20          TAYLQITSLTAEDTGMYFCAKVGYDAL---DYWGQGTLVTVSS
BATRHB   21          TAYLQITSLTAEDTGMYFCAKVGYDAL---DYWGQGTLVTVSS
BATRHC   22          TAYLQITSLTAEDTGMYFCVRVGYDAL---DYWGQGTLVTVSS
BATRHD   23          TAYLQITSLTAEDTGMYFCVRVGYDAL---DYWGQGTLVTVSS
BATRHE   24          TAYLQITSLNAEDTGMYFCVRVGYDAL---DYWGQGTLVTVSS
```

FIGURE 6

```
     AAGCTTGCCGCCACCATGGACATGAGGGTCCCCGCTCAGCTCCTGGGGCTCCTGCTGCTC
  1  ------------+---------+---------+---------+---------+---------+  60
     TTCGAACGGCGGTGGTACCTGTACTCCCAGGGGCGAGTCGAGGACCCCGAGGACGACGAG

M  D  M  R  V  P  A  Q  L  L  G  L  L  L  L

TGGCTCCCAGGTGCCAAATGTGAAATTGTGTTGACGCAGTCTCCATCCTCCCTGTCTGCA
 61  ------------+---------+---------+---------+---------+---------+  120
     ACCGAGGGTCCACGGTTTACACTTTAACACAACTGCGTCAGAGGTAGGAGGGACAGACGT

W  L  P  G  A  K  C  E  I  V  L  T  Q  S  P  S  S  L  S  A

TCTGTAGGAGACAGAGTCACCATCACTTGCAGTGCCAGGTCAAGTGTAAGTTACATGCAC
121  ------------+---------+---------+---------+---------+---------+  180
     AGACATCCTCTGTCTCAGTGGTAGTGAACGTCACGGTCCAGTTCACATTCAATGTACGTG

S  V  G  D  R  V  T  I  T  C  S  A  R  S  S  V  S  Y  M  H

TGGTATCAGCAGAAACCAGGGAAAGCCCCTAAGCTCCTGATCTATAGGACATCCAACCTG
181  ------------+---------+---------+---------+---------+---------+  240
     ACCATAGTCGTCTTTGGTCCCTTTCGGGGATTCGAGGACTAGATATCCTGTAGGTTGGAC

W  Y  Q  Q  K  P  G  K  A  P  K  L  L  I  Y  R  T  S  N  L

GCTTCTGGGGTCCCATCTAGATTCAGCGGCAGTGGATCTGGGACAGATTTCACTCTCACC
241  ------------+---------+---------+---------+---------+---------+  300
     CGAAGACCCCAGGGTAGATCTAAGTCGCCGTCACCTAGACCCTGTCTAAAGTGAGAGTGG

A  S  G  V  P  S  R  F  S  G  S  G  S  G  T  D  F  T  L  T

ATCAACAGCCTGCAGCCTGAAGATTTTGCAACTTACTATTGCCAGCAAAGGAGTAGTTTC
301  ------------+---------+---------+---------+---------+---------+  360
     TAGTTGTCGGACGTCGGACTTCTAAAACGTTGAATGATAACGGTCGTTTCCTCATCAAAG

I  N  S  L  Q  P  E  D  F  A  T  Y  Y  C  Q  Q  R  S  S  F

CCACTCACGTTCGGCGGAGGGACCAAGCTGGAGATCAAACGTGAGTGGATCC
361  ------------+---------+---------+---------+-----+--  412
     GGTGAGTGCAAGCCGCCTCCCTGGTTCGACCTCTAGTTTGCACTCACCTAGG

```
    AAGCTTGCCGCCACCATGGACATGAGGGTCCCCGCTCAGCTCCTGGGGCTCCTGCTGCTC
1   ---------+---------+---------+---------+---------+---------+ 60
    TTCGAACGGCGGTGGTACCTGTACTCCCAGGGGCGAGTCGAGGACCCCGAGGACGACGAG

M  D  M  R  V  P  A  Q  L  L  G  L  L  L  L

TGGCTCCCAGGTGCCAAATGTGAAATTGTGTTGACGCAGTCTCCATCCTCCCTGTCTGCA
61  ---------+---------+---------+---------+---------+---------+ 120
    ACCGAGGGTCCACGGTTTACACTTTAACACAACTGCGTCAGAGGTAGGAGGGACAGACGT

W  L  P  G  A  K  C  E  I  V  L  T  Q  S  P  S  S  L  S  A

TCTGTAGGAGACAGAGTCACCATCACTTGCAGTGCCAGGTCAAGTGTAAGTTACATGCAC
121 ---------+---------+---------+---------+---------+---------+ 180
    AGACATCCTCTGTCTCAGTGGTAGTGAACGTCACGGTCCAGTTCACATTCAATGTACGTG

S  V  G  D  R  V  T  I  T  C  S  A  R  S  S  V  S  Y  M  H

TGGTTCCAGCAGAAACCAGGGAAAGCCCCTAAGCTCTGGATCTATAGGACATCCAACCTG
181 ---------+---------+---------+---------+---------+---------+ 240
    ACCAAGGTCGTCTTTGGTCCCTTTCGGGGATTCGAGACCTAGATATCCTGTAGGTTGGAC

W  F  Q  Q  K  P  G  K  A  P  K  L  W  I  Y  R  T  S  N  L

GCTTCTGGGGTCCCATCTAGATTCAGCGGCAGTGGATCTGGGACAGATTACACTCTCACC
241 ---------+---------+---------+---------+---------+---------+ 300
    CGAAGACCCCAGGGTAGATCTAAGTCGCCGTCACCTAGACCCTGTCTAATGTGAGAGTGG

A  S  G  V  P  S  R  F  S  G  S  G  S  G  T  D  Y  T  L  T

ATCAACAGCCTGCAGCCTGAAGATTTTGCAACTTACTATTGCCAGCAAAGGAGTAGTTTC
301 ---------+---------+---------+---------+---------+---------+ 360
    TAGTTGTCGGACGTCGGACTTCTAAAACGTTGAATGATAACGGTCGTTTCCTCATCAAAG

I  N  S  L  Q  P  E  D  F  A  T  Y  Y  C  Q  Q  R  S  S  F

CCACTCACGTTCGGCGGAGGGACCAAGCTGGAGATCAAACGTGAGTGGATCC
361 ---------+---------+---------+---------+---------+-- 412
    GGTGAGTGCAAGCCGCCTCCCTGGTTCGACCTCTAGTTTGCACTCACCTAGG

```
     AAGCTTGCCGCCACCATGGACATGAGGGTCCCCGCTCAGCTCCTGGGGCTCCTGCTGCTC
  1  ------------+---------+---------+---------+---------+---------+  60
     TTCGAACGGCGGTGGTACCTGTACTCCCAGGGGCGAGTCGAGGACCCCGAGGACGACGAG
                M  D  M  R  V  P  A  Q  L  L  G  L  L  L  L

TGGCTCCCAGGTGCCAAATGTGAAATTGTGTTGACGCAGTCTCCATCCTCCCTGTCTGCA
 61  ------------+---------+---------+---------+---------+---------+  120
     ACCGAGGGTCCACGGTTTACACTTTAACACAACTGCGTCAGAGGTAGGAGGGACAGACGT
        W  L  P  G  A  K  C  E  I  V  L  T  Q  S  P  S  S  L  S  A

TCTGTAGGAGACAGAGTCACCATCACTTGCAGTGCCAGGTCAAGTGTAAGTTACATGCAC
121  ------------+---------+---------+---------+---------+---------+  180
     AGACATCCTCTGTCTCAGTGGTAGTGAACGTCACGGTCCAGTTCACATTCAATGTACGTG
        S  V  G  D  R  V  T  I  T  C  S  A  R  S  S  V  S  Y  M  H

TGGTTCCAGCAGAAACCAGGGAAAGCCCCTAAGCTCTGGATCTATAGGACATCCAACCTG
181  ------------+---------+---------+---------+---------+---------+  240
     ACCAAGGTCGTCTTTGGTCCCTTTCGGGGATTCGAGACCTAGATATCCTGTAGGTTGGAC
        W  F  Q  Q  K  P  G  K  A  P  K  L  W  I  Y  R  T  S  N  L

GCTTCTGGGGTCCCATCTAGATTCAGCGGCAGTGGATCTGGGACATCTTACTGTCTCACC
241  ------------+---------+---------+---------+---------+---------+  300
     CGAAGACCCCAGGGTAGATCTAAGTCGCCGTCACCTAGACCCTGTAGAATGACAGAGTGG
        A  S  G  V  P  S  R  F  S  G  S  G  S  G  T  S  Y  C  L  T

ATCAACAGCCTGCAGCCTGAAGATTTTGCAACTTACTATTGCCAGCAAAGGAGTAGTTTC
301  ------------+---------+---------+---------+---------+---------+  360
     TAGTTGTCGGACGTCGGACTTCTAAAACGTTGAATGATAACGGTCGTTTCCTCATCAAAG
        I  N  S  L  Q  P  E  D  F  A  T  Y  Y  C  Q  Q  R  S  S  F

CCACTCACGTTCGGCGGAGGGACCAAGCTGGAGATCAAACGTGAGTGGATCC
361  ------------+---------+---------+---------+-----  412
     GGTGAGTGCAAGCCGCCTCCCTGGTTCGACCTCTAGTTTGCACTCACCTAGG
        P  L  T  F  G  G  G  T  K  L  E  I  K
```

FIGURE 9

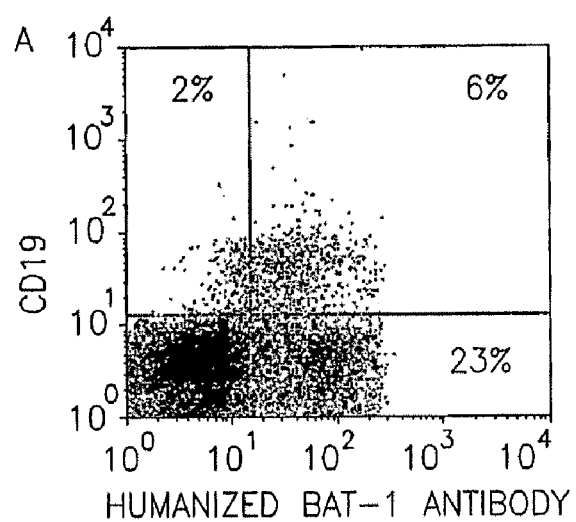
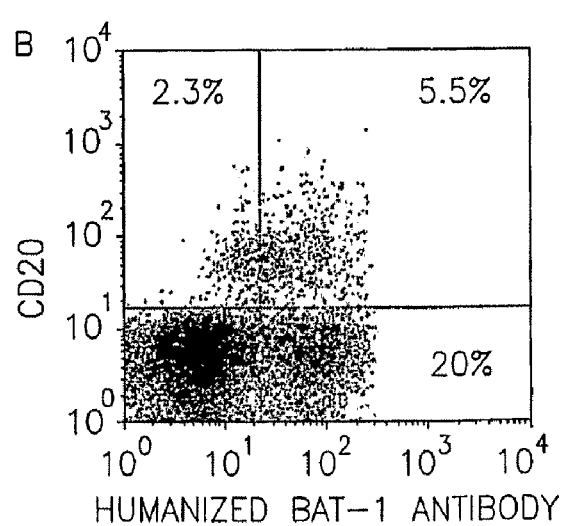
FIGURE 26

A
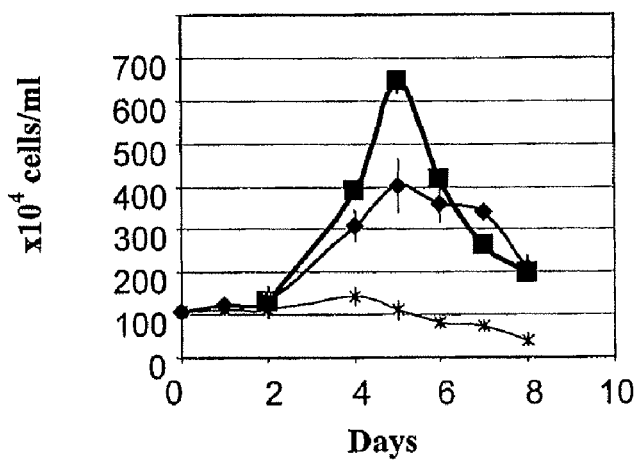
B
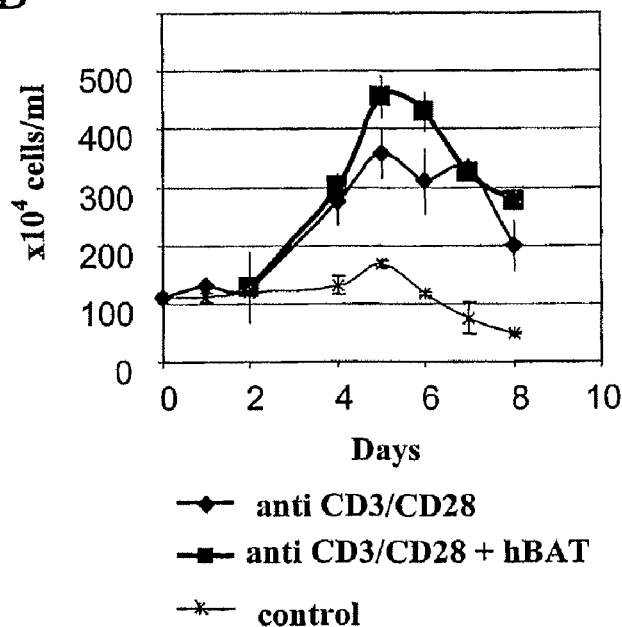
→ anti CD3/CD28
■ anti CD3/CD28 + hBAT
* control
FIGURE 31

SEQUENCE LISTING

```
<160> NUMBER OF SEQ ID NOS: 93

<210> SEQ ID NO 1
<211> LENGTH: 23
<212> TYPE: PRT
<213> ORGANISM: Artificial sequence
<220> FEATURE:
<223> OTHER INFORMATION: Synthetic peptide

<400> SEQUENCE: 1

Glu Ile Val Leu Thr Gln Ser Pro Ser Ser Leu Ser Ala Ser Val Gly
1               5                   10                  15

Asp Arg Val Thr Ile Thr Cys
            20

<210> SEQ ID NO 2
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa = Phe or Tyr
<220> FEATURE:
<221> NAME/KEY: MISC_FEATURE
```

```
<222> LOCATION: (13)..(13)
<223> OTHER INFORMATION: Xaa = Trp or Leu

<400> SEQUENCE: 2

Trp Xaa Gln Gln Lys Pro Gly Lys Ala Pro Lys Leu Xaa Ile Tyr
1               5                   10                  15

<210> SEQ ID NO 3
<211> LENGTH: 32
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (14)..(14)
<223> OTHER INFORMATION: Xaa = Asp or Ser
<220> FEATURE:
<221> NAME/KEY: MISC_FEATURE
<222> LOCATION: (15)..(15)
<223> OTHER INFORMATION: Xaa = Tyr or Phe
<220> FEATURE:
<221> NAME/KEY: MISC_FEATURE
<222> LOCATION: (16)..(16)
<223> OTHER INFORMATION: Xaa = Cys or Thr

<400> SEQUENCE: 3

Gly Val Pro Ser Arg Phe Ser Gly Ser Gly Ser Gly Thr Xaa Xaa Xaa
1               5                   10                  15

Leu Thr Ile Asn Ser Leu Gln Pro Glu Asp Phe Ala Thr Tyr Tyr Cys
                20                  25                  30

<210> SEQ ID NO 4
<211> LENGTH: 10
<212> TYPE: PRT
<213> ORGANISM: Artificial sequence
<220> FEATURE:
<223> OTHER INFORMATION: Synthetic peptide

<400> SEQUENCE: 4

Phe Gly Gly Gly Thr Lys Leu Glu Ile Lys
1               5                   10

<210> SEQ ID NO 5
<211> LENGTH: 30
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa = Ile or Val
<220> FEATURE:
<221> NAME/KEY: MISC_FEATURE
<222> LOCATION: (28)..(28)
<223> OTHER INFORMATION: Xaa = Thr or ser
<220> FEATURE:
<221> NAME/KEY: MISC_FEATURE
<222> LOCATION: (30)..(30)
<223> OTHER INFORMATION: Xaa = Thr or Ser

<400> SEQUENCE: 5

Gln Xaa Gln Leu Val Gln Ser Gly Ser Glu Leu Lys Lys Pro Gly Ala
1               5                   10                  15

Ser Val Lys Ile Ser Cys Lys Ala Ser Gly Tyr Xaa Phe Xaa
                20                  25                  30

<210> SEQ ID NO 6
```

```
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa = Arg or Lys
<220> FEATURE:
<221> NAME/KEY: MISC_FEATURE
<222> LOCATION: (11)..(11)
<223> OTHER INFORMATION: Xaa = Gln or Lys

<400> SEQUENCE: 6

Trp Val Xaa Gln Ala Pro Gly Gln Gly Leu Xaa Trp Met Gly
1               5                   10

<210> SEQ ID NO 7
<211> LENGTH: 32
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa = Val or Ala
<220> FEATURE:
<221> NAME/KEY: MISC_FEATURE
<222> LOCATION: (11)..(11)
<223> OTHER INFORMATION: Xaa = Asn or Ser
<220> FEATURE:
<221> NAME/KEY: MISC_FEATURE
<222> LOCATION: (21)..(21)
<223> OTHER INFORMATION: Xaa = Thr or Asn
<220> FEATURE:
<221> NAME/KEY: MISC_FEATURE
<222> LOCATION: (31)..(31)
<223> OTHER INFORMATION: Xaa = Val or Ala
<220> FEATURE:
<221> NAME/KEY: MISC_FEATURE
<222> LOCATION: (32)..(32)
<223> OTHER INFORMATION: Xaa = Arg or Lys

<400> SEQUENCE: 7

Arg Phe Xaa Phe Ser Leu Asp Thr Ser Val Xaa Thr Ala Tyr Leu Gln
1               5                   10                  15

Ile Thr Ser Leu Xaa Ala Glu Asp Thr Gly Met Tyr Phe Cys Xaa Xaa
            20                  25                  30

<210> SEQ ID NO 8
<211> LENGTH: 11
<212> TYPE: PRT
<213> ORGANISM: Artificial sequence
<220> FEATURE:
<223> OTHER INFORMATION: Synthetic peptide

<400> SEQUENCE: 8

Trp Gly Gln Gly Thr Leu Val Thr Val Ser Ser
1               5                   10

<210> SEQ ID NO 9
<211> LENGTH: 10
<212> TYPE: PRT
<213> ORGANISM: Artificial sequence
<220> FEATURE:
<223> OTHER INFORMATION: Synthetic peptide

<400> SEQUENCE: 9

Ser Ala Arg Ser Ser Val Ser Tyr Met His
```

-continued

```
1               5                   10
```

\<210\> SEQ ID NO 10
\<211\> LENGTH: 7
\<212\> TYPE: PRT
\<213\> ORGANISM: Artificial sequence
\<220\> FEATURE:
\<223\> OTHER INFORMATION: Synthetic peptide

\<400\> SEQUENCE: 10

```
Arg Thr Ser Asn Leu Ala Ser
1               5
```

\<210\> SEQ ID NO 11
\<211\> LENGTH: 9
\<212\> TYPE: PRT
\<213\> ORGANISM: Artificial sequence
\<220\> FEATURE:
\<223\> OTHER INFORMATION: Synthetic peptide

\<400\> SEQUENCE: 11

```
Gln Gln Arg Ser Ser Phe Pro Leu Thr
1               5
```

\<210\> SEQ ID NO 12
\<211\> LENGTH: 5
\<212\> TYPE: PRT
\<213\> ORGANISM: Artificial sequence
\<220\> FEATURE:
\<223\> OTHER INFORMATION: Synthetic peptide

\<400\> SEQUENCE: 12

```
Asn Tyr Gly Met Asn
1               5
```

\<210\> SEQ ID NO 13
\<211\> LENGTH: 17
\<212\> TYPE: PRT
\<213\> ORGANISM: Artificial sequence
\<220\> FEATURE:
\<223\> OTHER INFORMATION: Synthetic peptide

\<400\> SEQUENCE: 13

```
Trp Ile Asn Thr Asp Ser Gly Glu Ser Thr Tyr Ala Glu Glu Phe Lys
1               5                   10                  15

Gly
```

\<210\> SEQ ID NO 14
\<211\> LENGTH: 8
\<212\> TYPE: PRT
\<213\> ORGANISM: Artificial sequence
\<220\> FEATURE:
\<223\> OTHER INFORMATION: Synthetic peptide

\<400\> SEQUENCE: 14

```
Val Gly Tyr Asp Ala Leu Asp Tyr
1               5
```

\<210\> SEQ ID NO 15
\<211\> LENGTH: 106
\<212\> TYPE: PRT
\<213\> ORGANISM: Artificial sequence
\<220\> FEATURE:
\<223\> OTHER INFORMATION: Synthetic peptide

\<400\> SEQUENCE: 15

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Tyr Gln Gln Lys Pro Gly Lys Ala Pro Lys Leu Leu Ile Tyr
        35                  40                  45

Arg Thr Ser Asn Leu Ala Ser Gly Val Pro Ser Arg Phe Ser Gly Ser
    50                  55                  60

Gly Ser Gly Thr Asp Phe Thr Leu Thr Ile Asn Ser Leu Gln Pro Glu
65                  70                  75                  80

Asp Phe Ala Thr Tyr Tyr Cys Gln Gln Arg Ser Ser Phe Pro Leu Thr
                85                  90                  95

Phe Gly Gly Gly Thr Lys Leu Glu Ile Lys
            100                 105

<210> SEQ ID NO 16
<211> LENGTH: 106
<212> TYPE: PRT
<213> ORGANISM: Artificial sequence
<220> FEATURE:
<223> OTHER INFORMATION: Synthetic peptide

<400> SEQUENCE: 16

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Phe Gln Gln Lys Pro Gly Lys Ala Pro Lys Leu Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Asp Tyr Thr Leu Thr Ile Asn Ser Leu Gln Pro Glu
65                  70                  75                  80

Asp Phe Ala Thr Tyr Tyr Cys Gln Gln Arg Ser Ser Phe Pro Leu Thr
                85                  90                  95

Phe Gly Gly Gly Thr Lys Leu Glu Ile Lys
            100                 105

<210> SEQ ID NO 17
<211> LENGTH: 106
<212> TYPE: PRT
<213> ORGANISM: Artificial sequence
<220> FEATURE:
<223> OTHER INFORMATION: Synthetic peptide

<400> SEQUENCE: 17

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Phe Gln Gln Lys Pro Gly Lys Ala Pro Lys Leu Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Asp Tyr Cys Leu Thr Ile Asn Ser Leu Gln Pro Glu
65                  70                  75                  80

Asp Phe Ala Thr Tyr Tyr Cys Gln Gln Arg Ser Ser Phe Pro Leu Thr
                85                  90                  95

```
Phe Gly Gly Gly Thr Lys Leu Glu Ile Lys
            100                 105

<210> SEQ ID NO 18
<211> LENGTH: 106
<212> TYPE: PRT
<213> ORGANISM: Artificial sequence
<220> FEATURE:
<223> OTHER INFORMATION: Synthetic peptide

<400> SEQUENCE: 18

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Phe Gln Gln Lys Pro Gly Lys Ala Pro Lys Leu Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Asp Tyr Cys Leu Thr Ile Asn Ser Leu Gln Pro Glu
65                  70                  75                  80

Asp Phe Ala Thr Tyr Tyr Cys Gln Gln Arg Ser Ser Phe Pro Leu Thr
                85                  90                  95

Phe Gly Gly Gly Thr Lys Leu Glu Ile Lys
            100                 105

<210> SEQ ID NO 19
<211> LENGTH: 129
<212> TYPE: PRT
<213> ORGANISM: Artificial sequence
<220> FEATURE:
<223> OTHER INFORMATION: Synthetic peptide

<400> SEQUENCE: 19

Met Asp Leu Gln Val Gln Ile Ile Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Pro Gly Glu Lys Val Thr Ile Thr Cys Ser Ala Arg
        35                  40                  45

Ser Ser Val Ser Tyr Met His Trp Phe Gln Gln Lys Pro Gly Thr Ser
    50                  55                  60

Pro Lys Leu Trp Ile Tyr Arg Thr Ser Asn Leu Ala Ser Gly Val Pro
65                  70                  75                  80

Ala Arg Phe Ser Gly Ser Gly Ser Gly Thr Ser Tyr Cys Leu Thr Ile
                85                  90                  95

Ser Arg Met Glu Ala Glu Asp Ala Ala Thr Tyr Tyr Cys Gln Gln Arg
            100                 105                 110

Ser Ser Phe Pro Pro Leu Thr Phe Gly Ser Gly Thr Lys Leu Glu Ile
        115                 120                 125

Lys

<210> SEQ ID NO 20
<211> LENGTH: 117
<212> TYPE: PRT
<213> ORGANISM: Artificial sequence
<220> FEATURE:
<223> OTHER INFORMATION: Synthetic peptide
```

-continued

```
<400> SEQUENCE: 20

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Ser Phe Ser Asn Tyr
            20                  25                  30

Gly Met Asn Trp Val Arg Gln Ala Pro Gly Gln Gly Leu Gln Trp Met
        35                  40                  45

Gly Trp Ile Asn Thr Asp Ser Gly Glu Ser Thr Tyr Ala Glu Glu Phe
    50                  55                  60

Lys Gly Arg Phe Val Phe Ser Leu Asp Thr Ser Val Ser Thr Ala Tyr
65                  70                  75                  80

Leu Gln Ile Thr Ser Leu Thr Ala Glu Asp Thr Gly Met Tyr Phe Cys
            85                  90                  95

Ala Lys Val Gly Tyr Asp Ala Leu Asp Tyr Trp Gly Gln Gly Thr Leu
            100                 105                 110

Val Thr Val Ser Ser
        115

<210> SEQ ID NO 21
<211> LENGTH: 117
<212> TYPE: PRT
<213> ORGANISM: Artificial sequence
<220> FEATURE:
<223> OTHER INFORMATION: Synthetic peptide

<400> SEQUENCE: 21

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Gln Gly Leu Gln Trp Met
        35                  40                  45

Gly Trp Ile Asn Thr Asp Ser Gly Glu Ser Thr Tyr Ala Glu Glu Phe
    50                  55                  60

Lys Gly Arg Phe Val Phe Ser Leu Asp Thr Ser Val Ser Thr Ala Tyr
65                  70                  75                  80

Leu Gln Ile Thr Ser Leu Thr Ala Glu Asp Thr Gly Met Tyr Phe Cys
            85                  90                  95

Ala Lys Val Gly Tyr Asp Ala Leu Asp Tyr Trp Gly Gln Gly Thr Leu
            100                 105                 110

Val Thr Val Ser Ser
        115

<210> SEQ ID NO 22
<211> LENGTH: 117
<212> TYPE: PRT
<213> ORGANISM: Artificial sequence
<220> FEATURE:
<223> OTHER INFORMATION: Synthetic peptide

<400> SEQUENCE: 22

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Gln Gly Leu Gln Trp Met
        35                  40                  45
```

```
Gly Trp Ile Asn Thr Asp Ser Gly Glu Ser Thr Tyr Ala Glu Glu Phe
        50                  55                  60

Lys Gly Arg Phe Val Phe Ser Leu Asp Thr Ser Val Asn Thr Ala Tyr
 65                  70                  75                  80

Leu Gln Ile Thr Ser Leu Thr Ala Glu Asp Thr Gly Met Tyr Phe Cys
                 85                  90                  95

Val Arg Val Gly Tyr Asp Ala Leu Asp Tyr Trp Gly Gln Gly Thr Leu
                100                 105                 110

Val Thr Val Ser Ser
            115

<210> SEQ ID NO 23
<211> LENGTH: 117
<212> TYPE: PRT
<213> ORGANISM: Artificial sequence
<220> FEATURE:
<223> OTHER INFORMATION: Synthetic peptide

<400> SEQUENCE: 23

Gln Ile Gln Leu Val Gln Ser Gly Ser Glu Leu Lys Lys Pro Gly Ala
 1               5                  10                  15

Ser Val Lys Ile Ser Cys Lys Ala Ser Gly Tyr Thr Phe Thr Asn Tyr
                 20                  25                  30

Gly Met Asn Trp Val Arg Gln Ala Pro Gly Gln Gly Leu Gln Trp Met
             35                  40                  45

Gly Trp Ile Asn Thr Asp Ser Gly Glu Ser Thr Tyr Ala Glu Glu Phe
        50                  55                  60

Lys Gly Arg Phe Val Phe Ser Leu Asp Thr Ser Val Asn Thr Ala Tyr
 65                  70                  75                  80

Leu Gln Ile Thr Ser Leu Thr Ala Glu Asp Thr Gly Met Tyr Phe Cys
                 85                  90                  95

Val Arg Val Gly Tyr Asp Ala Leu Asp Tyr Trp Gly Gln Gly Thr Leu
                100                 105                 110

Val Thr Val Ser Ser
            115

<210> SEQ ID NO 24
<211> LENGTH: 117
<212> TYPE: PRT
<213> ORGANISM: Artificial sequence
<220> FEATURE:
<223> OTHER INFORMATION: Synthetic peptide

<400> SEQUENCE: 24

Gln Ile Gln Leu Val Gln Ser Gly Ser Glu Leu Lys Lys Pro Gly Ala
 1               5                  10                  15

Ser Val Lys Ile Ser Cys Lys Ala Ser Gly Tyr Thr Phe Thr Asn Tyr
                 20                  25                  30

Gly Met Asn Trp Val Lys Gln Ala Pro Gly Gln Gly Leu Lys Trp Met
             35                  40                  45

Gly Trp Ile Asn Thr Asp Ser Gly Glu Ser Thr Tyr Ala Glu Glu Phe
        50                  55                  60

Lys Gly Arg Phe Ala Phe Ser Leu Asp Thr Ser Val Asn Thr Ala Tyr
 65                  70                  75                  80

Leu Gln Ile Thr Ser Leu Asn Ala Glu Asp Thr Gly Met Tyr Phe Cys
                 85                  90                  95

Val Arg Val Gly Tyr Asp Ala Leu Asp Tyr Trp Gly Gln Gly Thr Leu
                100                 105                 110
```

<210> SEQ ID NO 25
<211> LENGTH: 384
<212> TYPE: DNA
<213> ORGANISM: Artificial sequence
<220> FEATURE:
<223> OTHER INFORMATION: Synthetic polynucleotide

<400> SEQUENCE: 25

```
atggatttac aggtgcagat tatcagcttc ctgctaatca gtgcctcagt cataatgtcc    60
agaggacaaa ttgttctcac ccagtctcca gcaatcatgt ctgcatctcc aggggagaag   120
gtcaccataa cctgcagtgc caggtcaagt gtaagttaca tgcactggtt ccagcagaag   180
ccaggcactt ctcccaaact ctggatttat aggacatcca acctggcttc tggagtccct   240
gctcgcttca gtggcagtgg atctgggacc tcttactgtc tcacaatcag ccgaatggag   300
gctgaagatg ctgccactta ttactgccag caaaggagta gtttcccact cacgttcggc   360
tcggggacaa agttggaaat aaaa                                           384
```

<210> SEQ ID NO 26
<211> LENGTH: 136
<212> TYPE: PRT
<213> ORGANISM: Artificial sequence
<220> FEATURE:
<223> OTHER INFORMATION: Synthetic peptide

<400> SEQUENCE: 26

```
Met Ala Trp Val Trp Thr Leu Leu Phe Leu Met Ala Ala Ala Gln Ser
1               5                   10                  15
Ile Gln Ala Gln Ile Gln Leu Val Gln Ser Gly Pro Glu Leu Lys Lys
            20                  25                  30
Pro Gly Glu Thr Val Lys Ile Ser Cys Lys Ala Ser Gly Tyr Thr Phe
        35                  40                  45
Thr Asn Tyr Gly Met Asn Trp Val Lys Gln Ala Pro Gly Lys Gly Leu
    50                  55                  60
Lys Trp Met Gly Trp Ile Asn Thr Asp Ser Gly Glu Ser Thr Tyr Ala
65                  70                  75                  80
Glu Glu Phe Lys Gly Arg Phe Ala Phe Ser Leu Glu Thr Ser Ala Asn
                85                  90                  95
Thr Ala Tyr Leu Gln Ile Asn Asn Leu Asn Asn Glu Asp Thr Ala Thr
            100                 105                 110
Tyr Phe Cys Val Arg Val Gly Tyr Asp Ala Leu Asp Tyr Trp Gly Gln
        115                 120                 125
Gly Thr Ser Val Thr Val Ser Ser
    130                 135
```

<210> SEQ ID NO 27
<211> LENGTH: 408
<212> TYPE: DNA
<213> ORGANISM: Artificial sequence
<220> FEATURE:
<223> OTHER INFORMATION: Synthetic polynucleotide

<400> SEQUENCE: 27

```
atggcttggg tgtggacctt gctattcctg atggcagctg cccaaagtat ccaagcacag    60
atccagttgg tgcagtctgg acctgagttg aagaagcctg gagagacagt caagatctcc   120
```

-continued

```
tgcaaggctt ctggatatac tttcacaaac tatggaatga actgggtgaa gcaggctcca      180
ggaaagggtt taaagtggat gggctggata acaccgaca gtggagagtc aacatatgct       240
gaagagttca agggacggtt tgccttctct ttggaaacct ctgccaacac tgcctatttg      300
cagatcaaca acctcaacaa tgaggacacg gctacatatt tctgtgtgag agtcggctac     360
gatgctttgg actactgggg tcaaggaacc tcagtcaccg tctcctca                   408
```

<210> SEQ ID NO 28
<211> LENGTH: 107
<212> TYPE: PRT
<213> ORGANISM: Artificial sequence
<220> FEATURE:
<223> OTHER INFORMATION: Synthetic peptide

<400> SEQUENCE: 28

```
Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Thr Asn Ser Phe Pro Leu
                85                  90                  95

Thr Phe Gly Gly Gly Thr Lys Leu Glu Ile Lys
            100                 105
```

<210> SEQ ID NO 29
<211> LENGTH: 120
<212> TYPE: PRT
<213> ORGANISM: Artificial sequence
<220> FEATURE:
<223> OTHER INFORMATION: Synthetic peptide

<400> SEQUENCE: 29

```
Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Ser Phe Ser Ser His
            20                  25                  30

Ala Ile Asn Trp Val Arg Gln Ala Pro Gly Gln Gly Leu Gln Trp Met
        35                  40                  45

Gly Trp Ile Asn Thr Asn Thr Gly Ser Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Thr Ser Leu Thr Ala Glu Asp Thr Gly Met Tyr Phe Cys
                85                  90                  95

Ala Lys Glu Ser His Ser Ser Ala Leu Asp Leu Asp Tyr Trp Gly Gln
            100                 105                 110

Gly Thr Leu Val Thr Val Ser Ser
        115                 120
```

<210> SEQ ID NO 30
<211> LENGTH: 43
<212> TYPE: DNA

<213> ORGANISM: Artificial sequence
<220> FEATURE:
<223> OTHER INFORMATION: Synthetic polynucleotide

<400> SEQUENCE: 30
cccaagcttg ccgccaccat ggacatgagg gtccccgctc agc            43

<210> SEQ ID NO 31
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 31
tcctggggct cctgctgctc tggctcccag gtgccaaatg               40

<210> SEQ ID NO 32
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 32
tgaaattgtg ttgacgcagt ctccatcctc cctgtctgca               40

<210> SEQ ID NO 33
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 33
tctgtaggag acagagtcac catcacttgc agtgccaggt               40

<210> SEQ ID NO 34
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 34
caagtgtaag ttacatgcac tggtatcagc agaaaccagg               40

<210> SEQ ID NO 35
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 35
gaaagcccct aagctcctga tctataggac atccaacctg               40

<210> SEQ ID NO 36
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 36
gcttctgggg tcccatctag attcagcggc agtggatctg               40

<210> SEQ ID NO 37
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 37
ggacagattt cactctcacc atcaacagcc tgcagcctga                    40

<210> SEQ ID NO 38
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 38
agattttgca acttactatt gccagcaaag gagtagtttc                    40

<210> SEQ ID NO 39
<211> LENGTH: 55
<212> TYPE: DNA
<213> ORGANISM: Artificial sequence
<220> FEATURE:
<223> OTHER INFORMATION: Synthetic polynucleotide

<400> SEQUENCE: 39
ccactcacgt tcggcggagg gaccaagctg gagatcaaac gtgagtggat ccgcg   55

<210> SEQ ID NO 40
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 40
gagcagcagg agccccagga gctgagcggg gaccctcatg                    40

<210> SEQ ID NO 41
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 41
actgcgtcaa cacaatttca catttggcac ctgggagcca                    40

<210> SEQ ID NO 42
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 42
gtgactctgt ctcctacaga tgcagacagg gaggatggag                    40

<210> SEQ ID NO 43
<211> LENGTH: 40
<212> TYPE: DNA
<213> ORGANISM: Artificial sequence
<220> FEATURE:

<223> OTHER INFORMATION: Synthetic polynucleotide

<400> SEQUENCE: 43
gtgcatgtaa cttacacttg acctggcact gcaagtgatg                                40

<210> SEQ ID NO 44
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 44
tcaggagctt aggggctttc cctggtttct gctgatacca                                40

<210> SEQ ID NO 45
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 45
ctagatggga ccccagaagc caggttggat gtcctataga                                40

<210> SEQ ID NO 46
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 46
ggtgagagtg aaatctgtcc cagatccact gccgctgaat                                40

<210> SEQ ID NO 47
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 47
aatagtaagt tgcaaaatct tcaggctgca ggctgttgat                                40

<210> SEQ ID NO 48
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 48
cctccgccga acgtgagtgg gaaactactc ctttgctggc                                40

<210> SEQ ID NO 49
<211> LENGTH: 35
<212> TYPE: DNA
<213> ORGANISM: Artificial sequence
<220> FEATURE:
<223> OTHER INFORMATION: Synthetic polynucleotide

<400> SEQUENCE: 49
cgcggatcca ctcacgtttg atctccagct tggtc                                     35

<210> SEQ ID NO 50
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 50
caagtgtaag ttacatgcac tggttccagc agaaaccagg					40

<210> SEQ ID NO 51
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 51
gaaagcccct aagctctgga tctataggac atccaacctg					40

<210> SEQ ID NO 52
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 52
ggacagatta cactctcacc atcaacagcc tgcagcctga					40

<210> SEQ ID NO 53
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 53
tccagagctt aggggctttc cctggtttct gctggaacca					40

<210> SEQ ID NO 54
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 54
ggtgagagtg taatctgtcc cagatccact gccgctgaac					40

<210> SEQ ID NO 55
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 55
ggtgagacag taagatgtcc cagatccact gccgctgaac					40

<210> SEQ ID NO 56
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 56
ggacatctta ctgtctcacc atcaacagcc tgcagcctga                            40

<210> SEQ ID NO 57
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 57
cccaagcttg ccgccaccat ggactggacc tggaggatcc                            40

<210> SEQ ID NO 58
<211> LENGTH: 33
<212> TYPE: DNA
<213> ORGANISM: Artificial sequence
<220> FEATURE:
<223> OTHER INFORMATION: Synthetic polynucleotide

<400> SEQUENCE: 58
tcttcttggt ggcagcagca acaggtgccc act                                   33

<210> SEQ ID NO 59
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 59
cccaggtgca gctggtgcaa tctgggtctg agcttaagaa                            40

<210> SEQ ID NO 60
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 60
gcctggggcc tcagtgaaga tctcctgcaa ggcttctgga                            40

<210> SEQ ID NO 61
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 61
tatagcttca gtaactatgg aatgaactgg gtgcgacagg                            40

<210> SEQ ID NO 62
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 62
cccctggaca agggcttcag tggatgggat ggataaacac                            40

<210> SEQ ID NO 63
<211> LENGTH: 40

```
<212> TYPE: DNA
<213> ORGANISM: Artificial sequence
<220> FEATURE:
<223> OTHER INFORMATION: Synthetic polynucleotide

<400> SEQUENCE: 63
cgacagtgga gagtcaacat atgctgaaga gttcaaggga                    40

<210> SEQ ID NO 64
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 64
cggtttgtct tctccttgga cacctctgtc agcacggcat                    40

<210> SEQ ID NO 65
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 65
atctgcagat caccagcctc acggctgagg acactggcat                    40

<210> SEQ ID NO 66
<211> LENGTH: 35
<212> TYPE: DNA
<213> ORGANISM: Artificial sequence
<220> FEATURE:
<223> OTHER INFORMATION: Synthetic polynucleotide

<400> SEQUENCE: 66
gtatttctgt gcgaaagtcg gctacgatgc tttgg                         35

<210> SEQ ID NO 67
<211> LENGTH: 54
<212> TYPE: DNA
<213> ORGANISM: Artificial sequence
<220> FEATURE:
<223> OTHER INFORMATION: Synthetic polynucleotide

<400> SEQUENCE: 67
actactgggg ccagggaacc ctggtcaccg tctcctcagg tgagtggatc cgcg    54

<210> SEQ ID NO 68
<211> LENGTH: 45
<212> TYPE: DNA
<213> ORGANISM: Artificial sequence
<220> FEATURE:
<223> OTHER INFORMATION: Synthetic polynucleotide

<400> SEQUENCE: 68
tgctgccacc aagaagagga tccttccagg tggagtccat ggtgg              45

<210> SEQ ID NO 69
<211> LENGTH: 36
<212> TYPE: DNA
<213> ORGANISM: Artificial sequence
<220> FEATURE:
<223> OTHER INFORMATION: Synthetic polynucleotide

<400> SEQUENCE: 69
```
ttgcaccagc tgcacctggg agtgggcacc tgttgc        36

<210> SEQ ID NO 70
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 70
tcttcactga ggccccaggc ttcttaagct cagacccaga        40

<210> SEQ ID NO 71
<211> LENGTH: 39
<212> TYPE: DNA
<213> ORGANISM: Artificial sequence
<220> FEATURE:
<223> OTHER INFORMATION: Synthetic polynucleotide

<400> SEQUENCE: 71
ccatagttac tgaagctata ccagaagct tgcaggaga        39

<210> SEQ ID NO 72
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 72
ctgaagccct tgtccagggg cctgtcgcac ccagttcatt        40

<210> SEQ ID NO 73
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 73
atgttgactc tccactgtcg gtgtttatcc atcccatcca        40

<210> SEQ ID NO 74
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 74
tccaaggaga agacaaaccg tcccttgaac tcttcagcat        40

<210> SEQ ID NO 75
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 75
gaggctggtg atctgcagat atgccgtgct gacagaggtg        40

<210> SEQ ID NO 76
<211> LENGTH: 40
<212> TYPE: DNA
<213> ORGANISM: Artificial sequence

```
<220> FEATURE:
<223> OTHER INFORMATION: Synthetic polynucleotide

<400> SEQUENCE: 76
cgactttcgc acagaaatac atgccagtgt cctcagccgt                              40

<210> SEQ ID NO 77
<211> LENGTH: 33
<212> TYPE: DNA
<213> ORGANISM: Artificial sequence
<220> FEATURE:
<223> OTHER INFORMATION: Synthetic polynucleotide

<400> SEQUENCE: 77
ttccctggcc ccagtagtcc aaagcatcgt agc                                     33

<210> SEQ ID NO 78
<211> LENGTH: 36
<212> TYPE: DNA
<213> ORGANISM: Artificial sequence
<220> FEATURE:
<223> OTHER INFORMATION: Synthetic polynucleotide

<400> SEQUENCE: 78
cgcggatcca ctcacctgag gagacggtga ccaggg                                  36

<210> SEQ ID NO 79
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 79
tatactttca caaactatgg aatgaactgg gtgcgacagg                              40

<210> SEQ ID NO 80
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 80
ccatagtttg tgaaagtata tccagaagcc ttgcaggaga                              40

<210> SEQ ID NO 81
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 81
cggtttgtct tctccttgga cacctctgtc aacacggcat                              40

<210> SEQ ID NO 82
<211> LENGTH: 35
<212> TYPE: DNA
<213> ORGANISM: Artificial sequence
<220> FEATURE:
<223> OTHER INFORMATION: Synthetic polynucleotide

<400> SEQUENCE: 82
gtatttctgt gtgagagtcg gctacgatgc tttgg                                   35
```

<210> SEQ ID NO 83
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 83
cgactctcac acagaaatac atgccagtgt cctcagccgt          40

<210> SEQ ID NO 84
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 84
atctgcagat caccagcctc aacgctgagg acactggcat          40

<210> SEQ ID NO 85
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 85
gaggctggtg atctgcagat atgccgtgtt gacagaggtg          40

<210> SEQ ID NO 86
<211> LENGTH: 40
<212> TYPE: DNA
<213> ORGANISM: Artificial sequence
<220> FEATURE:
<223> OTHER INFORMATION: Synthetic polynucleotide

<400> SEQUENCE: 86
tatactttca caaactatgg aatgaactgg gtgaagcagg          40

<210> SEQ ID NO 87
<211> LENGTH: 412
<212> TYPE: DNA
<213> ORGANISM: Artificial sequence
<220> FEATURE:
<223> OTHER INFORMATION: Synthetic polynucleotide

<400> SEQUENCE: 87
aagcttgccg ccaccatgga catgagggtc cccgctcagc tcctggggct cctgctgctc     60
tggctcccag gtgccaaatg tgaaattgtg ttgacgcagt ctccatcctc cctgtctgca    120
tctgtaggag acagagtcac catcacttgc agtgccaggt caagtgtaag ttacatgcac    180
tggtatcagc agaaaccagg gaaagcccct aagctcctga tctataggac atccaacctg    240
gcttctgggg tcccatctag attcagcggc agtggatctg ggacagattt cactctcacc    300
atcaacagcc tgcagcctga agattttgca acttactatt gccagcaaag gagtagtttc    360
ccactcacgt tcggcggagg gaccaagctg gagatcaaac gtgagtggat cc            412

<210> SEQ ID NO 88
<211> LENGTH: 412
<212> TYPE: DNA
<213> ORGANISM: Artificial sequence
<220> FEATURE:
<223> OTHER INFORMATION: Synthetic polynucleotide

<400> SEQUENCE: 88

```
aagcttgccg ccaccatgga catgagggtc cccgctcagc tcctggggct cctgctgctc    60
tggctcccag gtgccaaatg tgaaattgtg ttgacgcagt ctccatcctc cctgtctgca   120
tctgtaggag acagagtcac catcacttgc agtgccaggt caagtgtaag ttacatgcac   180
tggttccagc agaaaccagg gaaagcccct aagctctgga tctataggac atccaacctg   240
gcttctgggg tcccatctag attcagcggc agtggatctg ggacagatta cactctcacc   300
atcaacagcc tgcagcctga agattttgca acttactatt gccagcaaag gagtagtttc   360
ccactcacgt tcggcggagg gaccaagctg gagatcaaac gtgagtggat cc            412
```

<210> SEQ ID NO 89
<211> LENGTH: 412
<212> TYPE: DNA
<213> ORGANISM: Artificial sequence
<220> FEATURE:
<223> OTHER INFORMATION: Synthetic polynucleotide

<400> SEQUENCE: 89

```
aagcttgccg ccaccatgga catgagggtc cccgctcagc tcctggggct cctgctgctc    60
tggctcccag gtgccaaatg tgaaattgtg ttgacgcagt ctccatcctc cctgtctgca   120
tctgtaggag acagagtcac catcacttgc agtgccaggt caagtgtaag ttacatgcac   180
tggttccagc agaaaccagg gaaagcccct aagctctgga tctataggac atccaacctg   240
gcttctgggg tcccatctag attcagcggc agtggatctg ggacatctta ctgtctcacc   300
atcaacagcc tgcagcctga agattttgca acttactatt gccagcaaag gagtagtttc   360
ccactcacgt tcggcggagg gaccaagctg gagatcaaac gtgagtggat cc            412
```

<210> SEQ ID NO 90
<211> LENGTH: 436
<212> TYPE: DNA
<213> ORGANISM: Artificial sequence
<220> FEATURE:
<223> OTHER INFORMATION: Synthetic polynucleotide

<400> SEQUENCE: 90

```
aagcttgccg ccaccatgga ctggacctgg aggatcctct tcttggtggc agcagcaaca    60
ggtgcccact cccaggtgca gctggtgcaa tctgggtctg agcttaagaa gcctggggcc   120
tcagtgaaga tctcctgcaa ggcttctgga tatactttca caaactatgg aatgaactgg   180
gtgcgacagg cccctggaca agggcttcag tggatgggat ggataaacac cgacagtgga   240
gagtcaacat atgctgaaga gttcaaggga cggtttgtct ctccttgga cacctctgtc    300
aacacggcat atctgcagat caccagcctc acggctgagg acactggcat gtatttctgt   360
gtgagagtcg gctacgatgc tttggactac tggggccagg aaccctggt caccgtctcc    420
tcaggtgagt ggatcc                                                    436
```

<210> SEQ ID NO 91
<211> LENGTH: 436
<212> TYPE: DNA
<213> ORGANISM: Artificial sequence
<220> FEATURE:
<223> OTHER INFORMATION: Synthetic polynucleotide

<400> SEQUENCE: 91

```
aagcttgccg ccaccatgga ctggacctgg aggatcctct tcttggtggc agcagcaaca    60
```

| | |
|---|---|
| ggtgcccact cccaggtgca gctggtgcaa tctgggtctg agcttaagaa gcctggggcc | 120 |
| tcagtgaaga tctcctgcaa ggcttctgga tatactttca caaactatgg aatgaactgg | 180 |
| gtgcgacagg cccctggaca agggcttcag tggatgggat ggataaacac cgacagtgga | 240 |
| gagtcaacat atgctgaaga gttcaaggga cggtttgtct tctccttgga cacctctgtc | 300 |
| agcacggcat atctgcagat caccagcctc acggctgagg acactggcat gtatttctgt | 360 |
| gcgaaagtcg gctacgatgc tttggactac tggggccagg aaccctggt caccgtctcc | 420 |
| tcaggtgagt ggatcc | 436 |

<210> SEQ ID NO 92
<211> LENGTH: 436
<212> TYPE: DNA
<213> ORGANISM: Artificial sequence
<220> FEATURE:
<223> OTHER INFORMATION: Synthetic polynucleotide

<400> SEQUENCE: 92

| | |
|---|---|
| aagcttgccg ccaccatgga ctggacctgg aggatcctct tcttggtggc agcagcaaca | 60 |
| ggtgcccact cccaggtgca gctggtgcaa tctgggtctg agcttaagaa gcctggggcc | 120 |
| tcagtgaaga tctcctgcaa ggcttctgga tatactttca caaactatgg aatgaactgg | 180 |
| gtgcgacagg cccctggaca agggcttcag tggatgggat ggataaacac cgacagtgga | 240 |
| gagtcaacat atgctgaaga gttcaaggga cggtttgtct tctccttgga cacctctgtc | 300 |
| agcacggcat atctgcagat caccagcctc acggctgagg acactggcat gtatttctgt | 360 |
| gcgaaagtcg gctacgatgc tttggactac tggggccagg aaccctggt caccgtctcc | 420 |
| tcaggtgagt ggatcc | 436 |

<210> SEQ ID NO 93
<211> LENGTH: 10259
<212> TYPE: DNA
<213> ORGANISM: Artificial sequence
<220> FEATURE:
<223> OTHER INFORMATION: pG1KD210.BAT-1.RHC/RkD single expression vector

<400> SEQUENCE: 93

| | |
|---|---|
| ttgaagacga aagggcctcg tgatacgcct atttttatag gttaatgtca tgataataat | 60 |
| ggtttcttag acgtcaggtg gcacttttcg gggaaatgtg cgcggaaccc ctatttgttt | 120 |
| atttttctaa atacattcaa atatgtatcc gctcatgaga caataaccct gataaatgct | 180 |
| tcaataatat tgaaaaagga agagtatgag tattcaacat ttccgtgtcg cccttattcc | 240 |
| cttttttgcg gcattttgcc ttcctgtttt tgctcaccca gaaacgctgg tgaaagtaaa | 300 |
| agatgctgaa gatcagttgg gtgcacgagt gggttacatc gaactggatc tcaacagcgg | 360 |
| taagatcctt gagagttttc gccccgaaga acgttttcca atgatgagca cttttaaagt | 420 |
| tctgctatgt ggcgcggtat tatcccgtgt tgacgccggg caagagcaac tcggtcgccg | 480 |
| catacactat tctcagaatg acttggttga gtactcacca gtcacagaaa agcatcttac | 540 |
| ggatggcatg acagtaagag aattatgcag tgctgccata accatgagtg ataacactgc | 600 |
| ggccaactta cttctgacaa cgatcggagg accgaaggag ctaaccgctt ttttgcacaa | 660 |
| catgggggat catgtaactc gccttgatcg ttgggaaccg gagctgaatg aagccatacc | 720 |
| aaacgacgag cgtgacacca cgatgcctgc agcaatggca acaacgttgc gcaaactatt | 780 |
| aactggcgaa ctacttactc tagcttcccg gcaacaatta atagactgga tggaggcgga | 840 |
| taaagttgca ggaccacttc tgcgctcggc ccttccggct ggctggttta ttgctgataa | 900 |

```
atctggagcc ggtgagcgtg ggtctcgcgg tatcattgca gcactggggc cagatggtaa    960
gccctcccgt atcgtagtta tctacacgac ggggagtcag gcaactatgg atgaacgaaa   1020
tagacagatc gctgagatag gtgcctcact gattaagcat tggtaactgt cagaccaagt   1080
ttactcatat atactttaga ttgatttaaa acttcatttt taatttaaaa ggatctaggt   1140
gaagatcctt tttgataatc tcatgaccaa aatcccttaa cgtgagtttt cgttccactg   1200
agcgtcagac cccgtagaaa agatcaaagg atcttcttga gatccttttt ttctgcgcgt   1260
aatctgctgc ttgcaaacaa aaaaaccacc gctaccagcg gtggtttgtt tgccggatca   1320
agagctacca actctttttc cgaaggtaac tggcttcagc agagcgcaga taccaaatac   1380
tgtccttcta gtgtagccgt agttaggcca ccacttcaag aactctgtag caccgcctac   1440
atacctcgct ctgctaatcc tgttaccagt ggctgctgcc agtggcgata agtcgtgtct   1500
taccgggttg gactcaagac gatagttacc ggataaggcg cagcggtcgg gctgaacggg   1560
gggttcgtgc acacagccca gcttggagcg aacgacctac accgaactga gatacctaca   1620
gcgtgagcta tgagaaagcg ccacgcttcc cgaagggaga aaggcggaca ggtatccggt   1680
aagcggcagg gtcggaacag gagagcgcac gagggagctt ccaggggaaa acgcctggta   1740
tctttatagt cctgtcgggt ttcgccacct ctgacttgag cgtcgatttt tgtgatgctc   1800
gtcagggggg cggagcctat ggaaaaacgc cagcaacgcg gccttttac ggttcctggc    1860
cttttgctgg ccttttgctc acatgttctt cctgcgtta ccctgatt ctgtggataa       1920
ccgtattacc gcctttgagt gagctgatac cgctcgccgc agccgaacga ccgagcgcag   1980
cgagtcagtg agcgaggaag cggaagagcg cctgatgcgg tattttctcc ttacgcatct   2040
gtgcggtatt tcacaccgca tatggtgcac tctcagtaca atctgctctg atgccgcata   2100
gttaagccag tatacactcc gctatcgcta cgtgactggg tcatggctgc gccccgacac   2160
ccgccaacac ccgctgacgc gccctgacgg gcttgtctgc tcccggcatc cgcttacaga   2220
caagctgtga ccgtctccgg gagctgcatg tgtcagaggt tttcaccgtc atcaccgaaa   2280
cgcgcgaggc agcatgcatc tcaattagtc agcaaccata gtcccgcccc taactccgcc   2340
catcccgccc ctaactccgc ccagttccgc ccattctccg ccccatggct gactaatttt   2400
ttttatttat gcagaggccg aggccgcctc ggcctctgag ctattccaga agtagtgagg   2460
aggctttttt ggaggcctag gcttttgcaa aaagctagct tacagctcag gctgcgatt    2520
tcgcgccaaa cttgacggca atcctagcgt gaaggctggt aggattttat ccccgctgcc   2580
atcatggttc gaccattgaa ctgcatcgtc gccgtgtccc aaaatatggg gattggcaag   2640
aacggagacc taccctggcc tccgctcagg aacgagttca agtacttcca agaatgacc    2700
acaacctctt cagtggaagg taaacagaat ctggtgatta tgggtaggaa aacctggttc   2760
tccattcctg agaagaatcg acctttaaag gacagaatta atatagttct cagtagagaa   2820
ctcaaagaac caccacgagg agctcatttt cttgccaaaa gtttggatga tgccttaaga   2880
cttattgaac aaccggaatt ggcaagtaaa gtagacatgg tttggatagt cggaggcagt   2940
tctgtttacc aggaagccat gaatcaacca ggccacctca gactctttgt gacaaggatc   3000
atgcaggaat ttgaaagtga cacgtttttc ccagaaattg atttgggaa atataaactt     3060
ctcccagaat acccaggcgt cctctctgag gtccaggagg aaaaaggcat caagtataag   3120
tttgaagtct acgagaagaa agactaacag gaagatgctt tcaagttctc tgctcccctc   3180
ctaaagctat gcatttttat aagaccatgg gacttttgct ggctttagat ctttgtgaag   3240
```

```
gaaccttact tctgtggtgt gacataattg gacaaactac ctacagagat ttaaagctct    3300
aaggtaaata taaaattttt aagtgtataa tgtgttaaac tactgattct aattgtttgt    3360
gtattttaga ttccaaccta tggaactgat gaatgggagc agtggtggaa tgcctttaat    3420
gaggaaaacc tgttttgctc agaagaaatg ccatctagtg atgatgaggc tactgctgac    3480
tctcaacatt ctactcctcc aaaaagaag agaaaggtag aagacccaa ggactttcct      3540 tcagaattgc taagtttttt gagtcatgct gtgtttagta atagaactct tgcttgcttt    3600
gctatttaca ccacaaagga aaaagctgca ctgctataca agaaaattat ggaaaaatat    3660
tctgtaacct ttataagtag gcataacagt tataatcata acatactgtt ttttcttact    3720
ccacacaggc atagagtgtc tgctattaat aactatgctc aaaaattgtg tacctttagc    3780
tttttaattt gtaaaggggt taataaggaa tatttgatgt atagtgcctt gactagagat    3840
cataatcagc ataccacat ttgtagaggt tttacttgct ttaaaaaacc tcccacacct     3900 cccctgaac ctgaaacata aaatgaatgc aattgttgtt gttaacttgt ttattgcagc     3960
ttataatggt tacaaataaa gcaatagcat cacaaatttc acaaataaag cattttttc     4020 actgcattct agttgtggtt tgtccaaact catcaatgta tcttatcatg tctactagtg    4080
gccggcccgg gcgatcgctc gagatatcta ttaatagtaa tcaattacgg ggtcattagt    4140
tcatagccca tatatggagt tccgcgttac ataacttacg gtaaatggcc cgcctggctg    4200
accgcccaac gacccccgcc cattgacgtc aataatgacg tatgttccca tagtaacgcc    4260
aatagggact ttccattgac gtcaatgggt ggagtattta cggtaaactg cccacttggc    4320
agtacatcaa gtgtatcata tgccaagtac gccccctatt gacgtcaatg acggtaaatg    4380
gcccgcctgg cattatgccc agtacatgac cttatgggac tttcctactt ggcagtacat    4440
ctacgtatta gtcatcgcta ttaccatggt gatgcggttt tggcagtaca tcaatgggcg    4500
tggatagcgg tttgactcac ggggatttcc aagtctccac cccattgacg tcaatgggag    4560
tttgttttgg caccaaaatc aacgggactt tccaaaatgt cgtaacaact ccgccccatt    4620
gacgcaaatg ggcggtaggc gtgtacggtg ggaggtctat ataagcagag ctcgtttagt    4680
gaaccgtcag atcgcctgga gacgccatcc acgctgtttt gacctccata agagacaccg    4740
ggaccgatcc agcctccgcg gccgggaacg gtgcattgga acgcggattc cccgtgccaa    4800
gagtgacgta agtaccgcct atagagtcta taggcccacc cccttggctt cttatgcatg    4860
ctatactgtt tttggcttgg ggtctataca ccccgcttc ctcatgttat aggtgatggt      4920
atagcttagc ctataggtgt gggttattga ccattattga ccactcccct attggtgacg    4980
atactttcca ttactaatcc ataacatggc tctttgccac aactctcttt attggctata    5040
tgccaataca ctgtccttca gagactgaca cggactctgt attttacag gatggggtct     5100 catttattat ttacaaattc acatatacaa caccaccgtc cccagtgccc gcagttttta    5160
ttaaacataa cgtgggatct ccacgcgaat ctcgggtacg tgttccggac atgggctctt    5220
ctccggtagc ggcggagctt ctacatccga gccctgctcc catgcctcca gcgactcatg    5280
gtcgctcggc agctccttgc tcctaacagt ggaggccaga cttaggcaca gcacgatgcc    5340
caccaccacc agtgtgccgc acaaggccgt ggcggtaggg tatgtgtctg aaaatgagct    5400
cggggagcgg gcttgcaccg ctgacgcatt tggaagactt aaggcagcgg cagaagaaga    5460
tgcaggcagc tgagttgttg tgttctgata agagtcagag gtaactcccg ttgcggtgct    5520
gttaacggtg gagggcagtg tagtctgagc agtactcgtt gctgccgcgc gcgccaccag    5580
acataatagc tgacagacta acagactgtt cctttccatg ggtcttttct gcagtcaccg    5640
```

```
tccttgacac gcgtctcggg aagcttgccg ccaccatgga catgagggtc cccgctcagc    5700
tcctggggct cctgctgctc tggctcccag gtgccaaatg tgaaattgtg ttgacgcagt    5760
ctccatcctc cctgtctgca tctgtaggag acagagtcac catcacttgc agtgccaggt    5820
caagtgtaag ttacatgcac tggttccagc agaaaccagg gaaagcccct aagctctgga    5880
tctataggac atccaacctg gcttctgggg tcccatctag attcagcggc agtggatctg    5940
ggacatctta ctgtctcacc atcaacagcc tgcagcctga agattttgca acttactatt    6000
gccagcaaag gagtagtttc ccactcacgt tcggcggagg gaccaagctg gagatcaaac    6060
gtgagtggat ccatctggga taagcatgct gttttctgtc tgtccctaac atgccctgtg    6120
attatgcgca acaacacac ccaagggcag aactttgtta cttaaacacc atcctgtttg     6180
cttctttcct caggaactgt ggctgcacca tctgtcttca tcttcccgcc atctgatgag    6240
cagttgaaat ctggaactgc ctctgttgtg tgcctgctga ataacttcta tcccagagag    6300
gccaaagtac agtggaaggt ggataacgcc ctccaatcgg gtaactccca ggagagtgtc    6360
acagagcagg acagcaagga cagcacctac agcctcagca gcaccctgac gctgagcaaa    6420
gcagactacg agaaacacaa agtctacgcc tgcgaagtca cccatcaggg cctgagctcg    6480
cccgtcacaa agagcttcaa caggggagag tgttagaggg agaagtgccc ccacctgctc    6540
ctcagttcca gcctgacccc ctcccatcct ttggcctctg accctttttc cacagggac    6600
ctaccccctat tgcggtcctc cagctcatct ttcacctcac ccccctcctc ctccttggct    6660
ttaattatgc taatgttgga ggagaatgaa taaataaagt gaatctttgc acctgtggtg    6720
gatctaataa aagatattta ttttcattag atatgtgtgt tggttttttg tgtgcagtgc    6780
ctctatctgg aggccaggta gggctggcct tgggggaggg ggaggccaga atgactccaa    6840
gagctacagg aaggcaggtc agagacccca ctggacaaac agtggctgga ctctgcacca    6900
taacacacaa tcaacagggg agtgagctgg aaatttgcta gcgaattcta ttaatagtaa    6960
tcaattacgg ggtcattagt tcatagccca tatatggagt tccgcgttac ataacttacg    7020
gtaaatggcc cgcctggctg accgcccaac gacccccgcc cattgacgtc aataatgacg    7080
tatgttccca tagtaacgcc aatagggact ttccattgac gtcaatgggt ggagtattta    7140
cggtaaactg cccacttggc agtacatcaa gtgtatcata tgccaagtac gccccctatt    7200
gacgtcaatg acggtaaatg gcccgcctgg cattatgccc agtacatgac cttatgggac    7260
tttcctactt ggcagtacat ctacgtatta gtcatcgcta ttaccatggt gatgcggttt    7320
tggcagtaca tcaatgggcg tggatagcgg tttgactcac ggggatttcc aagtctccac    7380
cccattgacg tcaatgggag tttgttttgg caccaaaatc aacgggactt tccaaaatgt    7440
cgtaacaact ccgccccatt gacgcaaatg ggcggtaggc gtgtacggtg ggaggtctat    7500
ataagcagag ctcgtttagt gaaccgtcag atcgcctgga gacgccatcc acgctgtttt    7560
gacctccata aagacaccg ggaccgatcc agcctccgcg gccgggaacg gtgcattgga     7620
acgcggattc cccgtgccaa gagtgacgta agtaccgcct atagagtcta taggcccacc    7680
cccttggctt cttatgcatg ctatactgtt tttggcttgg ggtctataca cccccgcttc    7740
ctcatgttat aggtgatggt atagcttagc ctataggtgt gggttattga ccattattga    7800
ccactcccct attggtgacg atactttcca ttactaatcc ataacatggc tctttgccac    7860
aactctcttt attggctata tgccaataca ctgtccttca gagactgaca cggactctgt    7920
attttacag gatgggtct catttattat ttacaaatt acatatacaa caccaccgtc      7980
```

```
cccagtgccc gcagttttta ttaaacataa cgtgggatct ccacgcgaat ctcgggtacg   8040
tgttccggac atgggctctt ctccggtagc ggcggagctt ctacatccga gccctgctcc   8100
catgcctcca gcgactcatg gtcgctcggc agctccttgc tcctaacagt ggaggccaga   8160
cttaggcaca gcacgatgcc caccaccacc agtgtgccgc acaaggccgt ggcggtaggg   8220
tatgtgtctg aaaatgagct cggggagcgg gcttgcaccg ctgacgcatt tggaagactt   8280
aaggcagcgg cagaagaaga tgcaggcagc tgagttgttg tgttctgata agagtcagag   8340
gtaactcccg ttgcggtgct gttaacggtg gagggcagtg tagtctgagc agtactcgtt   8400
gctgccgcgc gcgccaccag acataatagc tgacagacta acagactgtt cctttccatg   8460
ggtcttttct gcagtcaccg tccttgacac gcgtctcggg aagcttgccg ccaccatgga   8520
ctggacctgg aggatcctct tcttggtggc agcagcaaca ggtgcccact cccaggtgca   8580
gctggtgcaa tctgggtctg agcttaagaa gcctggggcc tcagtgaaga tctcctgcaa   8640
ggcttctgga tatactttca caaactatgg aatgaactgg gtgcgacagg cccctgggca   8700
agggcttcag tggatgggat ggataaacac cgacagtgga gagtcaacat atgctgaaga   8760
gttcaaggga cggtttgtct tctccttgga cacctctgtc aacacggcat atctgcagat   8820
caccagcctc acggctgagg acactggcat gtatttctgt gtgagagtcg gctacgatgc   8880
tttggactac tggggccagg gaaccctggt caccgtctcg agcgcctcca caagggccc   8940 atcggtcttc cccctggcac cctcctccaa gagcacctct gggggcacag cggccctggg   9000
ctgcctggtc aaggactact cccccgaacc ggtgacggtg tcgtggaact caggcgccct   9060
gaccagcggc gtgcacacct tcccggctgt cctacagtcc tcaggactct actccctcag   9120
cagcgtggtg accgtgccct ccagcagctt gggcacccag acctacatct gcaacgtgaa   9180
tcacaagccc agcaacacca aggtggacaa gaaagttgag cccaaatctt gtgacaaaac   9240
tcacacatgc ccaccgtgcc cagcacctga actcctgggg ggaccgtcag tcttcctctt   9300
ccccccaaaa cccaaggaca cctcatgat ctcccggacc cctgaggtca catgcgtggt   9360
ggtggacgtg agccacgaag accctgaggt caagttcaac tggtacgtgg acggcgtgga   9420
ggtgcataat gccaagacaa agccgcggga ggagcagtac aacagcacgt accgggtggt   9480
cagcgtcctc accgtcctgc accaggactg gctgaatggc aaggagtaca agtgcaaggt   9540
ctccaacaaa gccctcccag cccccatcga gaaaaccatc tccaaagcca agggcagccc   9600
ccgagaacca caggtgtaca ccctgccccc atcccgggag gagatgacca agaaccaggt   9660
cagcctgacc tgcctggtca aaggcttcta tcccagcgac atcgccgtgg agtgggagag   9720
caatgggcag ccggagaaca actacaagac cacgcctccc gtgctggact ccgacggctc   9780
cttcttcctc tacagcaagc tcaccgtgga caagagcagg tggcagcagg ggaacgtctt   9840
ctcatgctcc gtgatgcatg aggctctgca caaccactac acgcagaaga gcctctccct   9900
gtctccgggt aaatgagtgc gacggccggc aagccccgct ccccgggctc tcgcggtcgc   9960
acgaggatgc ttggcacgta cccctgtac atacttcccg ggcgcccagc atggaaataa  10020
agcaccggat ctaataaaag atatttattt tcattagata tgtgtgttgg ttttttgtgt  10080
gcagtgccta tatctggagg ccaggtaggg ctggccttgg gggaggggga ggcagaatgc  10140
actccaagag ctacaggaag gcaggtcaga gaccccactg gacaaacagt ggctggactc  10200
tgcaccataa cacacaatca acaggggagt gagctggaaa tttgctagcg aattaattc   10259
```

HUMANIZED IMMUNOMODULATORY MONOCLONAL ANTIBODIES FOR THE TREATMENT OF NEOPLASTIC DISEASE OR IMMUNODEFICIENCY

CROSS-REFERENCE TO RELATED APPLICATIONS

This application is a continuation of International application PCT/IL03/00425 filed May 22, 2003, the entire content of which is expressly incorporated herein by reference thereto.

FIELD OF THE INVENTION

The present invention relates to the field of immunotherapy and more specifically concerns humanized monoclonal antibodies useful for therapy of a variety of indications, particularly in the treatment of cancer.

BACKGROUND OF THE INVENTION

Cancer in its different forms is a major cause of death in humans. The most widely used therapeutic treatments of cancer are surgery, radiation and chemotherapy. The rapid increase of knowledge in recent years about the molecular and cellular bases of immune regulation, particularly at the level of T-cell responses, provides a new arsenal of immunotherapeutic approaches including the development of tumor vaccines. Certain monoclonal antibodies (MABS) were shown to have immunomodulatory activity including the ability to bind determinants on the surface of T cells and to induce proliferation, activation or differentiation of these cells.

Monoclonal antibodies derived from mouse hybridomas contain substantial stretches of amino acid sequences that are immunogenic when injected into a human patient, often eliminating the antibody's therapeutic efficacy after an initial treatment. While the production of so called "chimeric antibodies" (i. e. mouse variable regions joined to human constant. regions) has proven somewhat successful, a significant immunogenicity impediment remains.

Recombinant DNA technology has been utilized to produce immunoglobulins containing human framework regions (FRs) combined with complementarity determining regions (CDRs) from a donor mouse or rat immunoglobulin. These new proteins are called "reshaped" or "HUMANIZED" IMMUNOGLOBULINS and the process by which the donor immunoglobulin is converted into a human-like immunoglobulin by combining its CDRs with a human framework is called "humanization". Humanized antibodies are important because they bind to the same antigen as the original antibodies, but are less immunogenic when injected into humans.

U.S. Pat. No. 6,294,654 discloses a modified immunoglobulin molecule or functional fragment or part thereof (Ig), having an antigenic peptide foreign to the Ig incorporated in one or more non-CDR loops, and wherein the main outline of the constant domain framework is maintained. Further disclosed is the use of the modified antibody for therapeutic or prophylactic use.

U.S. Pat. No. 6,074,635 discloses a method for antigen independent activation of T cells in vitro comprising contacting T cells in the absence of antigen with a combination of at least two cytokines selected from the group consisting of interleukin-2, interleukin-6, and tumor necrosis factor alpha, or functionally equivalent fragments thereof.

U.S. Pat. No. 5,658,741 discloses a method of inducing the activation and proliferation of T-cells, said method comprising: (a) conjugating a plurality of T-cell specific monoclonal antibodies to an aminodextran molecule having 7-20% by weight amine groups and a molecular weight of at least 100,000 daltons, wherein the molar ratio of said antibodies to said aminodextran is greater than or equal to two; and (b) reacting said conjugate with a sample containing said T-cells to effect the binding of said conjugated antibodies to said T-cells to induce activation and proliferation of said T-cells.

U.S. Pat. No. 5,585,089 of Queen et al. discloses a humanized immunoglobulin having complementarity determining regions (CDRs) from a donor immunoglobulin and heavy and light chain variable region frameworks from human acceptor immunoglobulin heavy and light chains, which humanized immunoglobulin specifically binds to an antigen with an affinity constant of at least $10^7$ $M^{-1}$ and no greater than about four-fold that of the donor immunoglobulin, wherein said humanized immunoglobulin comprises amino acids from the donor immunoglobulin framework outside the Kabat and Chothia CDRs, wherein the donor amino acids replace corresponding amino acids in the acceptor immunoglobulin heavy or light chain frameworks, and each of said donor amino acids: (I) is adjacent to a CDR in the donor immunoglobulin sequence, or (II) contains an atom within a distance of 4 Å of a CDR in said humanized immunoglobulin.

U.S. Pat. No. 5,225,539, of Winter, discloses an altered antibody or antigen-binding fragment thereof, wherein a variable domain of the antibody or antigen-binding fragment has the framework regions of a first immunoglobulin heavy or light chain variable domain and the complementarity determining regions of a second immunoglobulin heavy or light chain variable domain, wherein said second immunoglobulin heavy or light chain variable domain is different from said first immunoglobulin heavy or light chain variable domain in antigen binding specificity, antigen binding affinity, species, class or subclass.

U.S. Pat. Nos. 5,225,539 and 5,585,089 do not provide sufficient tools and comprehensive description for carrying out the synthesis of an altered antibody, particularly a humanized antibody, by a person skilled in the art.

U.S. Pat. No. 5,897,862 of one of the inventors of the present invention which is incorporated herein by reference, discloses a monoclonal antibody or an antigen binding fragment thereof, wherein the monoclonal antibody: (i) is secreted by the hybridoma cell line deposited at the Collection Nationale de Cultures de Microorganismes (CNCM), under Accession No. I-1397, or (ii) recognizes the same antigenic epitope as the antibody under (i). The monoclonal antibody disclosed in U.S. Pat. No. 5,897,862 is directed against "Daudi" cells, a human B lymphoblastoid cell line, and was shown to stimulate murine lymphocytes and human peripheral blood T cells (Hardy et al, Cell Immunol. 118:22, 1989). This murine antibody is also termed mBAT-1 hereinafter. mBAT-1 also exhibits anti-tumor and immunostimulatory effects in various types of tumors (Hardy et al., Int. J. Oncol. 19:897, 2001) including tumors of human origin (Hardy et al., Proc. Natl. Acad. Sci. USA 94:5756, 1997).

International Patent Application WO 00/58363 of one of the inventors of the present invention which is incorporated herein by reference, discloses a monoclonal antibody having a variable region comprising the heavy chain variable region and/or the Kappa light chain variable region of mBAT-1 or a heavy chain variable region and/or a Kappa light chain variable region having at least 70% identity to the heavy chain variable region and/or the Kappa light chain variable region of mBAT-1.

Nowhere in the background art is it taught or suggested that a humanized monoclonal antibody comprising CDRs of a murine origin and FRs of a human origin may elicit an immune response and may further exhibit anti-cancer activity. Moreover, there is an unmet need for reliable methods for designing functional humanized antibodies, as it is well known in the art that the synthesis of the humanized antibody of the present invention cannot be predictably or routinely based on the background art.

SUMMARY OF THE INVENTION

The present invention now provides a humanized monoclonal immunomodulatory antibody, also termed hereinafter hBAT-1, which binds to B lymphoblastoid cells and induces proliferation and activation of peripheral blood lymphocytes. Said hBAT-1 is based on the previously known murine monoclonal immunomodulatory antibody, also termed herein mBAT-1, which binds to B lymphoblastoid cells and induces proliferation and activation of peripheral blood lymphocytes and further elicits an anti-tumor effect when injected into a tumor-bearing subject.

The present invention also provides a comprehensive description of the humanization process of mBAT-1 along with the rationale for each synthesis step. Thus, the description of the humanization process provided in the present invention is suitable for humanization of BAT antibodies other than mBAT-1, by a person skilled in the art.

The administration of humanized BAT-1 antibody offers a method for therapeutic prevention, detection or treatment of cancer. Treatment of a subject in need thereof with the humanized form of the BAT-1 antibody, as provided by the present invention, is considerably more efficient than treatment with a chimeric BAT-1 antibody, and avoids adverse immunogenic responses.

The present invention is based in part on the unexpected finding that the humanized BAT-1 antibody appears to induce a greater anti-tumor effect than that induced by the parent murine BAT-1 antibody.

According to a first aspect, the present invention provides a humanized monoclonal antibody, such as a humanized monoclonal immunomodulatory antibody, comprising at least one CDR from a donor immunoglobulin and an FR from an acceptor immunoglobulin. Advantageously, the donor of CDRs is the murine monoclonal BAT-1 antibody (mBAT-1). Also, the acceptor from which the FR is derived is preferably a human immunoglobulin.

According to yet another embodiment, the present invention provides a monoclonal immunomodulatory antibody comprising at least one CDR from a donor murine monoclonal BAT-1 antibody (mBAT-1) and an FR derived from an acceptor human immunoglobulin wherein the humanized antibody retains the biological activity of mBAT-1 monoclonal antibody and is less immunogenic in a human subject than said murine antibody.

According to yet another embodiment, the light chain variable region of the humanized BAT-1 antibody is characterized by the formula:

wherein each FR is independently a framework region of a human antibody and each CDR is independently a complementarity determining region of the monoclonal mBAT-1 antibody.

According to yet another embodiment, the heavy chain variable region of the humanized BAT-1 antibody is characterized by the formula:

wherein each FR is independently a framework region of a human antibody and each CDR is independently a complementarity determining region of the monoclonal mBAT-1 antibody.

According to a specific embodiment, the present invention provides a monoclonal antibody comprising FRs derived from the light chain variable region of the human TEL9 antibody.

According to another specific embodiment, the present invention provides a monoclonal antibody comprising FRs amino acid sequences derived from the light chain variable region of the human TEL9 antibody selected from the group consisting of: $FR_{L1}$, [EIVLT QSPSS LSASV GDRVT ITC; SEQ. ID NO. 1]; $FR_{L2}$, [W (F or Y) QQKPG KAPKL (W or L) IY; SEQ. ID NO. 2]; $FR_{L3}$, [GVPSR FSGSG SGT (D or S) (Y or F) (C or T) LTINS LQPED FATYY C; SEQ. ID NO. 3]; $FR_{L4}$, [FGGGT KLEIK; SEQ. ID NO. 4].

According to yet another specific embodiment, the present invention provides a monoclonal antibody comprising FRs derived from the heavy chain variable region of the human hsighv1295 antibody.

According to yet another specific embodiment, the present invention provides a monoclonal antibody comprising FRs amino acid sequences derived from the heavy chain variable region of the human hsighv1295 antibody selected from the group consisting of: $FR_{H1}$, [Q (I or V) QLV QSGSE LKKPG ASVKI SCKAS GY (T or S) F (T or S); SEQ. ID NO. 5]; $FR_{H2}$, [WV (R OR K) QAPGQ GL (Q or K) WMG; SEQ. ID NO. 6]; $FR_{H3}$, [RF (V or A) FSLDT SV (N or S) TAYLQ ITSL (T or N) AEDTG MYFC (V or A) (R or K); SEQ. ID NO. 7]; $FR_{H4}$, [WGQGT LVTVS S; SEQ. ID NO. 8].

According to yet another preferred embodiment, the present invention provides a monoclonal antibody comprising a light chain variable region comprising the amino acid sequence selected from the group consisting of: $CDR_{L1}$ [SARSS VSYMII; SEQ. ID NO.9]; $CDR_{L2}$ [RTSNL AS; SEQ. ID NO. 10]; $CDR_{L3}$ [QQRSS FPLT; SEQ. ID NO. 11], wherein the CDRs are derived from the murine BAT-1 antibody and the subscripts "L" and "H" refer to light and heavy chain regions, respectively.

According to yet another specific embodiment, the present invention provides a monoclonal antibody comprising a heavy chain variable region comprising the amino acid sequence selected from the group consisting of: $CDR_{H1}$ [NYGMN; SEQ. ID NO. 12]; $CDR_{H2}$ [WINTD SGEST YAEEF KG; SEQ. ID NO. 13]; $CDR_{H3}$ [VGYDA LDY; SEQ. ID NO. 14].

According to yet another embodiment, the humanized monoclonal antibody of the invention is selected from the group consisting of: a full length antibody having a human immunoglobulin constant region, a monoclonal IgG particularly of subclasses γ1 or γ4, a single chain antibody, an antibody fragment including, but not limited to, an F(ab')$_2$ fragment or F(ab) or Fv, a labeled antibody, an immobilized antibody, an antibody conjugated with a heterologous compound.

According to yet another preferred embodiment, the present invention provides a monoclonal antibody comprising a light chain variable region selected from the group consisting of: BATRκ$_A$ (SEQ. ID NO.15), BATRκ$_B$ (SEQ. ID NO.16), BATRκ$_C$ (SEQ. ID NO. 17), BATRκ$_D$ (SEQ. ID NO. 18).

According to yet another preferred embodiment, the present invention provides a monoclonal antibody comprising a heavy chain variable region selected from the group consisting of: BATRH$_A$ (SEQ. ID NO. 20), BATRH$_B$ (SEQ. ID NO. 21), BATRH$_C$ (SEQ. ID NO. 22), BATRH$_D$ (SEQ. ID NO. 23) or BATRH$_E$ (SEQ. ID NO. 24).

According to yet another preferred embodiment, the present invention provides a monoclonal antibody comprising a variable region selected from the group consisting of: BATRH$_A$/BATRκ$_A$ (SEQ. ID NO. 20/SEQ. ID NO. 15), BATRH$_B$/BATRκ$_A$ (SEQ. ID NO. 21/SEQ. ID NO. 15), BATRH$_B$/BATRκ$_B$ (SEQ. ID NO. 21/SEQ. ID NO. 16), BATRH$_C$/BATRκ$_B$ (SEQ. ID NO. 22/SEQ. ID NO. 16), BATRH$_B$/BATRκ$_D$ (SEQ. ID NO. 21/SEQ. ID NO. 18), or BATRH$_C$/BATRκ$_D$ (SEQ. ID NO. 22/SEQ. ID NO. 18).

According to yet another embodiment, the humanized monoclonal antibody of the invention is generated by recombinant DNA technology, utilizing CDR grafting.

According to a second aspect, the present invention provides polynucleotides encoding the humanized antibody of the invention or fragments thereof. The polynucleotides may encode the whole humanized antibody or the light chain variable region or the heavy chain variable region or both chains of the variable region of the humanized antibody. The invention further provides vectors comprising polynucleotides encoding the humanized antibody of the invention or fragments thereof. Consequently, the humanized BAT-1 antibody may be expressed in a host cell following co-transfection of the heavy and light chain vectors or by transfection of a single vector comprising both light and heavy chain polynucleotide sequences.

According to another embodiment, the present invention provides polynucleotide sequences encoding the humanized monoclonal antibody of the invention or fragments thereof.

According to another preferred embodiment, the present invention provides a polynucleotide sequence encoding the kappa light chain variable region of the humanized antibody of the invention wherein the kappa light chain variable region is selected from the group consisting of: SEQ ID NO. 15, SEQ ID NO. 16, SEQ ID NO. 17, SEQ ID NO. 18.

According to another preferred embodiment, the polynucleotide sequence encoding the light chain of the humanized antibody of the invention is selected from the group consisting of: SEQ ID NO. 87, SEQ ID NO. 88, SEQ ID NO. 89.

According to another preferred embodiment, the present invention provides a polynucleotide sequence encoding the heavy chain variable region of the humanized antibody of the invention wherein the heavy chain variable region is selected from the group consisting of: SEQ ID NO. 20, SEQ ID NO. 21, SEQ ID NO. 22, SEQ ID NO. 23, SEQ ID NO. 24.

According to yet another preferred embodiment, the polynucleotide sequences encoding the heavy chain of the humanized antibody of the invention are selected from the group consisting of: SEQ ID NO. 90, SEQ ID NO. 91, SEQ ID NO. 92.

According to yet another embodiment, the present invention provides a vector comprising the polynucleotide sequence encoding the humanized BAT-1 antibody or fragments thereof.

According to yet another embodiment, the present invention provides a vector comprising the polynucleotide sequence encoding the humanized antibody of the invention or fragments thereof.

According to yet another embodiment, the present invention provides a vector comprising the polynucleotide sequence encoding the humanized antibody of the invention or fragments thereof selected from the group consisting of: whole humanized antibody, the light chain variable region, the heavy chain variable region, both chains of the variable region.

According to yet another preferred embodiment, the present invention provides a vector comprising a polynucleotide sequence encoding the kappa light chain variable region of the humanized antibody of the invention, wherein the kappa light chain variable region is selected from the group consisting of: SEQ ID NO. 15, SEQ ID NO. 16, SEQ ID NO. 17, SEQ ID NO. 18.

According to yet another embodiment, the vector further comprises at least one sequence encoding a component selected from the group consisting of: resistance genes, promoter, signal peptide, polyA transcription terminator, selection markers, genomic human kappa constant region.

According to yet another preferred embodiment, the components of the vector are selected from the group consisting of: Ampicillin resistance gene, Neomycin resistance gene, HCMV Immediate Early Promoter, the genomic human kappa constant region, a mouse immunoglobulin signal peptide sequence, Kozak sequence, a signal sequence intron, BGH polyA transcription terminator, a Neo/G418 selection marker, a hamster dhfr selection marker.

According to yet another preferred embodiment, the present invention provides a vector comprising a polynucleotide sequence encoding the heavy chain variable region of the humanized antibody of the invention, wherein the heavy chain variable region is selected from the group consisting of: SEQ ID NO. 20, SEQ ID NO. 21, SEQ ID NO. 22, SEQ ID NO. 23, SEQ ID NO. 24.

According to yet another embodiment, the vector further comprises at least one sequence encoding a component selected from the group consisting of: resistance genes, promoter, signal peptide, polyA transcription terminator, selection markers, the genomic human Ig constant region.

According to yet another preferred embodiment, the components of the vector are selected from the group consisting of: Ampicillin resistance gene, Neomycin resistance gene, HCMV Immediate Early Promoter, the genomic human IgG1 constant region, a mouse immunoglobulin signal peptide sequence, Kozak sequence, a signal sequence intron, BGH polyA transcription terminator, a Neo/G418 selection marker, a hamster dhfr selection marker.

According to yet another preferred embodiment, the present invention provides a vector comprising a polynucleotide sequence encoding the kappa light chain variable region of the humanized antibody of the invention selected from the group consisting of: pKN110-BATRκ$_A$, pKN110-BATRκ$_B$ and pKN110-BATRκ$_D$.

According to yet another preferred embodiment, the present invention provides a vector comprising a polynucleotide sequence encoding the heavy chain variable region of the humanized antibody of the invention selected from the group consisting of: pG1D110-BATRH$_A$, pG1D110-BATRH$_B$, pG1D110-BATRH$_C$.

According to yet another preferred embodiment, the present invention provides a vector comprising a polynucleotide sequence encoding the complete humanized antibody of the invention of SEQ ID NO. 93.

According to a third aspect, the present invention provides cells containing a vector comprising the polynucleotide sequence encoding the antibody of the invention or fragments thereof for the purposes of storage, propagation, antibody production and therapeutic applications.

According to another embodiment, the host cell may be selected from the group consisting of: CHO, CHOdhfr, NSO, COS, COS7.

According to yet another embodiment, the present invention provides a pharmaceutical composition comprising as an active ingredient the antibody of the invention, for use in diagnosis and therapy.

According to yet another embodiment, the pharmaceutical composition comprising as an active ingredient the antibody of the invention is preferably used for the treatment of cancer.

According to yet another embodiment, the pharmaceutical composition may be administered either following detection of primary or secondary tumors in a subject or as preventive therapy of a subject having a high risk of developing cancers.

According to yet another preferred embodiment, the humanized antibody of the invention elicits anti-tumor effects in a variety of tumors.

According to yet another embodiment, the present invention provides a method for diagnosis or treatment of a disease or a disorder, particularly cancer, comprising administering to a subject in need thereof, an effective amount of a pharmaceutical composition comprising the antibody of the invention as an active ingredient.

According to yet another embodiment, the antibody of the invention in administered together with, prior to, or following, the administration of other agents, which can act in an additive or synergistic manner with it.

According to yet another embodiment, the antibody of the invention in administered together with, prior to, or following, the administration of agents selected from the group consisting of: cytokines, IL-1 (Interleukin-1), IL-2, IL-6, IFN-α (Interferon-α), cell vaccines, antibodies, T-cell stimulatory antibodies, anti-tumor therapeutic antibodies.

According to a particular embodiment of the present invention the humanized BAT monoclonal antibodies are identical in their function or activity to those produced by cells deposited under ATCC # (PTA-5189).

Other objects, features and advantages of the present invention will become apparent from the following detailed description and appended claims.

BRIEF DESCRIPTION OF THE DRAWINGS

FIG. 1 shows the DNA (SEQ ID NO: 25) and peptide (SEQ ID NO: 19) sequences of the kappa light chain variable region (Vκ) of the murine BAT-1 antibody.

FIG. 2 depicts the canonical classes of CDRs in the murine BAT-1 Vκ region. "Chothia Canonical Classes" indicates where the canonical classes as defined by Chothia and his colleagues (Chothia et al., 1987, 1989, 1992 ibid; Tramontano et al., J. Mol. Biol. 215:175, 1990) were used while "Martin Canonical Classes" signifies where the canonical classes defined by Martin and Thornton (Martin et al., J. Mol. Biol. 263:800, 1996) were used. FR residues are highlighted in bold. These sequences include: SNDTE (SEQ ID NO: 165); DLYVISNFHGT (SEQ ID NO: 166); SNTKG (SEQ ID NO: 167); FYNAHSR (SEQ ID NO: 168); MLVIF (SEQ ID NO: 169); QSGFL (SEQ ID NO: 170); NFG-SRDHTYV (SEQ ID NO: 171); NYWTSRQHAD (SEQ ID NO: 172); ENGHTSRAOHAD (SEQ ID NO: 173); DYTV-LHNIWPS (SEQ ID NO: 174); PLYRIWF (SEQ ID NO: 175).

FIG. 3 presents the DNA (SEQ ID NO: 27) and peptide (SEQ ID NO: 26) sequences of the heavy chain variable region ($V_H$) of the murine BAT-1 antibody.

FIG. 4 depicts the canonical classes of CDRs in the murine BAT-1 $V_H$ region. "Chothia Canonical Classes" indicates where the canonical classes as defined by Chothia and his colleagues (Chothia et al., 1987, 1989, 1992 ibid; Tramontano et al., ibid) were used while "Martin Canonical Classes" signifies where the canonical classes defined by Martin and Thornton (Martin et al., ibid) were used. FR residues are highlighted in bold. These sequences include: TAVGS (SEQ ID NO: 176); MIVLT (SEQ ID NO: 177); RTKHGL (SEQ ID NO: 178); IHYFTNCED (SEQ ID NO: 179); YAWGTLV (SEQ ID NO: 180); HENOSYT (SEQ ID NO: 181); LIVTSN (SEQ ID NO: 182); ILFMV (SEQ ID NO: 183); ALVYF (SEQ ID NO: 184); RKGSHN (SEQ ID NO: 185); YHVISDG (SEQ ID NO: 186); YWGATL (SEQ ID NO: 187); REWYGOVLNKA (SEQ ID NO: 188): DLNSY (SEQ ID NO: 189): AGYSKTN (SEQ ID NO: 190): NSTKDG (SEQ ID NO: 191): YREDGVSA (SEQ ID NO: 192): KNTSDRGFY (SEQ ID NO: 193).

FIG. 5 shows the amino acid sequences of the various versions of the humanized BAT-1 $V_\kappa$ region that are proposed (SEQ ID NOS. 15-18). Where the BAT-1 $V_\kappa$ region residues and the human TEL9 $V_\kappa$ region sequence match a dot [.] is shown. Where no amino acid is present at a specific residue position a dash [-] is shown. Where an amino acid in the TEL9 FRs is changed in the humanized BAT-1 $V_\kappa$ region, it is highlighted in bold. The CDRs are described by the use of the nomenclature [==L1==]. The numbering used is as according to Kabat (Kabat et al., Sequences of proteins of immunological interest, Fifth Edition, U.S. Department of Health and Human Services, U.S. Government Printing Office, 1991).

FIG. 6 presents the amino acid sequences of the various versions of the humanized BAT-1 $V_H$ region that are proposed (SEQ ID NOS. 20-24). Where the BAT-1 $V_H$ region residues and the human hsighv1295 $V_H$ region sequence match a dot [.] is shown. Where no amino acid is present at a specific residue position a dash [-] is shown. Where an amino acid in the hsighv1295 FRs is changed in the humanized BAT-1 $V_H$ region, it is highlighted in bold. The CDRs are described by the use of the nomenclature [==H1==], while [-----] denotes part of the H1 structural loop. The numbering used is as according to Kabat (Kabat et al., ibid).

FIG. 7 shows the DNA (SEQ ID NO. 87) and peptide (SEQ ID NO. 15) sequences of version A (BATRκ$_A$) of the reshaped human kappa light chain variable region of the humanized BAT-1 antibody.

FIG. 8 shows the DNA (SEQ ID NO. 88) and peptide (SEQ ID NO. 16) of version B (BATRκ$_B$) of the reshaped human kappa light chain variable region of the humanized BAT-1 antibody.

FIG. 9 presents the DNA (SEQ ID NO. 89) and peptide (SEQ ID NO. 18) sequences of version D (BATRκ$_D$) of the reshaped human kappa light chain variable region of the humanized BAT-1 antibody.

FIG. 26 presents binding of the humanized BATRH$_C$/BATRκ$_D$ γ1 mAb to cellular markers CD19 (A) and CD20 (B) of B lymphocytes isolated from a normal donor.

FIG. 31 describes hBAT induced increase in the number of viable CD4+ cells, isolated from two separate donors (A and B).

DETAILED DESCRIPTION OF THE PREFERRED EMBODIMENTS

I. Definitions

Figure 10:
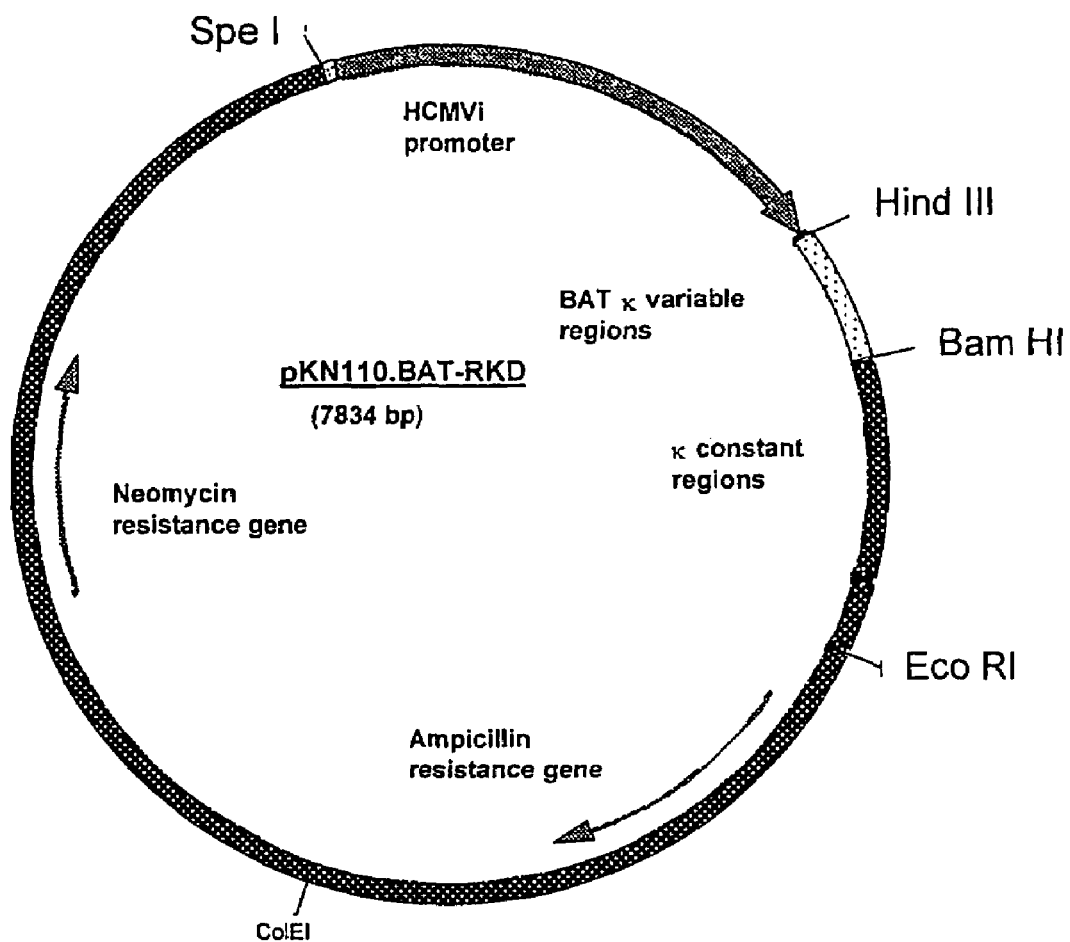
FIG. 10 is a diagrammatic representation of the pKN110-BATRκ$_D$ vector construct.

For convenience certain terms employed in the specifications, examples and claims are set forth.

The term "antibody" is used in the broadest sense and specifically covers monoclonal antibodies (including full length monoclonal antibodies) and antibody fragments so long as they exhibit the desired biological activity. "Antibody fragments" comprise a portion of a full length antibody, generally the antigen binding or variable region thereof. Examples of antibody fragments include Fab, Fab', F(ab')$_2$, and Fv fragments; diabodies; linear antibodies; single-chain antibody molecules; and multispecific antibodies formed from antibody fragments.

The term "monoclonal antibody" as used herein refers to antibodies that are highly specific, being directed against a single antigenic site. The monoclonal antibodies to be used in accordance with the present invention may be made by recombinant DNA methods (see, e.g., U.S. Pat. No. 4,816,567 of Cabilly et al.).

The term "framework region" or "FR" residues are those variable domain residues other than the hypervariable region residues as herein defined. The term "hypervariable region" when used herein refers to the amino acid residues of an antibody which are responsible for antigen binding. The hypervariable region comprises amino acid residues from a "complementarity determining region" or "CDR". The CDRs are primarily responsible for binding to an epitope of an antigen. The extent of FRs and CDRs has been precisely defined (see, Kabat et al., ibid).

As used herein, the term "humanized antibody" refers to an antibody comprising a framework region from a human antibody and one or more CDRs from a non-human (usually a mouse or rat) immunoglobulin. Parts of a humanized immunoglobulin, except possibly the CDRs, are substantially identical to corresponding parts of natural human immunoglobulin sequences. Importantly, the humanized antibody is expected to bind to the same antigen as the donor antibody that provides the CDRs. For further details, see e.g. U.S. Pat. No. 5,225,539 assigned to Medical Research Council, UK.

The expression "human antibody" is intended to mean an antibody encoded by a gene actually occurring in a human, or an allele, variant or mutant thereof.

As used herein, the term "donor" or "parental" immunoglobulin refers to the non-human immunoglobulin providing the CDRs.

As used herein, the term "acceptor" immunoglobulin refers to the human immunoglobulin providing the framework.

The term "expression vector" as used herein refers to a recombinant DNA molecule containing a desired coding sequence and appropriate nucleic acid sequences necessary for the expression of the operably linked coding sequence in a particular host cell. It is contemplated that the present invention encompasses expression vectors that are integrated into host cell genomes, as well as vectors that remain unintegrated into the host genome.

The term "genetically modified cells" as referred to herein relates to cells being transfected or infected by a vector, as exemplified by a virus encoding a polypeptide of interest, said cells capable of expressing said polypeptide. Particularly in the context of this invention, the genetically modified cells are capable of expressing and secreting the antibody of the invention.

The term "transfection" refers to the introduction of DNA into a host cell. It is contemplated that coding sequences may be expressed in transfected cells. Numerous methods of transfection are known to the ordinary skilled artisan, for example, $CaPO_4$ and electroporation.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the antibody of the invention in prevention of the occurrence of tumor in the first place. Given its properties, the antibody of the invention can be used both in the treatment of acute cancer as well as in cancer prophylaxis.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols. Pharmaceutical compositions may also include one or more additional active ingredients.

The term "Polymerase Chain Reaction" ("PCR") refers to the methods disclosed in U.S. Pat. Nos. 4,683,195; 4,683,202, and 4,965,188.

II. Preferred Modes for Carrying Out the Invention a. Antibody Preparation

In order to humanize the BAT-1 antibody, the non-human antibody starting material, namely mBAT-1 is prepared, following the design and preparation of the humanized variants. Some aspects of this invention, including the selection of a donor non-human antibody variable domain, humanizing an antibody gene sequence and producing a desired humanized antibody, are described in the following sections.

(i) Preparation of the Non-Humanized Antibody

The murine BAT-1 monoclonal antibody was described previously in U.S. Pat. No. 5,897,862. Accordingly, a representative hybridoma cell line that produces monoclonal murine BAT-1 antibodies, was deposited at the Collection Nationale de Cultures de Microorganismes (CNCM), Institute Pasteur, 25, Rue du Docteur Roux, 75724, Paris, Cedex 15, under Deposit Accession No. I-1397, on Jan. 28, 1994.

Alternatively, the chimeric γ1/κ BAT-1 antibody as produced from the murine BAT-1 may be used for the preparation of a humanized BAT-1. The chimeric BAT-1 antibody and its production, have been described in PCT application No. WO 00/58363.

(ii) Design Strategy of the Humanized Antibody

The present invention discloses procedures for humanization of BAT-1 antibody via a process in which the donor antibody, preferably mouse antibody, is converted into a human-like antibody by combining the CDRs of the donor antibody with a human framework. In certain embodiments, it may be desirable to generate amino acid sequence variants of the humanized antibody, particularly where these improve the binding affinity or other properties of the humanized antibody. The methods applied to select sites for substitution, insertion or deletion, from both the donor BAT-1 antibody and the selected human acceptor antibody, including the selection of acceptor human antibodies are described in detail. The extensive analysis and guidelines for antibody humanization which is provided hereinbelow, is not disclosed in the background art and is crucial for the preparation of an active altered antibody.

The design of a humanized antibody is preferably initiated by sequence analysis of the heavy and light chains of the non-human antibody variable region, also termed hereinafter $V_H$ and $V_L$, respectively. Such analysis includes a comparison between the amino acid sequence of $V_L$ and $V_H$ of the non-humanized antibody and other mouse variable regions. In a preferred embodiment, the comparison can be further conducted with consensus sequences of the subgroups into which the variable regions were subdivided in the Kabat database (Kabat et al., ibid). The classification of the different elements of the variable region facilitates selection of immunoglobulin variable regions which are similar to the $V_L$ and $V_H$ of the non-humanized antibody of the present invention and are structurally solved.

Selection of the human kappa light chain variable region, also termed hereinafter $V_\kappa$, and of $V_H$ that would serve as the basis of the variable region of the humanized antibody, also termed an acceptor antibody, is preferably initiated by classifying the $V_L$ and $V_H$ of the non human antibody according to consensus sequences of human immunoglobulins. Particularly, $V_L$ of the non-humanized antibody is compared with and consequently categorized according to the consensus sequences of the four human kappa light chain variable region subgroups as defined by Kabat (Kabat et al., ibid). Similarly, $V_H$ of the non-humanized antibody is compared and categorized according to the consensus sequences of the three human heavy chain variable region subgroups.

The selection of the acceptor human $V_\kappa$ and $V_H$ is preferably proceeded by conducting a comparison between $V_L$ and $V_H$ of the parental non-human antibody of the invention and all the recorded examples of individual sequences of human variable regions publicly available. An appropriate human $V_\kappa$ and $V_H$ are selected on the basis of closest match to the parental non-human antibody.

Analysis of the sequences of the donor and humanized antibodies and reference to appropriate molecular models can help to discern which residues might be involved in antigen binding or maintenance of proper antibody structure and which residues should be removed or substituted in order to improve the structure of the humanized antibody.

Molecular models of the variable regions of both the non-human and humanized antibodies are thus prepared to assist the design of the humanized antibody. The modeling of these structures are based on the classifications of the variable region elements that were determined in the analysis procedure and can be obtained, for example, by using homology and ab initio techniques. The corresponding X-ray crystallographic structures can be obtained from the Brookhaven database.

Elements within the variable region of the non-human antibody of the invention, such as FRs, CDRs, and loop structures, are modeled on elements from similar, structurally solved, immunoglobulin variable regions. Steric clashes are identified in the models and consequently mismatched side-chains are selected for substitution. A particularly preferred approach for structure conformation includes categorization of the structural elements according to canonical classes based on those described by Chothia and his colleagues (Chothia et al., 1987, 1989, 1992 ibid; Tramontano et al., ibid). A preferred approach for structure prediction includes a database search or CONGEN search (Bruccoleri, R. E. et al., *Biopolymers* 26:137, 1987). The selected human $V_\kappa$ and $V_H$ that would serve as the basis of the humanized antibody are similarly modeled and their amino acid sequences are studied to determine if any of their residues are likely to adversely influence binding specificity.

Energy minimization is preferably applied after adjusting the models for obvious steric clashes. Energy minimization is implemented here both to relieve unfavorable atomic contacts and to optimize van der Waals and electrostatic interaction.

As a result of the above design procedure the humanized antibody variants of BAT-1 may comprise additional, or substituted conservative amino acid residues which are not found in the recipient antibody or in the donor antibody. Deletion of amino acid residues included in the original acceptor or donor antibodies may also be applied. These modifications are made to refine antibody performance and have substantially no effect on antigen binding or other immunoglobulin functions. The sites of greatest interest for modifications include the hypervariable loops, but FR alterations are also contemplated. Hypervariable region residues or FR residues involved in antigen binding are generally substituted in a relatively conservative manner. The conservative substitutions that may be applied in the present invention comprise the following options: Val, Ile; Ser, Thr; Lys, Arg; Phe, Tyr; Trp, Leu; Asp, Ser; Cys, Thr; Gln, Lys; Val, Ala; Asn, Ser; Thr, Asn.

(iii) Construction of the Humanized Antibody Variants

Generally, the BAT-1 antibody variants are conventionally prepared in recombinant cell culture, as described in more detail below. Recombinant synthesis is preferred here but it is known to prepare peptides by chemical synthesis or to purify them from natural sources.

Molecular biology techniques and CDR grafting protocols suitable to carrying out the invention as herein described are known to those skilled in the art. Suitable teachings are described in numerous manuals and primary publications, including inter alia, Sambrook et al., (Molecular Cloning: A Laboratory Manual, 2nd Ed., Cold Spring Harbor Laboratory Press, Cold Spring Harbor, N.Y., 1989); Ausubel et al., (Protocols In Molecular Biology, Green Publishing Associates and Wiley-Interscience, John Wiley and Sons, New York 1987, 1988, 1989); U.S. Pat. Nos. 5,225,539 and 5,585,089 which are herein incorporated by reference in their entirety including supplements.

The amino acid sequences of BAT-1 light and heavy chain CDRs are herein identified and illustrated in FIGS. 5 and 6: $CDR_{L1}$ (SEQ. ID NO. 9 and SEQ L1 in FIG. 5): SARSS VSYMH; $CDR_{L2}$ (SEQ. ID NO. 10 and SEQ L2 in FIG. 5): RTSNL AS; $CDR_{L3}$ (SEQ. ID NO. 11 and SEQ L3 in FIG. 5): QQRSS FPLT; $CDR_{H1}$ (SEQ. ID NO. 12 and SEQ H1 in FIG. 6): NYGMN; $CDR_{H2}$ (SEQ. ID NO. 13 and SEQ H2 in FIG. 6): WINTD SGEST YAEEF KG; $CDR_{H3}$ (SEQ. ID NO. 14 and SEQ H3 in FIG. 6): VGYDA LDY.

Using these amino acid sequences, oligonucleotides encoding these CDRs can be synthesized for use in the present invention. Also, the oligonucleotides may contain nucleotides in addition to those of BAT-1 CDRs, to facilitate cloning or to introduce restriction sites, for instance. Oligonucleotide synthesis techniques suitable to this aspect of the invention are well known to the skilled artisan and may be carried out using any of several commercially available automated synthesizers. In addition, DNAs encoding the CDRs set forth herein can be obtained through the services of commercial DNA synthesis vendors. It is thus not necessary to reclone BAT-1 CDRs from a natural source.

mBAT-1 CDRs are grafted into a human antibody to produce the humanized BAT-1 variants. It will be understood that human antibody in this context refers to any antibody that occurs in a human or an engineered antibody that has been designed, in some respect, to be compatible with the human immune system. Particularly preferred for this purpose are antibodies that, broadly, do not engender an adverse immune response in a patient.

To construct CDR-grafted humanized BAT-1 antibodies, oligonucleotides encoding the BAT-1 CDRs can be integrated into other DNAs encoding antibody heavy and light chains and fragments thereof, using well-known recombinant techniques such as those described in the above references. Particularly, BAT-1 CDRs can be introduced into practically any set of FRs in accordance with the present invention. A variety of human antibody genes are available in the form of publicly accessible deposits and suitable antibody genes can be synthesized from these sequences much as described above. Preferred techniques employed in this regard, for cloning and manipulating polynucleotides are illustrated by the methods and examples set forth.

The amino acid sequences of mBAT-1 and reshaped BAT-1 light (FIG. 5) and heavy (FIG. 6) chain FRs and modified FRs are herein identified: $FR_{L1}$ (SEQ. ID NO.1): EIVLT QSPSS LSASV GDRVT ITC; $FR_{L2}$ (SEQ. ID NO. 2): WXaaQQK PGKAP KLXbbI Y, wherein Xaa=F, Y and Xbb=W, L; $FR_{L3}$ (SEQ. ID NO. 3): GVPSR FSGSG SGTXaaXbb XccLTIN SLQPE DFATY YC, wherein Xaa=D, S; Xbb=Y, F and Xcc=C, T; $FR_{L4}$ (SEQ. ID NO. 4): FGGGT KLEIK; $FR_{H1}$ (SEQ. ID NO. 5): QXaaQLV QSGSE LKKPG ASVKI SCKAS GYXbbFXcc, wherein Xaa=I, V; Xbb=T, S; Xcc=T, S; $FR_{H2}$ (SEQ. ID NO. 6): WVXaaQA PGQGL XbbWMG, wherein Xaa=R, K; Xbb=Q, K; $FR_{H3}$ (SEQ. ID NO. 7): RFXaaFS LDTSV XbbTAYL QITSL XccAEDT GMYFC XddXee, wherein Xaa=V, A; Xbb=N, .S; Xcc=T, N; Xdd=V, A; Xee=R, K; $FR_{H4}$ (SEQ. ID NO. 8): WGQGT LVTVS S.

The oligonucleotides encoding the BAT-1 CDRs and/or specific FR residues originated from human antibodies may be used to introduce codons into the DNA encoding $V_\kappa$ or $V_H$ of the humanized BAT-1 variants. In accordance with this aspect of the invention the additional codons may include those not derived from BAT-1 CDR as well as those that make up the CDR. These additional bases may be included to facilitate joining the CDR to the FRs from a heterologous source. They may comprise restriction sites or overlapping complementary regions for this purpose. The template DNAs are typically single-stranded DNAs (ssDNAs) vectors.

The CDRs of the BAT-1 heavy and light chains may also be modified particularly after incorporation into a humanized antibody using well-known recombinant DNA techniques for deleting, inserting and altering bases in a cloned or synthetic DNA or RNA. Site-specific mutagenesis techniques suitable to this end are well known to those of skill in the art, and are illustrated in the foregoing references on recombinant DNA techniques. These methods can be used to introduce practically any desired alteration into polynucleotides that encode the BAT-1 CDRs or into other regions of a closed heavy or light chain gene.

The synthesis of longer, double-stranded DNAs from shorter, overlapping, single-stranded DNAs is well known to those of skill in the art. Likewise, well known is the end-to-end joining of DNAs, including blunt-ended DNAs and those with at least partially overlapping complementary termini. These techniques are illustrated in the foregoing references on recombinant DNA techniques, for instance.

The construction of all versions of the human BAT-1 variable region is preferably carried out as described by Stemmer (Stemmer et al., GENE 164:49, 1995). Essentially, this method is favored for the synthesis of long DNA sequences from large numbers of oligodeoxyribonucleotides (oligos). The method relies on DNA polymerase using conventional PCR technique, to build increasingly longer DNA fragments during assembly process. Once the new variable region gene is synthesized it is preferentially subcloned into a vector which is transformed into competent cells as described in the above references. Putative positive clones can be identified by PCR-screening using appropriate primers and/or by restriction digest. Individual clones selected from the confirmed positive clones may be sequenced to double-stranded-DNA (ds-DNA). Preferably, the resultant ds-DNAs can be rechecked for PCR-induced errors, by sequencing, and corrected by subcloning correct fragments from other clones.

DNA of selected clones, from the confirmed positive clone, containing the humanized $V_\kappa$ or $V_H$ of the BAT-1 variant may be directly inserted into expression vectors which comprise human light and heavy constant regions, respectively. Once DNA encoding the humanized BAT-1 CDR-grafted complete antibody variant, or the light or the heavy chain regions of the humanized BAT-1 CDR-grafted antibody, has been assembled, it may be inserted into a vector for propagation and expression by conventional techniques. In this manner desired amounts of the antibody may be obtained.

(iv) Expression of the Humanized BAT-1 Antibody Variants

The invention also provides isolated polynucleotide sequences encoding the complete humanized BAT-1 antibody, the light chain complete or variable region, heavy chain complete or variable region sequence, as well as vectors and host cells comprising the coding nucleic acid.

For recombinant production of the BAT-1 antibody, the polynucleotide sequence encoding said antibody or its fragments, is isolated and inserted into a replicable vector for further cloning, amplification or for expression. DNA encoding the antibody is readily isolated and sequenced using conventional procedures (e.g., by using oligonucleotide probes that are capable of binding specifically to genes encoding the heavy and light chains of the antibody). Many vectors are available which generally include, but are not limited to, one or more of the following: a signal sequence, an origin of replication, one or more marker genes, an enhancer element, a promoter, and a transcription termination sequence.

For expression, the polynucleotide encoding the humanized BAT-1 antibody or fragments thereof, may be cloned into an expression vector. Such vectors are well known to those skilled in the art. An expression control sequence, such as an immunoglobulin or viral promoter, is introduced upstream of the polynucleotide. Selection markers such as the dhfr gene, or other suitable selectable marker well known to those skilled in the art, are included in the vector to allow selection of host cells which are expressing the said polynucleotide included on the vector.

In one embodiment, the host cell endogenously produces antibodies, while in an alternative embodiment, the cell is genetically modified to produce antibodies. Examples of cells that endogenously produce antibodies include, but are not limited to hybridomas, lymphomas, plasmacytomas and EBV transformed cells. A cell can be genetically modified to produce antibodies by conventional methods, such as by transfection with a vector encoding an antibody molecule.

In use, the expression vector comprising the polynucleotide encoding the humanized BAT-1 antibody or fragments thereof, is transfected into cells. Transfection methods are well known in the art and such methods are suitable for employment in the present invention. The cells expressing the expression vector are selected using the selectable marker incorporated into the expression vector or a vector used for co-transfection. Cells expressing the antibody can be screened by enzyme-linked immunoabsorbent assay (ELISA) assays or other suitable methods well known to those skilled in the art.

The humanized BAT-1 antibody variants are introduced into a host cell by transfection of a vector comprising polynucleotide encoding the complete or Fv fragment of the antibody. Humanized BAT-1 antibody variants is also introduced into a host cells by co-transfection of: (i) a vector comprising polynucleotide encoding the variable or complete light chain region of the antibody and (ii) a vector comprising polynucleotide encoding the variable or complete heavy chain region of the antibody.

In a most preferred embodiment, the antibody of the invention is produced by a transfection of a single vector comprising polynucleotide sequences encoding the light and heavy variable regions of the antibody. Most preferably, this vector further comprises two promoters, each operatively linked to the polynucleotide sequence encoding the light chain and the heavy chain regions of reshaped BAT-1. The resulting expression of the BAT-1 antibody is higher than its expression following co-transfection with two vectors, each encoding the light chain or heavy chain regions, of the antibody, whereas the transfection and co-transfection being conducted in a similar host cell.

The humanized BAT-1 antibody variants can be expressed in any suitable cell type, including but not limited to mammalian, avian, insect, bacterial or yeast cells. Examples of mammalian cells include, but are not limited to, human, rabbit, rodent (e.g., mouse, rat) and bovine cells. In preferred embodiments, the cell is a myeloma cell, a Chinese hamster ovary (CHO) cell, COS cell, COS7 cell or fibroblast.

Antibody-producing cell lines may be cultured using techniques well known to the skilled artisan. Such techniques are described in a variety of laboratory manuals and primary publications. For instance, techniques suitable for use in the invention as described below are described in current protocols in immunology, Coligan et al., (Green Publishing Associates and Wiley-Interscience, John Wiley & Sons, N.Y. 1991) which is herein incorporated by reference in its entirety, including supplements.

The humanized monoclonal antibodies of the invention can be frozen or lyophilized for storage and reconstituted in a suitable carrier prior to use. This technique has been shown to be effective with conventional immune globulins and art-known lyophilization and reconstitution techniques can be employed. It will be appreciated by those skilled in the art that lyophilization and reconstitution can lead to varying degrees of antibody activity loss and that use levels may have to be adjusted to compensate.

(v) Purification of Humanized BAT-1 Antibody

Using recombinant techniques, the antibody can be produced intracellularly, in the periplasmic space, or directly secreted into the medium. If the antibody is produced intracellularly, as a first step the particulate debris, either host cells or lysed fragments, is removed, for example, by centrifugation or ultrafiltration. Carter et al., (Biotechnology 10:163, 1992) describe a procedure for isolating antibodies which are secreted to the periplasmic space of *E. coli*.

Briefly, cell paste is thawed in the presence of sodium acetate (pH 3.5), EDTA, and phenylmethylsulfonylfluoride (PMSF) over about 30 min. Cell debris can be removed by centrifugation.

In a most preferred embodiment, the antibody of the invention is secreted into the medium, supernatants from such expression systems are generally first concentrated using a commercially available protein concentration filter, for example, an Amicon or Millipore ultrafiltration unit. A protease inhibitor may be included in any of the foregoing steps to inhibit proteolysis and antibiotics may be included to prevent the growth of adventitious contaminants.

The antibody composition prepared from the cells can be purified using methods well known in the art, for example, hydroxyapatite chromatography, gel electrophoresis, dialysis, and affinity chromatography, with affinity chromatography particularly with protein A, being a preferred purification technique. The matrix to which the affinity ligand is attached is most often agarose, but other matrices are available. Mechanically stable matrices, such as controlled pore glass or poly(styrenedivinyl)benzene, allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, reverse phase HPLC, chromatography on silica, chromatography on heparin SEPHAROSE™, chromatography on an anion or cation exchange resin (such as a polyaspartic acid column), chromatofocusing, SDS-page, and ammonium sulfate precipitation are also available depending on the antibody to be recovered.

(vi) Deposit of Cell Line

According to a representative embodiment of the present invention the humanized BAT monoclonal antibodies are identical in their function or activity to those produced by cells deposited under ATCC # (PTA-5189), on May 9, 2003.

III. Pharmacology (i) Pharmaceutical Compositions

The invention also provides a composition comprising the antibody of the invention.

According to another embodiment, the present invention provides a pharmaceutical composition comprising as an active ingredient the antibody of the invention, for use in diagnosis and therapy. Said compositions may be in any pharmaceutical form suitable for administration to a patient, including but not limited to solutions, suspensions, lyophilized powders for reconstitution with a suitable vehicle or dilution prior to usage, capsules and tablets. The pharmaceutical compositions disclosed in this invention may further comprise any pharmaceutically acceptable diluent or carrier to provide a physiologically acceptable conjugates comprising the antibodies with therapeutic agents for diagnosis, prognosis and therapy, among others.

Pharmaceutical compositions of the present invention may be manufactured by processes well known in the art, e.g., by means of conventional mixing, dissolving, granulating, grinding, pulverizing, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active compounds into preparations which, can be used pharmaceutically. Proper formulation is dependent upon the route of administration chosen.

For injection, the compounds of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants, for example polyethylene glycol, are generally known in the art. Pharmaceutical compositions which can be used orally, include push-fit capsules.

For administration by inhalation, the molecules for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator, may be formulated containing a powder mix of the polypeptide and a suitable powder base such as lactose or starch.

Pharmaceutical compositions for parenteral administration include aqueous solutions of the active ingredients in water-soluble form. Additionally, suspensions of the active compounds may be prepared as appropriate oily injection suspensions. Suitable natural or synthetic carriers are well known in the art. Optionally, the suspension may also contain suitable stabilizers or agents, which increase the solubility of the compounds, to allow for the preparation of highly concentrated solutions. Alternatively, the active ingredient may be in powder form for reconstitution with a suitable vehicle, e.g., sterile pyrogen-free water, before use.

Pharmaceutical compositions suitable for use in context of the present invention include compositions wherein the active ingredients are contained in an amount effective to achieve the intended purpose. All formulations for administration should be in dosages suitable for the chosen route of administration. More specifically, a "therapeutically effective" dose means an amount of a compound effective to prevent, alleviate or ameliorate symptoms of a disease of the subject being treated. Determination of a therapeutically effective amount is well within the capability of those skilled in the art, especially in light of the detailed disclosure provided herein.

Toxicity and therapeutic efficacy of the compositions described herein can be determined by standard pharmaceutical procedures in cell cultures or experimental animals, e.g., by determining the $IC_{50}$ (the concentration which provides 50% inhibition) and the maximal tolerated dose for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will, of course, be dependent on the subject being treated, the severity of the affliction, the manner of administration, the judgment of the prescribing physician, and all other relevant factors.

(ii) Methods of Treatment

Antibodies in accordance with the invention, while being useful for a variety of therapeutic indications, are used, in accordance with a currently preferred embodiment of the invention, for the treatment of cancer. It has been found that a monoclonal antibody in accordance with the invention elicits anti-tumor effects in a variety of tumors. Within the scope of the present invention, methods are provided for the use of the novel hBAT-1 for the treatment of tumor by administering to a subject an effective amount of the antibody of the invention. The term "effective amount" should be understood as meaning an amount of an antibody required to achieve a therapeutic effect. The effective amount required to achieve the therapeutic end result may depend on a number of factors including, for example, the tumor type and the severity of the patient's condition (i.e. the cancerous state), and whether the antibody is co-administered together with another agent which acts together with the antibody in an additive or synergistic manner. The antibody may be administered either following detection of primary or secondary tumors in the subject or, as preventive therapy of a subject having a high risk of developing cancers, such as an individual exposed to radiation or such having a genetic pre-disposition.

The invention additionally provides a method of treating a subject in need thereof, with a humanized BAT-1 antibody variant or with a composition that comprises said antibody as an active ingredient.

According to yet another embodiment, the present invention provides a method for diagnosis or treatment of a disease or a disorder, particularly cancer, comprising administering to a subject in need thereof, an effective amount of a pharmaceutical composition comprising the antibody of the invention as an active ingredient.

The method of treatment comprises administering an antibody or composition of the invention to a subject. The method of treatment also comprises administration an antibody or composition of the invention to a subject in parallel to, prior to, or following treatment with an additional active composition comprising cytokines such as IL-1 (interleukin-1), IL -2, IL -6 and IFN-α (interferon-α) or other antibodies, such as any T-cell stimulatory antibody or other anti-tumor therapeutic antibody. In one embodiment, the subject is a human. In another embodiment the disease to be prevented, treated or detected is cancer.

The administration of said compositions can be typically achieved by means of parenteral administration, e.g., intravenously (i.v.) intraperitoneally (i.p.) or intramuscularly (i.m.). Methods of treatment may comprise pharmaceutical compositions of the antibodies according to the invention. Alternatively or additionally, methods of treatment may include cell therapy, ex-vivo or in-vivo wherein cells are autologous or allogeneic.

In order to boost the anti-tumor activity of the antibody, it is at times advantageous to administer the antibody of the invention together with, prior to, or following, the administration of other agents, which can act in an additive or synergistic manner with it. Examples comprise various cytokines, including but not limited to IL-1 (Interleuken-1), IL-2, IL-6 and IFN-α (Interferon-α), as well as cell vaccines or additional antibodies, including but not limited to T-cell stimulatory antibodies, or anti-tumor therapeutic antibodies.

The antibody of the invention may be useful in the therapy of a variety of diseases other than cancer where activation or other effects of the antibody on the immune system's proliferative, cytolytic or stimulatory activity may have a therapeutic effect, such as, for example, in early stages of HIV infection or in patients whose blood count shows a decrease in CD4+ T cells (the causative virus of AIDS, Acquired Immune Deficiency Syndrome), in various autoimmune disorders, or in some cases of genetic or acquired immune deficiencies. In AIDS patients, the antibody may be administered to infected individuals, which have not yet developed any symptoms of the disease, or in individuals at early stages of the HIV infection process.

The dose of the antibody or composition to be administrated to a subject, in the context of the present invention should be sufficient to effect a beneficial therapeutic response in the subject over time, or to inhibit tumor growth. Thus, the antibody or composition may be administered to a subject in an amount sufficient to alleviate, reduce, cure or at least partially arrest the disease.

The dose will be determined by the activity of the therapeutic composition produced and the condition of the subject, as well as the body weight or surface area of the subject to be treated. The size of the dose and the dosing regiment also will be determined by the existence, nature, and extent of any adverse side effects that accompany the administration of a particular therapeutic composition in a particular subject. In determining the effective amount of the therapeutic composition to be administered, the physician needs to evaluate circulating plasma levels, toxicity, and progression of the disease.

EXAMPLES

Having now generally described the invention, the same will be more readily understood through reference to the following examples, which are provided by way of illustration and are not intended to be limiting of the present invention.

Example 1

Sequence Analysis of the Mouse BAT-1 Kappa Light Chain Variable Region ($V_\kappa$)

The DNA and amino acid sequences of the BAT-1 $V_\kappa$ region is shown in FIG. 1. The amino acid sequences were compared with other mouse variable regions and also with the consensus sequences of the subgroups that the variable regions were subdivided into in the Kabat database (Kabat et al., ibid). From this analysis the BAT-1 $V_\kappa$ region was found to most closely match the consensus sequences of both mouse kappa subgroup IV (Identity=88.38%; Similarity=92.45) and mouse kappa subgroup VI (Identity=87.74%; Similarity=89.62). When only the FRs of the BAT-1 kappa light chain variable region (i.e. without the amino acids in the CDRs) were compared to mouse subgroups IV and VI, percentage identity increased to exactly 90.00% for both, while percentage similarity rose to 92.50%, again for both consensus sequences. However, despite the close similarities to both Kabat subgroups, it was decided that the murine BAT-1 $V_\kappa$ region should be classed as mouse subgroup VI.

The reason for the selection of mouse subgroup VI was related to the canonical classes of the hypervariable loops of the BAT-1 $V_\kappa$ region, as defined by Chothia and his co-workers (Chothia et al., J. Mol. Biol. 196:901, 1987; Nature 34:877, 1989; J. Mol. Biol. 227:799, 1992; Tramontano et al., ibid). According to Chothia, each of the CDRs: CDR1 (L1), CDR2 (L2) and CDR3 (L3), were canonical class 1 (FIG. 2). Crucially, the 10 amino acid canonical class 1 L1 hypervariable loop was only seen in mouse $V_\kappa$ regions which fitted Kabat subgroup VI.

Most restrictive canonical classes for the CDR related loops structures have more recently been defined by Martin and Thornton (Martin et al, ibid) and these too are described in FIG. 2. The utility of these new canonical class definitions lies in their stringency, which in turn is related to the presence of a greater number of so-called framework canonical residues in each class. The importance of these "extra", potentially key, residues was later considered when designing the humanized BAT-1 antibody. Loops L1 and L2 were easily assigned to Martins canonical classes 1/10A and 1/7A, respectively, however, the L3 loop did not perfectly match any of the classes available to it. The class that it most closely matched was class 1/9A, however, to fit this class there had to be residue at position 28 in the $V_\kappa$ region of BAT-1, which is not actually present. The closest mouse kappa light chain variable region germline gene to BAT-1 $V_\kappa$ was H4, which also contained a 10 amino acid L1 loop (Table 1). Only 12 mismatches were found between the H4 germline sequence and the BAT-1 $V_\kappa$ region. The majority of these mismatches were positioned in the CDRs with only four differences located in the FRs. Most of these mismatches were highly conservative changes, except for the cysteine at position 72 (Kabat numbering) in FR3. Its location immediately adjacent to an important canonical residue (position 71) suggested that the cysteine may have a key role in antigen binding. Nevertheless, taken together, the above example clearly suggested that the BAT-1 sequence was typical of a mouse $V_\kappa$ variable region.

TABLE 1

| Seq. Name | Seq. ID NO | [1]Id. Res | [2]Residues 1-50 of murine BAT Vκ Vs. mouse germline Vκ |
|---|---|---|---|
| BAT | 94 | 106 | QIVLTQSPAIMSASPGEKVTITCSARS------SVSYMHWQQKPGTSPKL |
| H4 | 95 | 83 | .....................S...S.............Y.Y.....S... |
| H3/Ox1 | 96 | 83 | ...................M....S...........Y...S..... |
| R9 | 97 | 83 | ...................M....S..........I.....Y......... |
| H13 | 98 | 81 | .........L.........M....S.............Y.Y....RS... |
| H8 | 99 | 81 | .........L.........M....S.............X.......S... |
| H1 | 100 | 81 | ...................M......S.....V.S..LY.Y.....S... |
| H9 | 101 | 81 | ..L................M....S.............Y.....S... |
| R2 | 102 | 76 | E.L.......IA.............S............N.Y.....S... |
| T3B | 103 | 75 | ---.......A..L.....M....S.S.....V.S..L..Y...S...... |
| R11 | 104 | 74 | EN.........A........M....S.S.....V.S.NL..Y...S...T. |
| H6/X24 | 105 | 74 | E.........TA..L.Q........S................Y...S..... |
| L8 | 106 | 74 | EN.........A..L.....M....S.S.....V.S..L..Y...S...... |
| R1/s107b | 107 | 72 | EN.........A..L.Q...M....S.S.....V.S..L..Y...S.A... |
| R13 | 108 | 72 | EN............L.....MS.R.S..........N..Y.Y...SDA... |
| H2 | 109 | 67 | G.......TT.T.F...N.......S..........IN.I..Y...S.NT.. |

| Seq Name | Seq. ID NO | [1]Id. Res. | Residues 51-99 of murine BAT Vκ Vs. mouse germline Vκ |
|---|---|---|---|
| BAT | 94 | 106 | WIYRTSNLASGVPARFSGSGSGTSYCLTISRMEAEDAATYYCQQRSSFP |
| H4 | 95 | 83 | PS....................S....S.............YH.Y. |
| H3/Ox1 | 96 | 83 | R...D..K................S....S.............W..N. |
| R9 | 97 | 83 | R...D..K................S....S.............H....Y. |
| H13 | 98 | 81 | P...L....................S....S.............W..N. |
| H8 | 99 | 81 | ....SI....................S....SVK...........W..S. |
| H1 | 100 | 81 | ....S....................S....S........F....Y.QY. |
| H9 | 101 | 81 | P...D.......F............S.I..S............H....Y. |
| R2 | 102 | 76 | I...GI..................FSF..NS.....V..........Y. |

TABLE 1-continued

| | | | | |
|---|---|---|---|---|
| T3B | 103 | 75 | P...G.........V...........S....S..............W..Y. | |
| R11 | 104 | 74 | F..........E...P..........S....SV............W.GY. | |
| H6/X24 | 105 | 74 | P...EI.K..................S....S.......I.....WNYPL | |
| L8 | 106 | 74 | ....G...............A.I..S....S....ND.......W.GY. | |
| R1/s107b | 107 | 72 | PL.H......................S....SV....D.......W.GY. | |
| R13 | 108 | 72 | ....Y.....P.............N..S....S..G..........FT.S. | |
| H2 | 109 | 67 | QK..K..D.P....TL..........S....SV............W.GY. | |

¹No. of identical residues to the BAT sequence.
²A dot [.] refers to a match between BAT Vκ and the mouse germline Vκ and a line [-] refers to the absence of amino acid

Example 2

Sequence Analysis of the Mouse BAT-1 Heavy Chain Variable Region

The DNA and amino acid sequences of the BAT-1 $V_H$ region is shown in FIG. 3. An analysis similar to that given in Example 1 was conducted for the BAT-1 $V_H$ region which determined that it exhibited the closest match to the consensus sequence of the mouse heavy chain miscellaneous subgroup in the Kabat database (Kabat et al., ibid). Identity between the mouse heavy chain variable region amino acid sequence of mBAT-1 and the consensus sequences of the miscellaneous subgroup was measured at 60.64% while the similarity was calculated to be 69.23%, with the next closest Kabat subgroup consensus sequences being subgroup IIa (Identity=59.83%; Similarity=66.67%). However, when only the FRs of the BAT-1 $V_H$ region was compared to mouse subgroup IIa, percentage identity decreased to 54.02% while the similarity dropped to 62.06%. Conversely, the same comparisons carried out against the mouse miscellaneous subgroup found the FRs of the BAT-1 $V_H$ region exhibited a 65.52% identity and a 74.71% similarity.

When the canonical classes of the hypervariable loops of the BAT-1 $V_H$ region, as defined by Chothia and his co-workers, were analyzed (FIG. 4) the CDR1 and CDR2 loops (H1) matched Chothia canonical class 1 loops. However, no class was assigned to the CDR3 loop structure (H3) due to the wide range of size and amino acid make-up that H3 loops can display.

Using the more stringent canonical classes for CDR loop structures defined by Martin and Thornton (Martin et al., ibid) it was a straight forward matter to determine that the H1 loop matched Martin canonical class 1/10A. However, for the H2 loop it was more difficult to assign class, although the closest Martin canonical class was Class 2/10A. Unfortunately, since the amino acid Asp53 in the H2 loop did not match the expected residues for this position (i.e. Ala, Gly, Tyr, Ser, Lys, Thr or Asn), the match was also not perfect. The closest mouse heavy chain variable region germline gene to mBAT-1 $V_H$ identified was VMS2/VGK4 (Table 2). Thus the above example clearly suggested that the mBAT-1 sequence was typical of a mouse $V_H$ variable region.

TABLE 2

| Seq. Name/ ¹Id. Res. | Seq. ID NO | ²Residues 1-50 of murine BAT $V_H$ Vs. mouse germline $V_H$ |
|---|---|---|
| BAT/117 | 110 | QIQLVQSGPELKKPGETVKISCKASGYTFTNYGMN-WVKQAPGKGLKWMG |
| VMS2/VGK4/92 | 111 | ................................................. |
| VMS9/VGK1A/251/90 | 112 | ................................................. |
| VGK6/89 | 113 | ................................................. |
| VFM11/VGK1B/89 | 114 | ................................................. |
| 264/88 | 115 | ...........................................T...S. |
| VFM1/281/VGK7/87 | 116 | ..........................................D.S.H.. |
| VMS1/141/VGK3/84 | 117 | ............................................A.H.. |
| 161/84 | 118 | ................................................. |

TABLE 2-continued

| Seq. Name/¹Id. Res. | Seq ID NO | ²Residues 51-101 of murine BAT V_H Vs. mouse germline V_H |
|---|---|---|
| VGK5/79 | 119 | --........................TA..Q....QKM.......I. |
| VGK2/77 | 120 | ---.............R.......TA..Q....QKM.......I. |
| V104A/VAR104A/57 | 121 | .V..Q......VR..TS..........LT.W.......XM..Q..E.I. |
| VH105/57 | 122 | .V..Q......V...AS..........S.YIH......R..Q..E.I. |
| VAR104/56 | 123 | .V..Q......VR..TS..........LT.W.......XR.AQ..E.I. |
| J558-43y/56 | 124 | .V..Q......V...AS.R........S.NIH......R..Q..E.I. |
| J558-122B/55 | 125 | .V..Q......VR..TS..........IT.W.......XR..Q.XE.I. |
| 37A11/55 | 126 | .V..L...A..M...AS......T....SS.WIE......R..H..E.I. |
| VH104A/55 | 127 | .V..Q......VR..TS..........LT.W.......XM..Q..E.I. |
| VAR100/54 | 128 | .V..Q......VR..LS..L.......I.IT.W.......R..Q..E.I. |

| Seq. Name/¹Id. Res. | Seq ID NO | ²Residues 51-101 of murine BAT V_H Vs. mouse germline V_H |
|---|---|---|
| BAT/117 | 110 | WINTDSG--ESTYAEEFKGRFAFSLETSANTAYLQINNLNNEDTATYFCVR |
| VMS2/VGK4/92 | 111 | ....NT....P.................S.........K........A. |
| VMS9/VGK1A/251/90 | 112 | ....YT....P...DD..............S.........K........A. |
| VGK6/89 | 113 | ....ET....P...DD..............S.........K........-- |
| VFM11/VGK1B/89 | 114 | ....YT....P...DD..............S.........K...M....A. |
| 264/88 | 115 | ....Y....VP...DD..............S.........K........A. |
| VFM1/281/VGK7/87 | 116 | ....ET....P...DD..............S.........K........A. |
| VMS1/141/VGK3/84 | 117 | .KY.NT....P..GDD..............S.........K...M....A. |
| 161/84 | 118 | ....YT....P...DD..........C.S.........K.Q....----- |
| VGK5/79 | 119 | ....H....VPK...D...............S.........K...M.....-- |
| VGK2/77 | 120 | ....H....VPK...D...............S......S..K........-- |
| V104A/VAR104A/57 | 121 | Q.FPA....STN.N.M...KATLTVD..SS...M.LSS.TS...S.V...A. |
| VH105/57 | 122 | Y.YPRD...STN.N.K...KATLTAD..SS...M.LSS.TS...S.V...A. |
| VAR104/56 | 123 | Q.FPA....STN.N.M...KATLTVD..SS...M.LSS.TS........A. |
| J558-43y/56 | 124 | ..YPGD...NTK.N.K...KTTLTADK.SS...M.LSS.TS...S.V...A. |
| J558-122B/55 | 125 | Q.FPA....STN.N.M...KATLTVD..SS...M.LSS.TS...S.VH..A. |
| 37A11/55 | 126 | K.LPG....STN.N.K...KAK.TADI.S....M.LSS.TS...S.V.Y.A. |
| VH104A/55 | 127 | A.FPAG...STN.NQM...KATLTVD..SS...M.LSS.TS...S.V...A. |
| VAR100/54 | 128 | Q.FPA....STN.N.M.E.KATLTVD..SS...M.LSS.TS...S.V.Y.A. |

¹No. of identical residues to the BAT sequence.
²A dot [.] refers to a match between BAT V_H and the mouse germline V_H and a line [-] refers to the absence of amino acid

Example 3

Design of the Humanized BAT-1 $V_\kappa$ Antibody Variants

The first step in the design of the humanized variable regions of the BAT-1 antibody was the selection of the human kappa light chain variable region that would serve as the basis of the humanized BAT-1 $V_\kappa$ region. As an aid to this process the BAT-1 $V_\kappa$ region was initially compared to the consensus sequences of the four human kappa light chain variable region subgroups as defined by Kabat and his coworkers (Kabat et al., ibid).

The mouse BAT-1 light chain variable region was most similar to the consensus sequences of human kappa light chain subgroup I and human kappa light chain subgroup III. In the case of human kappa light chain subgroup I the mouse BAT-1 $V_\kappa$ region displayed a 63.21% identity over the whole variable region and a 70.00% identity within the FRs alone. When measured with respect to similarity, these values increased to 71.70% overall and 80.00% within the FRs alone. In the case of human kappa light chain subgroup III the mouse BAT-1 $V_\kappa$ region displayed a 65.09% identity over the whole variable region and a 68.75% identity within the FRs alone. When measured with respect to similarity, these values increased to 74.53% overall and 80.00% within the FRs alone. Consequently, it generally appeared to match well a broad range of human kappa light chain variable region sequences, however, with respect to FRs in particular, it was marginally more identical to those found within human kappa light chain subgroup I.

The mouse BAT-1 $V_\kappa$ region was then compared to all the recorded examples of individual sequences of human variable regions publicly available. Table 3 shows the best fifteen matches to the mouse BAT-1 $V_\kappa$ region which were identified through this analysis. Overall, the search algorithm selected the human $V_\kappa$ region from antibody TEL9 (Marks et al., J. Mol. Biol. 222:581, 1991) as the closest match to the mouse BAT-1 $V_\kappa$ region (Table 4). This human sequence had an overall identity to the BAT-1 $V_\kappa$ region of 67.93% overall and 72.50% within the FRs alone. When measured with respect to similarity, these values increased to 77.36% overall and 82.50% within the FRs alone. Consequently, the TEL9 kappa light chain variable region FR was selected as the human acceptor sequence for the humanization of the BAT-1 antibody kappa light chain variable region. This then became the basis of the first humanized version of the BAT-1 kappa light chain (BATRκ$_4$), which essentially comprised the CDRs of the BAT-1 $V_\kappa$ region and the FRs of the TEL9 $V_\kappa$ region.

The next step in the design process was to study the amino acid sequences of the human acceptor TEL9 $V_\kappa$ region FRs to determine if any of these amino acid residues were likely to adversely influence binding to antigen, either directly through interactions with antigen, or indirectly by altering the conformation or orientation of the CDR loops. This was a difficult process which was only made possible through the availability of a model of the BAT-1 variable regions i.e. both the $V_\kappa$ and $V_H$ regions. The modeling procedure will be given in detail in Example 5. Nevertheless, any amino acid in the mouse BAT-1 FRs which did appear to affect antigen binding were then considered for conservation in the humanized BAT-1 antibody. In deciding which murine residues to conserve the following points were addressed:

TABLE 3

| Name | SEQ ID NO | [1]ID | [2]MURINE BAT Vκ VS. MOST HOMOLOGUES 15 HUMAN Vκ | |
|---|---|---|---|---|
| RESIDUES 1-36 | 129 | | [3]sCSCCcccsCccccsccsCCCsCssscscsssssccccCC<br>             1           2           3<br>0123456789012345678901234567ABCDEF890123456<br>[4]=======L1========vv<br> v  v | |
| BAT | 129 | 100 | -QIVLTQSPAIMSASPGEKVTITCSARS-------SVSYMWF | |
| TEL9 | 130 | 64.8 | .E......SSL...V.DR.....R.SQ | _SISN.LN.Y |
| V1clone47 | 131 | 63.3 | D...M....SSL...V.DR.....R.SQ | SIS..LN.Y |
| SiP055 | 132 | 63.3 | E........TL.L....RA.LS.R.SQ | _SVS_.LA.Y |
| 039741 | 133 | 63.9 | E........TL.L....RA.LS.R.SQ | _SVS_.LA.Y |
| AC32 | 134 | 63.9 | E........TL.L....RA.LS.R.SQ | _SVS_.LA.Y |
| AC21B | 135 | 64.5 | E........TL.L....RA.LS.R.SQ | _SVS_.LA.Y |
| B9601(Vg-Jk2) | 136 | 62.7 | E........TL.L....RA.LS.R.SQ | _SVS_.LA.Y |
| LS1 | 137 | 62.4 | E........TL.L....RA.LS.R.SQ | _SVS_.LA.Y |
| TR1.21 | 138 | 63.0 | EL.M....SSL...V.DR.....R.SQ | SIS..LN.Y |
| AC18 | 139 | 63.0 | E........TL.L....RA.LS.R.SQ | _SVSG.LA.Y |
| 19.E7 | 140 | 63.6 | E........TL.L....RA.LS.R.SQ | _SVS_.LA.Y |
| STRAb SA-1A | 141 | 63.0 | D.QM....SSL...V.DR.....R.SQ | SIS..LN.Y |
| V1clone49 | 142 | 62.4 | D...M....SSL...V.DR.....R.SQ | SIS..LN.Y |
| MP6 | 143 | 62.4 | D.QM....SSL...V.DR.....R.SQ | SIS..LN.Y |
| AC33 | 144 | 63.6 | E........TL.L....RA.LS.R.SQ | _SVG_SLA.Y |
| Residues 37-80 | | | cccsccCsCCCCcccsccsSCCScCCCCCSCCSCccccccccs<br>      4         5         6         7         8<br>78901234567890123456789012345678901234567890<br>vvvv==L2===    v v vv v | |
| BAT | | 100 | QQKPGTSPKLWIYRTSNLASGVPARFSGSGSGTSYCLTISRMEA | |
| TEL9 | 130 | 64.8 | .....KA...L..AA.T.Q....S........._DFT...NSLQP | |
| V1clone47 | 131 | 63.3 | .....KA...L..AA.S.QS....S..........DFT....SLQP | |
| SiP055 | 132 | 63.3 | .....QA.R.L..DA...R.T.I......._...DFT....SL.P | |
| 039741 | 133 | 63.9 | .....QA.R.L..DA.._K.T_........_...DFT....SL.P | |
| AC32 | 134 | 63.9 | .....QA.R.L..DA...R.T.I......._...DFT....SL.P | |
| AC21B | 135 | 64.5 | .....QA.R.L..DA...R.T.I......._...DFT....SL.P | |
| B9601(Vg- | 136 | 62.7 | .....QA.R.L..DA...R.T.I......._...DFT....SL.P | |

TABLE 3-continued

| Name | SEQ ID NO | [1]ID | [2]MURINE BAT Vκ VS. MOST HOMOLOGUES 15 HUMAN Vκ |
|---|---|---|---|
| Jk2) | | | |
| LS1 | 137 | 62.4 | .R..QA.R.L..DA..R.T.I........_...DFT....SL.P |
| TR1.21 | 138 | 63.0 | .....KA...L..AA._..Q....S.........DFT....SLQP |
| AC18 | 139 | 63.0 | .....QA.R.L..D.F.R.T.I........_...DFT....SL.P |
| 19.E7 | 140 | 63.6 | .....QA.R.L..DA..R.T.I........_...DFT....SL.P |
| STRAb SA-1A | 141 | 63.0 | .....KA...L..AA.S.Q....S.........DFT....SLQP |
| V1clone49 | 142 | 62.4 | .....KA...L..AA.S.Q....S.........DFT....SLQP |
| MP6 | 143 | 62.4 | .....KA...L..AA.S.Q....S.........DFT....SLQP |
| AC33 | 144 | 63.6 | .....QA.R.LV.D...R.T.I........_...DFT....SL.P |

```
RESIDUES                sccccccCCccccc      ccccCcsccccc
81-107                         9                 10
                    123456789012345ABCDEF67890123456A7
                             =======L3=======v
```

| Name | SEQ ID NO | | |
|---|---|---|---|
| BAT | 129 | 100 | EDAATYYCQ QRSSFP------LTFGSGTKLEI-K |
| TEL9 | 130 | 64.8 | ..F......_TN_... .....G......_. |
| V1clone47 | 131 | 63.3 | ..F....._SY.T. .....G...V..._. |
| SiP055 | 132 | 63.3 | ..F.V.......NW. R...Q......_. |
| 039741 | 133 | 63.9 | ..F.V.....S_KW. .....G...V..._. |
| AC32 | 134 | 63.9 | ..F.V.......NW.P .....G...V._. |
| AC21B | 135 | 64.5 | ..F.V.......NW. .....G...V..._. |
| B9601(Vg-Jk2) | 136 | 62.7 | ..F.V.......NW.P Y...Q......_. |
| LS1 | 137 | 62.4 | ..F.V.......NW. .....G...V..._. |
| TR1.21 | 138 | 63.0 | ..F....._SY.T. F...G...V..._. |
| AC18 | 139 | 63.0 | ..F.V.....Y.W.P .....G...V._. |
| 19.E7 | 140 | 63.6 | ..F.V.......NW. .....P...VD._. |
| STRAb SA-1A | 141 | 63.0 | ..F....._SY.T. .....G...V..._. |
| V1clone49 | 142 | 62.4 | ..F....._SY.T. R...Q...V..._. |
| MP6 | 143 | 62.4 | ..F....._SY_P_PV Y...Q......_. |
| AC33 | 144 | 63.6 | ..F_D......._EW. .....G...V..._. |

[1]ID - percentage identity of the human Vκ sequences to the murine BAT Vκ region
[2]A dot [.] refers to a match between BAT Vκ and the mouse germline Vκ, a line [-] refers to the absence of amino acid, underlined residues in the human Vκ sequences differ from their closest human Vκ gene
[3]S/C refers to amino acids positioned within 5Å of a CDR on the Surface or Core of Fv and s/c to amino acids positioned further away than 5Å of a CDR on the surface or core of Fv
[4]v refers to Vernier residues (Footer et al., J. Mol. Biol. 224:487, 1992) located in the FRs

TABLE 4

| Name | SEQ ID NO | [1]ID | [2]All | [3]Surface | Core | [4]Kabat CDR | [5]FR | [3]FR Surface | [4]FR Core | [6]FR near CDR |
|---|---|---|---|---|---|---|---|---|---|---|
| BAT Vκ | 129 | 100.0 | 106 | 23 | 81 | 26 | 80 | 17 | 63 | 32 |
| TEL9 | 130 | 64.8 | 70 | 11 | 59 | 13 | 58 | 10 | 50 | 26 |
| VI clone47 | 131 | 63.3 | 69 | 11 | 59 | 13 | 57 | 10 | 50 | 26 |
| SiP055 | 132 | 63.3 | 69 | 11 | 59 | 13 | 57 | 10 | 50 | 26 |
| 039741 | 133 | 63.9 | 69 | 11 | 59 | 13 | 57 | 10 | 50 | 26 |
| AC32 | 134 | 63.9 | 69 | 11 | 59 | 13 | 57 | 10 | 50 | 26 |
| AC21B | 135 | 64.5 | 69 | 11 | 59 | 13 | 57 | 10 | 50 | 26 |
| B9601 (Vg-Jk2) | 136 | 62.7 | 69 | 11 | 59 | 13 | 57 | 10 | 50 | 26 |
| LS1 | 137 | 62.4 | 68 | 11 | 59 | 13 | 57 | 10 | 50 | 26 |
| TR1.21 | 138 | 63.0 | 68 | 11 | 58 | 13 | 57 | 10 | 50 | 26 |
| AC18 | 139 | 63.0 | 68 | 11 | 58 | 13 | 57 | 10 | 50 | 26 |
| 19.E7 | 140 | 63.6 | 68 | 11 | 58 | 12 | 57 | 10 | 50 | 26 |
| STRAb SA-1A | 141 | 63.0 | 68 | 11 | 58 | 12 | 57 | 10 | 49 | 26 |
| VIclone49 | 142 | 62.4 | 68 | 11 | 58 | 12 | 57 | 10 | 49 | 26 |
| MP6 | 143 | 62.4 | 68 | 11 | 58 | 12 | 57 | 10 | 49 | 25 |
| AC33 | 144 | 63.6 | 68 | 11 | 58 | 12 | 57 | 10 | 49 | 25 |

| Name | SEQ ID NO | [7]Vernier | [8]Vκ | [8]J | Close Human Germline | [9]L1 Size | L2 Size | L3 Size | [10]L1 Class | L2 Class | L3 Class |
|---|---|---|---|---|---|---|---|---|---|---|---|
| BAT Vκ | 129 | 14 | 94 | 12 | | 10 | 7 | 9 | ? | 1/7A | ? |
| TEL9 | 130 | 12 | 60 | 10 | DPK8-Vd+ | 11 | Same | Same | 2/11A | Same | ? |
| VIclone47 | 131 | 12 | 60 | 10 | V3b+ | 11 | Same | Same | 2/11A | Same | 1/9A |
| SiP055 | 132 | 12 | 60 | 10 | 3A7 | 11 | Same | Same | 2/11A | Same | 1/9A |
| 039741 | 133 | 12 | 59 | 10 | 3A7 | | | | | | |
| AC32 | 134 | 12 | 59 | 10 | 3A7 | 11 | Same | 10 | 2/11A | Same | ? |

TABLE 4-continued

| | | | | | | | | | | | |
|---|---|---|---|---|---|---|---|---|---|---|---|
| AC21B | 135 | 12 | 59 | 10 | 3A7 | 11 | Same | Same | 2/11A | Same | 1/9A |
| B9601 (Vg-Jk2) | 136 | 12 | 59 | 10 | 3A7 | 11 | Same | 10 | 2/11A | Same | ? |
| LS1 | 137 | 12 | 59 | 10 | 3A7 | 11 | Same | Same | 2/11A | Same | 1/9A |
| TR1.21 | 138 | 12 | 59 | 10 | V3b+ | 11 | Same | Same | ? | Same | 1/9A |
| AC18 | 139 | 12 | 59 | 10 | 3A7 | 11 | Same | 10 | 2/11A | Same | ? |
| 19.E7 | 140 | 12 | 59 | 10 | 3A7 | 11 | Same | Same | 2/11A | Same | 1/9A |
| STRAb SA-1A | 141 | 12 | 59 | 10 | V3b+ | 11 | Same | Same | 2/11A | Same | 1/9A |
| VIclone49 | 142 | 12 | 59 | 10 | V3b+ | 11 | Same | Same | 2/11A | Same | 1/9A |
| MP6 | 143 | 12 | 59 | 10 | V3b+ | 11 | Same | 11 | 2/11A | Same | ? |
| AC33 | 144 | 12 | 59 | 10 | 3A7 | 11 | Same | Same | 2/11A | Same | 1/9A |

[1]ID - percentage identity of the human Vκ sequences to the murine BAT Vκ region
[2]All - number of identical residues in the whole of the human Vκ region when compared to the whole of the murine BAT Vκ region
[3]Surface (FR Surface) - number of identical (FR) residues on the surface
[4]Core (FR Core) - number of identical residues within the (FR) core of the Fv domain
[5]CDR/FR - number of identical residues within the CDRs or the FRs;
[6]FR Near CDR - represents the number of identical residues amongst the FR amino acids within 5Å of a CDR;
[7]Vernier - number of identical residues amongst the 14 Vernier amino acids (Foote et al., ibid);
[8]Vκ (J Chain) - number of identical residues within the Vκ (J Chain) gene
[9]L1 to L3 Size - number of residues in each CDR
[10]L1 to L3 Class - Canonical class of the CDR according to Martin & Thornton (Martin et al., ibid)

a. It was of great importance that the canonical structures for the hypervariable loops (Chothia et al., 1987, 1989, 1992 ibid; Tramontano et al., ibid) were conserved. Consequently, it was crucial to conserve in the humanized BAT-1 variable regions all the mouse FR residues that were part of these canonical structures.

b. The sequences of the mBAT-1 antibody variable regions were compared to similar sequences from other mouse antibodies to identify unusual or rare residues—which may have indicated an important role in antigen binding. This was then investigated using the model of the BAT-1 variable region genes.

c. A direct analysis of the model was also made to try and predict whether any of the other mouse FR residues not present in the humanized FRs could influence antigen binding in some way.

d. Comparisons of the individual human acceptor sequences for the kappa light and heavy chain variable regions to the consensus sequence of human variable regions subgroups to which the acceptor sequences belonged were also made. The identification of any idiosyncratic amino acids in the human donor sequences was important as these could have adversely affected antigen binding.

e. Since the human light and heavy chain variable regions selected would be derived from two different human antibodies (see Example 4 for the selection of the human $V_H$ acceptor sequence), a careful analysis of the interdomain packing residues of both the donor and acceptor kappa light variable regions should be carried out. This was because any miss-packing in this region could have had a dramatic affect upon antigen binding, irrespective of the conformation of the CDR loop structures of the humanized BAT-1 antibody.

f. By following this design process, a number of amino acids in the murine BAT-1 $V_κ$ FRs were identified for conservation in the second version (BATRκ$_B$) of the humanized BAT-1 antibody (Table 5). Table 5 provides alignment of amino acid sequences leading to the design of the first (BATRκ$_A$) and second (BATRκ$_B$) reshaped human versions of the BAT-1 antibody kappa light chain variable region. There were 21 amino acid differences between the FRs of the donor mouse BAT-1 $V_κ$ region and the acceptor human TEL9 $V_κ$ region. However, there were only five residues in the humanized FRs where it was considered necessary to change the amino acid present in the human FRs to the amino acid present in the original mouse FRs.

The $V_κ$ region amino acids, located at the $V_κ/V_H$ interface as defined by Chothia and colleagues (Chothia et al., J. Mol. Biol. 186:651, 1985), were checked for unusual or rare residues. From this analysis, the only residue position that raised any level of concern was the Phe at position 36 (Phe36) in FR2. Tyr (as found in TEL9) was normally seen at this position, however, in mBAT-1 Phe was present. In addition, position 36 was a recognized position for a Vernier amino acid (Foote et al., ibid). Vernier residues were thought to be important for maintaining CDR loop conformation. Moreover, Phe was not commonly seen in Kabat mouse subgroup VI (21/153) while Tyr was very commonly seen in both mouse subgroup VI (131/153) and human subgroup I (66/74) (Kabat et al., ibid). Consequently, a Tyr36Phe change was thought to be appropriate, both to mimic the interdomain packing found in BAT-1, between the two heterologous human acceptor variable regions, and also to maintain CDR loop conformation.

TABLE 5

| Kabat | # | FR or CDR | Mouse BAT Vκ | Mouse κ-VI | Human κ-I | Human acceptor TEL9 | Surface or Core | BAT Rκ$_A$ | BAT Rκ$_B$ | Comment |
|---|---|---|---|---|---|---|---|---|---|---|
| SEQ ID NO | | | 129 | 161 | 162 | 130 | | 15 | 16 | |
| 1 | 1 | FR1 | Q | Q | D | E | S | E | E | |
| 2 | 2 | | I | I | I* | . | C | I | I | Chothia Canonical (L1); Martin Canonical (L1/L3); Vernier |

TABLE 5-continued

| Kabat | # | FR or CDR | Mouse BAT Vκ | Mouse κ-VI | Human κ-I | Human acceptor TEL9 | Surface or Core | BAT Rκ<sub>A</sub> | BAT Rκ<sub>B</sub> | Comment |
|---|---|---|---|---|---|---|---|---|---|---|
| 3 | 3 | | *V* | V* | Q | . | S | V | V | Martin Canonical (L3); |
| 4 | 4 | | L | L* | M | . | C | L | L | Chothia Canonical (L1/L3); Martin Canonical (L1/L3); Vernier |
| 5 | 5 | | T | T | T* | . | C | T | T | |
| 6 | 6 | | Q | Q* | Q | . | c | Q | Q | |
| 7 | 7 | | S | S* | S* | . | c | S | S | |
| 8 | 8 | | P | P* | P* | . | c | P | P | |
| 9 | 9 | | A | A* | S* | S | s | <u>S</u> | <u>S</u> | |
| 10 | 10 | | I | I* | S | S | C | <u>S</u> | <u>S</u> | |
| 11 | 11 | | M | M | L | L | c | <u>L</u> | <u>L</u> | |
| 12 | 12 | | S | S | S* | . | c | S | S | |
| 13 | 13 | | A | A* | A | . | c | A | A | |
| 14 | 14 | | S | S* | S | . | c | S | S | |
| 15 | 15 | | P | P | V* | V | s | <u>V</u> | <u>V</u> | |
| 16 | 16 | | G | G* | G* | . | c | G | G | |
| 17 | 17 | | E | E | D | D | c | <u>D</u> | <u>D</u> | |
| 18 | 18 | | K | K* | R | R | s | <u>R</u> | <u>R</u> | |
| 19 | 19 | | V | V* | V | . | c | V | V | |
| 20 | 20 | | T | T* | T* | . | c | T | T | |
| 21 | 21 | | I | M | I* | . | c | I | I | |
| 22 | 22 | | T | T* | T | . | C | T | T | |
| 23 | 23 | FR1 | C | C* | C* | . | C | C | C | Martin Canonical (L1/L2) |
| 24 | 24 | CDR1 | S | S | R | R | s | S | S | |
| 25 | 25 | \| | A | A* | A | . | c | A | A | Chothia Canonical (L1); Martin Canonical (L1) |
| 26 | 26 | \| | R | S* | S | S | s | R | R | |
| 27 | 27 | \| | S | S* | Q | Q | s | S | S | |
| 27A | | \| | — | — | S | — | s | — | — | |
| 27B | | \| | — | — | L | — | c | — | — | |
| 27C | | \| | — | — | V | — | s | — | — | |
| 27D | | \| | — | — | x | — | c | — | — | |
| 27E | | \| | — | — | x | — | s | — | — | |
| 27F | | \| | — | — | — | — | s | — | — | |
| 28 | | \| | — | — | S | S | s | — | — | Martin Canonical (L3); There is no amino acid here in BAT V<sub>κ</sub> |
| 29 | 28 | \| | S | S* | I | I | s | S | S | Martin Canonical (L3) |
| 30 | 29 | \| | V | V | S | S | c | V | V | Chothia Canonical (L1); Martin Canonical (L1) |
| 31 | 30 | \| | S | S | N | N | c | S | S | Martin Canonical (L3) |
| 32 | 31 | \| | Y | Y* | Y | . | c | Y | Y | Martin Canonical (L3) |
| 33 | 32 | \| | M | M | L* | L | c | M | M | Chothia Canonical (L1); Martin Canonical (L1/L3) |
| 34 | 33 | CDR1 | H | H | A | N | c | H | H | Packing AA |
| 35 | 34 | FR2 | W | W* | W* | . | C | W | W | Martin Canonical (L1); Vernier |
| 36 | 35 | | *F* | *Y* | *Y* | *Y* | C | <u>Y</u> | *F* | Packing AA; Vernier; Mouse germline = Tyr; (Δ1) |
| 37 | 36 | | Q | Q* | Q | . | c | Q | Q | |
| 38 | 37 | | Q | Q* | Q | . | c | Q | Q | Packing AA |
| 39 | 38 | | K | K* | K | . | c | K | K | |
| 40 | 39 | | P | S | P* | . | s | P | P | |
| 41 | 40 | | G | G | G | . | s | G | G | |
| 42 | 41 | | T | T | K | K | c | <u>K</u> | <u>K</u> | Mouse germline = Ser |
| 43 | 42 | | S | S* | A | A | c | <u>A</u> | <u>A</u> | |
| 44 | 43 | | P | P* | P* | . | C | P | P | Core packing AA |
| 45 | 44 | | K | K* | K | . | s | K | K | |
| 46 | 45 | | L | R | L | . | C | L | L | Vernier; Packing AA; Mouse germline = Pro |
| 47 | 46 | | *W* | *W* | *L** | *L* | C | <u>L</u> | *W* | Vernier; (Δ2) |
| 48 | 47 | | I | I* | I* | . | C | I | I | Chothia Canonical (L2); Vernier |
| 49 | 48 | FR2 | Y | Y* | Y | . | C | | | Vernier |
| 50 | 49 | CDR2 | R | D | A | A | c | R | R | |
| 51 | 50 | \| | T | T | A | A | c | T | T | Chothia Canonical (L2) |
| 52 | 51 | \| | S | S* | S | . | c | S | S | Chothia Canonical (L2) |
| 53 | 52 | \| | N | K | S | T | s | N | N | |
| 54 | 53 | \| | L | L* | L* | . | c | L | L | |
| 55 | 54 | \| | A | A | E | Q | c | A | A | |
| 56 | 55 | CDR2 | S | S* | S' | . | s | S | S | |
| 57 | 56 | FR3 | G | G* | G* | . | S | G | G | |
| 58 | 57 | | V | V* | V | . | C | V | V | |
| 59 | 58 | | P | P* | P* | . | C | P | P | |

TABLE 5-continued

| Kabat | # | FR or CDR | Mouse BAT Vκ | Mouse κ-VI | Human κ-I | Human acceptor TEL9 | Surface or Core | BAT Rκ$_A$ | BAT Rκ$_B$ | Comment |
|---|---|---|---|---|---|---|---|---|---|---|
| 60 | 59 | | A | A | S* | S | S | S | S | |
| 61 | 60 | | R | R* | R* | . | c | R | R | |
| 62 | 61 | | F | F* | F* | . | C | F | F | |
| 63 | 62 | | S | S* | S | . | C | S | S | |
| 64 | 63 | | G | G* | G* | . | C | G | G | Chothia Canonical (L2); Vernier |
| 65 | 64 | | S | S* | S | . | C | S | S | |
| 66 | 65 | | G | G* | G* | . | C | G | G | Vernier |
| 67 | 66 | | S | S* | S | . | S | S | S | |
| 68 | 67 | | G | G* | G* | . | C | G | G | Vernier |
| 69 | 68 | | T | T | T | . | C | T | T | Vernier |
| 70 | 69 | | S | S* | D | D | S | D | D | |
| 71 | 70 | | *Y* | Y | F | F | C | F | Y | Chothia Canonical (L1); Martin Canonical (L1); Vernier; (Δ3) |
| 72 | 71 | | *C* | S* | T | T | c | T | T | Mouse germline = Ser |
| 73 | 72 | | L | L* | L | . | c | L | L | |
| 74 | 73 | | T | T* | T | . | c | T | T | |
| 75 | 74 | | I | I* | I | . | c | I | I | |
| 76 | 75 | | S | S | S | N | c | N | N | |
| 77 | 76 | | R | S | S | S | c | S | S | Mouse germline = Ser |
| 78 | 77 | | M | M | L* | L | c | L | L | |
| 79 | 78 | | E | E* | Q | Q | c | Q | Q | |
| 80 | 79 | | A | A* | P | P | s | P | P | |
| 81 | 80 | | E | E* | E | . | s | E | E | |
| 82 | 81 | | D | D* | D | . | c | D | D | |
| 83 | 82 | | A | A | F | F | c | F | F | |
| 84 | 83 | | A | A* | A* | . | c | A | A | |
| 85 | 84 | | T | T | T | . | c | T | T | |
| 86 | 85 | | Y | Y* | Y* | . | c | Y | Y | |
| 87 | 86 | | Y | Y* | Y* | . | C | Y | Y | Packing AA |
| 88 | 87 | FR3 | C | C* | C* | . | C | C | C | Martin Canonical (L3) |
| 89 | 88 | CDR3 | Q | Q | Q | . | c | Q | Q | Martin Canonical (L3); Packing AA |
| 90 | 89 | | Q | Q* | Q | . | c | Q | Q | Chothia Canonical (L3); Martin Canonical (L3) |
| 91 | 90 | | R | W | Y | T | c | R | R | Martin Canonical (L3); Packing AA |
| 92 | 91 | | S | S | N | N | c | S | S | Martin Canonical (L3) |
| 93 | 92 | | S | S | S | . | c | S | S | Martin Canonical (L3) |
| 94 | 93 | | F | N | L | . | c | F | F | Martin Canonical (L3) |
| 95 | 94 | | P | P | P | . | c | P | P | Chothia Canonical (L3); Martin Canonical (L3) |
| 95A | | | — | P | E | — | | — | — | |
| 95B | | | — | M | — | — | | — | — | |
| 95C | | | — | P | — | — | | — | — | |
| 95D | | | — | — | — | — | | — | — | |
| 95E | | | — | — | — | — | | — | — | |
| 95F | | | — | — | E | — | | — | — | |
| 96 | 95 | | L | L | W | . | c | L | L | Martin Canonical (L3); Core packing AA |
| 97 | 96 | CDR3 | T | T* | T | . | c | T | T | Martin Canonical (L3) |
| 98 | 97 | FR4 | F | F* | F* | . | C | F | F | Martin Canonical (L3); Vernier; Core packing AA. |
| 99 | 98 | | G | G* | G* | . | c | G | G | |
| 100 | 99 | | S | A | Q | G | s | G | G | |
| 101 | 100 | | G | G* | G* | . | c | | | |
| 102 | 101 | | T | T* | T* | . | c | | | |
| 103 | 102 | | K | K* | K | . | c | K | K | |
| 104 | 103 | | L | L* | V | . | c | V | V | |
| 105 | 104 | | E | E* | E | . | c | E | E | |
| 106 | 105 | | I | L* | I | . | c | I | I | |
| 106A | | | — | — | — | — | | — | — | |
| 107 | 106 | FR4 | K | K* | K | . | s | K | K | |

A second change was also decided upon at position 47 in FR2. The highly conserved Leu found in the human TEL9 kappa light chain variable region was changed to a Trp, as found in the mouse BAT-1 kappa light chain variable region. Position 47 was another recognized Vernier residue position and was also located near the V$_H$ interface according to the molecular model. In particular, it was close to Ala55 in H2 and may have been interacting with it. Therefore, although Trp was never seen at this core residue position in human V$_H$ sequences, it was felt prudent to conserve it in BATRκ$_B$ by making the Leu47Trp modification.

The third FR change introduced into BATRκ$_B$ was located at position 71, which as well as being identified as a Vernier residue position (Foote et al., ibid), was also recognized as being one of the important canonical residue positions for the L1 loop structure. These canonical residues were defined by Chothia and his co-workers (Chothia et al., 1987, 1989, 1992 ibid; Tramontano et al., ibid) as being vital for the conservation of the CDR loop structure. Many of the canonical amino acids were located within the CDRs, however, a number (such as 71Tyr) were also positioned within the FRs. Although the amino acid change was conservative, the Phe71Tyr change was considered critical for the successful humanization of the BAT-1 kappa light chain.

Other versions of the humanized $V_\kappa$ region are:

BATRκ$_C$: Cys and Ser are similar in size and character, and from the model both amino acids at position 72 in FR3 appeared to be reasonably buried and pointing away from the L1 loop. However, in the case of the Cys amino acid the sulphur side-chain is exposed, according to the model, whereas according to the Kabat database (Kabat et al., ibid) the presence of Cys at this position is a unique event and Ser is commonly seen at this position (421/1234). Consequently, BATRκ$_C$ contained the changes at Tyr36Phe, Leu47Trp and Phe71Tyr (as in BATRκ$_B$) plus the Ser72Cys modification to the $V_\kappa$ FRs residues of the acceptor TEL9 antibody.

BATRκ$_D$: Evidence from the murine BAT-1 Fv model suggests that the surface exposed 69Ser is a residue which may interact with the L1 loop. In the human TEL9 kappa light chain the amino acid at this position is Asp, which is larger than Ser and positively charged. Ser is never seen at this position in human Vκ regions (Asp being by far the most common amino acid). The proximity to the L1 loop and the surface exposed nature of 69Ser tentatively suggested that it may be either interacting with L1 or even the antigen directly. Consequently, it was decided to make the Asp69Ser change in BATRκ$_D$, which was otherwise identical to BATRκ$_C$.

A description of the amino acid sequences of all the humanized BAT-1 antibody $V_\kappa$ region variants proposed above is given in FIG. 5.

Although potential N-linked glycosylation sites i.e. Asn-Xaa-(Ser/Thr)-Xaa (Gavel et al., Protein Eng. 3:43, 1990) were searched for in both the donor mouse and acceptor human $V_\kappa$ regions, as well as the humanized constructs themselves, none were identified.

Example 4

Design of the Humanized BAT-1 $V_H$ Antibody Variants

Again, the first step in the design of the humanized $V_H$ region of the mouse BAT-1 antibody was the selection of the acceptor human heavy chain variable region that would serve as the basis of the humanized BAT-1 $V_H$ region. When the mBAT-1 $V_H$ region was initially compared to the consensus sequences of the three human heavy chain variable region subgroups it was found to be most similar to the consensus sequence for human heavy chain subgroup I with a 61.54% identity overall and a 67.82% identity between the FRs alone. When measured with respect to similarity, these values also increased to 70.09% overall and 77.01% within the FRs alone.

TABLE 6

| Name | SEQ ID NO | ID | Murine BAT V11 Vs.most homologues 15 human VH |
|---|---|---|---|
| Residues 1-43 | | | scsCccccscScssccccsccCccccCSCCs  ccccCCCccsss<br>         1           2           3            4<br>12345678901234567890123456789012345AB67890123<br>  v                 -vvvv===H1== |
| BAT | 145 | 100 | QIQLVQSGPELKKPGETVKISCKASGYTFTNYGMN--WVKQAPG |
| hsighv1295 | 146 | 65.0 | .V......S......AS._......._S_SSHAI. ..R.... |
| R2C5H | 147 | 60.3 | .V......S......AS._......._N._ST.AL. _MRR... |
| 030805 | 148 | 56.8 | .V......A.V....AS..V..........S.DI. ..R..T. |
| WIL2 | 149 | 57.7 | .V......A.V....AS..V._E.._V...GHY.H ..R.... |
| 21/28 | 150 | 59.7 | .V......A.V....AS..V..........S.A.H ..R.... |
| UC | 151 | 57.7 | .V.............AS..V._E........GHY.H ..R.... |
| 030802 | 152 | 58.2 | .V......A.V....AS..V..........S.A.H ..R.... |
| 039734 | 153 | 57.7 | .V......A.V....AS..V._E........GHY.H .._G.... |
| 030812 | 154 | 56.3 | .V.............AS..V..........S.Y.H ..R.... |
| 030810 | 155 | 57.9 | .V......A.V....AS..V..........S.Y.H ..R.... |
| 4d275a | 156 | 71.4 | .V......S......AS..V..........S.A.. .._G.... |
| 030811 | 157 | 56.0 | .V......A.V....AS..V..........S.Y.H ..R.... |
| IF10 | 158 | 59.3 | .V......A.V....AS..V..........S.DI. ..R.... |
| GD9 | 159 | 71.4 | .V......S......AS..V..........S.A.. ..R.... |
| 039232 | 160 | 59.3 | .VH.....S_F....AS..V..........SSVI. ..R.... |
| Residues 44-82 | | | cCCCCCccccsc cscccccsscssCCCCCCcSsccccccccsc<br>         5           6           7           8<br>456789012ABC3456789012345678901234567890123ABC<br> vvv=====H2=====-Kabat-  v  v  v  v   v |
| BAT | 145 | 100 | KGLKWMGWINT-DSGESTYAEEFKGRFAFSLETSANTAYLQINNL |
| hsighv1295 | 146 | 65.0 | Q._Q....... NT_SP...QG.T...V...D...VS......TS_ |
| R2C5H | 147 | 60.3 | Q._.......L NT.NP...QD.T...V...D._V._F...SS_ |
| 030805 | 148 | 56.8 | Q..E....M.P N...NTG..QK.Q..VTMTRN..IS...MELSS. |
| WIL2 | 149 | 57.7 | Q..E......P N..GTN._.K.Q_.VTITRD..I....MELSR. |
| 21/28 | 150 | 59.7 | QR.E......A GN.NTK.SQK.Q..VTITRD...S...MELSS. |
| UC | 151 | 57.7 | Q..E......P N..GTN..QK.Q_.VTITRD..I....MELSR. |
| 030802 | 152 | 58.2 | QR.E......A GN.NTK.SQK.Q..VTITRD...S...MELSS. |
| 039734 | 153 | 57.7 | Q..E......P N..GTN..QK.Q_.VTITRD..I....MELSR. |
| 030812 | 154 | 56.3 | Q..E...I..P SG.STS..QK.Q..VTMTRD..TS.V.MELSS. |
| 030810 | 155 | 57.9 | Q..E...I..P SG.STS..QK.Q..VTMTRD..TS.V.MELSS. |

TABLE 6-continued

```
                SEQ
Name            ID NO  ID  Murine BAT V11 Vs.most homologues 15 human VH
4d275a          156    71.4Q..E.......NT.NP...QG.T...V...D..VS......CS.
030811          157    56.0Q..E...I..P SG.STS..QK.Q..VTMTRD..TS.V.MELSS.
IF10            158    59.3Q..E....M.P N..NTG..QK.Q..VTMTRN..IS...MELSS.
GD9             159    71.4Q..E.......NT_DP...QG.T...V...D..VS......SS.
039232          160    59.3Q..E.......NT.NP...QG.T...V...D..VT_T....._.S.

Residues                    cssccccccCCCCccsscccccc cccc ccCcsccccc
83-113                               9          10                11
                       345678901234567890ABCDEFGHIJK1234567890123
                           vv========H3=========v
BAT             145    100  NNEDTATYFCVRVGYDA----------LDYWGQGTSVTVSS
hsighvl295      146    65.0TA...GM_..AKESHSSALDL     -.......L.....
R2C5H           147    60.3QA....V.Y.AKPKRGTYRRGYYYYP M.V.....T.....
030805          148    56.8RS....V.Y.A.G..VWGSYRYTA  AF.I.....M.....
WIL2            149    57.7RSD...V.Y.A.AS.CGYDCYY    FF.......L.....
21/28           150    59.7RS....V.Y.A.G..YGSGS      -N.......L.....
UC              151    57.7RSD...V.Y.A.AS.CGYDCYY    FF.......L.....
030802          152    58.2RS....V.Y.A..KWEQPIDAP    F........L.....
039734          153    57.7RSD...V.Y.A.AS.CGYDCYYF   F........L.....
030812          154    56.3RS....V.Y.A.D..YYDSNGYYSG YF.......L.....
030810          155    57.9RS....V.Y.A..QWLGLTGPN    -........L.....
4d275a          156    71.4KA....V.Y.A.-----        ---------------
030811          157    56.0RS....V.Y.A.D.IVVVPAAIPH  YF.......L.....
IF10            158    59.3RS....V.Y.A.NNGSY         YF.......L.....
GD9             159    71.4KA....V.Y.A.-----        ---------------
039232          160    59.3KA....V.Y.A.ELRNDHYVWXNYRPPLS-....---------
```

The mouse BAT-1 $V_H$ region was then compared to all the recorded examples of individual sequences of human variable regions publicly available. Tables 6 and 7 show the best fifteen matches to the mouse BAT-1 $V_H$ region which were identified through this analysis. Overall, the search algorithm selected the human $V_H$ region from antibody hsighv1295 (Fang et al., J. Exp. Med. 179:1445, 1994) as the closest match to the mouse BAT-1 $V_H$ region. This human $V_H$ region had an overall identity to the BAT-1 $V_H$ region of 69.23% (Table 7), a value which increased to 74.71% when the FRs alone were compared. When measured with respect to similarity, these values increased to 75.21% overall and 79.31% within the FRs alone. This human FR thus became the basis of the humanized version of the BAT-1 heavy chain.

TABLE 7

| Name | SEQ ID NO | ID | All | Surface | Core | Kabat CDR | FR | FR Surface | FR Core | FR Near CDR |
|---|---|---|---|---|---|---|---|---|---|---|
| BAT $V_H$ | 145 | 100 | 117 | 26 | 86 | 30 | 87 | 18 | 68 | 27 |
| Hsighvl295 | 146 | 65.0 | 78 | 17 | 63 | 17 | 65 | 14 | 51 | 22 |
| R2C5H | 147 | 60.3 | 76 | 16 | 59 | 17 | 64 | 14 | 49 | 20 |
| 030805 | 148 | 56.8 | 71 | 16 | 56 | 14 | 59 | 13 | 47 | 19 |
| WIL2 | 149 | 57.7 | 71 | 15 | 56 | 13 | 59 | 13 | 46 | 19 |
| 21/28 | 150 | 59.7 | 71 | 15 | 55 | 13 | 59 | 13 | 46 | 19 |
| UC | 151 | 57.7 | 71 | 15 | 55 | 13 | 59 | 13 | 46 | 19 |
| 030802 | 152 | 58.2 | 71 | 15 | 55 | 13 | 59 | 13 | 46 | 19 |
| 039734 | 153 | 57.7 | 71 | 15 | 55 | 13 | 57 | 13 | 46 | 19 |
| 030812 | 154 | 56.3 | 71 | 15 | 55 | 13 | 58 | 13 | 46 | 18 |
| 030810 | 155 | 57.9 | 70 | 15 | 55 | 13 | 58 | 13 | 46 | 17 |
| 4d275a | 156 | 71.4 | 70 | 15 | 54 | 13 | 58 | 13 | 46 | 18 |
| 030811 | 157 | 56.0 | 70 | 15 | 54 | 13 | 58 | 13 | 46 | 18 |
| IF10 | 158 | 59.3 | 70 | 15 | 54 | 13 | 58 | 13 | 46 | 18 |
| GD9 | 159 | 71.4 | 70 | 15 | 54 | 11 | 58 | 13 | 46 | 18 |
| 039232 | 160 | 59.3 | 70 | 15 | 54 | 13 | 58 | 13 | 46 | 18 |

| Name | SEQ ID NO | Vernier | $V_H$ | J | Close Human Germline | H1 Size | H2 Size | H3 Size | H1 Class | H2 Class |
|---|---|---|---|---|---|---|---|---|---|---|
| BAT $V_H$ | 145 | 16 | 98 | 19 | | 5 | 17 | 8 | ? | ? |
| Hsighvl295 | 146 | 13 | 70 | 14 | VI-4.1b+ | Same | Same | 11 | 1/10A | 2/10A |
| R2C5H | 147 | 13 | 70 | 14 | VI-4.1b+ | Same | Same | 17 | Same | Same |
| 030805 | 148 | 11 | 66 | 14 | DP-15-V18+ | | | | | |

TABLE 7-continued

| | | | | | | | | | | | |
|---|---|---|---|---|---|---|---|---|---|---|---|
| WIL2 | 149 | 11 | 65 | 14 | DP-8+ | Same | Same | 14 | 1/10A | Same |
| 21/28 | 150 | 11 | 64 | 14 | DP-25-VI3b+ | Same | Same | 10 | 1/10A | Same |
| UC | 151 | 11 | 62 | 14 | DP-8+ | Same | Same | 14 | 1/10A | Same |
| 030802 | 152 | 11 | 62 | 14 | DP-25-VI3b+ | | | | | |
| 039734 | 153 | 11 | 62 | 14 | DP-8+ | | | | | |
| 030812 | 154 | 11 | 60 | 14 | hv1fl0t | | | | | |
| 030810 | 155 | 11 | 59 | 14 | hv1fl0t | | | | | |
| 4d275a | 156 | 11 | 59 | 14 | DP-21-4d275a+ | Same | Same | 0 | Same | Same |
| 030811 | 157 | 11 | 59 | 14 | hv1fl0t | | | | | |
| IF10 | 158 | 11 | 59 | 14 | DP-15-V18+ | Same | Same | 9 | Same | Same |
| GD9 | 159 | 11 | 58 | 14 | VI-4.1b+ | Same | Same | 0 | Same | 2/10A |
| 039232 | 160 | 11 | 58 | 14 | VI-4.1b+ | | | | | |

[1] ID—percentage identity of the human $V_H$ sequences to the murine BAT $V_H$ region
[2] All—number of identical residues in the whole of the human $V_H$ region when compared to the whole of the murine BAT $V_H$ region
[3] Surface (FR Surface)—number of identical (FR) residues on the surface
[4] Core (FR Core)—number of identical residues within the (FR) core of the Fv domain
[5] CDR/FR—number of identical residues within the CDRs or the FRs;
[6] FR Near CDR—represents the number of identical residues amongst the FR amino acids within 5Å of a CDR;
[7] Vernier—number of identical residues amongst the 14 Vernier amino acids (Foote et al., ibid);
[8] $V_H$ (J Chain)—number of identical residues within the $V_H$ (J Chain) gene
[9] L1 to L3 Size—number of residues in each CDR
[10] L1 to L3 Class—Canonical class of the CDR according to Martin & Thornton (Martin et al., ibid)

The next step in the design process was to study the amino acid sequences of the human acceptor hsighv1295 $V_H$ region FRs to determine if any of these amino acid residues were likely adversely influence binding to antigen. Once again, the molecular models built by OML (see Example 5) were crucial to this design process, from which a number of amino acids in the murine BAT-1 $V_H$ region FRs were identified for conservation in the first (BATRH$_A$) and subsequent versions of the humanized BAT-1 antibody (Table 8). There were 22 amino acid differences between the FRs of the donor mouse BAT-1 and the acceptor human hsighv1295 $V_H$ regions and up to nine murine residues were considered for conservation in the humanized FRs.

BATRH$_A$ therefore consisted of the CDRs of the mouse BAT-1 antibody $V_H$ region genetically inserted into the FRs of the human hsighv1295 antibody $V_H$ region. This was the CDR-grafted version of the $V_H$ region of the humanized BAT-1 antibody and contained no FR amino acid changes whatsoever.

In BATRH$_B$, the amino acids at positions 28 and 30 in FR1 of the mouse BAT-1 sequence (i.e. Thr and Thr, respectively) replaced the corresponding human hsighv1295 amino acids (i.e. Ser, and Ser, respectively) in the humanized BAT-1 heavy chain variable region. This was done because they represented some of the canonical residues important for the H1 hypervariable loop conformation (Chothia et al., 1992 ibid). Canonical residues were considered critical for the correct orientation and structure of hypervariable loops and were generally always conserved in a humanized variable region. Moreover, residue positions 27-30 were considered part of the H1 loop itself and so were even more critical to the correct conformation and orientation of this loop—justifying their conservation even more strongly. Thus, these two residue positions represented the sum of the changes made to the FRs of the human hsighv1295 sequence in BATRH$_B$.

TABLE 8

| Kabat | # | FR or CDR | Mouse BAT $V_H$ | Mouse Misc. | Human I | Human Accep. hsighv 1295 | Surf. or Core | BAT $RH_A$ | BAT $RH_B$ | BAT $RH_C$ | Comment |
|---|---|---|---|---|---|---|---|---|---|---|---|
| SEQ ID NO | | | 145 | 163 | 164 | 146 | | 20 | 21 | 22 | |
| 1 | 1 | FR1 | Q | E | Q | . | s | Q | Q | Q | |
| 2 | 2 | | I | V* | V | V | c | V | V | V | Martin Canonical (H1); Vernier |
| 3 | 3 | | Q | Q | Q | . | s | Q | Q | Q | |
| 4 | 4 | | L | L | L* | . | C | L | L | L | Martin Canonical (H1) |
| 5 | 5 | | V | Q* | V | . | c | V | V | V | |
| 6 | 6 | | Q | Q* | Q | . | c | Q | Q | Q | |
| 7 | 7 | | S | S | S* | . | c | S | S | S | |
| 8 | 8 | | G | G | G* | . | c | G | G | G | |
| 9 | 9 | | P | A* | A | S | s | S | S | S | |
| 10 | 10 | | E | E | E | . | c | E | E | E | |
| 11 | 11 | | L | L* | V | . | S | L | L | L | |
| 12 | 12 | | K | V* | K | . | c | K | K | K | |
| 13 | 13 | | K | K | K* | . | s | K | K | K | |
| 14 | 14 | | P | P* | P* | . | s | P | P | P | |
| 15 | 15 | | G | G | G* | . | c | G | G | G | |
| 16 | 16 | | E | A | A | A | c | A | A | A | |
| 17 | 17 | | T | S* | S* | S | c | S | S | S | |
| 18 | 18 | | V | V* | V | . | c | V | V | V | |
| 19 | 19 | | K | K* | K | . | s | K | K | K | |
| 20 | 20 | | I | L | V | . | c | I | I | I | Martin Canonical (H1) |
| 21 | 21 | | S | S | S | . | c | S | S | S | |
| 22 | 22 | | C | C | C* | . | C | C | C | C | Martin Canonical (H1) |
| 23 | 23 | | K | T | K | . | c | K | K | K | |
| 24 | 24 | | A | A* | A | . | c | A | A | A | Chothia Canonical (H1); Martin Canonical (H1) |
| 25 | 25 | | S | S | S* | . | c | S | S | S | |
| 26 | 26 | | G | G | G* | . | c | G | G | G | Chothia Canonical (H1); Martin Canonical (H1) |
| 27 | 27 | | Y | P* | Y | . | C | Y | Y | Y | Chothia Canonical (H1); Vernier |
| 28 | 28 | | T | N | T | S | S | S | T | T | Vernier; (Δ1) |
| 29 | 29 | | F | I* | F* | . | C | F | F | F | Chothia Canonical (H1); Martin Canonical (H1); Vernier |
| 30 | 30 | FR1 | T | K | T | S | C | S | T | T | Vernier; (Δ2) |
| 31 | 31 | CDR1 | N | D | S | S | s | N | N | N | |
| 32 | 32 | | Y | T | Y | H | c | Y | Y | Y | Martin Canonical (H1) |
| 33 | 33 | | G | Y* | A | A | c | G | G | G | Martin Canonical (H1/H2) |
| 34 | 34 | | M | M | I | I | c | M | M | M | Chothia Canonical (H1) Martin Canonical (H1) |
| 35 | 35 | | N | H | S | . | c | N | N | N | Martin Canonical (H1); Packing AA. |
| 35a | | | — | — | — | — | — | — | — | — | |
| 35b | | CDR1 | — | — | — | — | — | — | — | — | |
| 36 | 36 | FR2 | W | W | W* | . | C | W | W | W | Martin Canonical (H1) |
| 37 | 37 | | V | V* | V | . | C | V | V | V | Packing AA. |
| 38 | 38 | | K | K | R* | R | C | R | R | R | |
| 39 | 39 | | Q | Q | Q* | . | c | Q | Q | Q | Packing AA. |
| 40 | 40 | | A | R | A | . | c | A | A | A | |
| 41 | 41 | | P | P | P | . | s | P | P | P | |
| 42 | 42 | | G | E* | G* | . | s | G | G | G | |
| 43 | 43 | | K | Q* | Q | Q | s | Q | Q | Q | |
| 44 | 44 | | G | G* | G | . | c | G | G | G | |
| 45 | 45 | | L | L | L* | . | C | L | L | L | Core packing AA. |
| 46 | 46 | | K | E | E* | Q | C | Q | Q | Q | |
| 47 | 47 | | W | W | W* | . | C | W | W | W | Martin Canonical (H2); Packing AA. |
| 48 | 48 | | M | I* | M | . | C | M | M | M | Martin Canonical (H1) |
| 49 | 49 | FR2 | G | G* | G* | . | C | G | G | G | |
| 50 | 50 | CDR2 | W | R | W | . | c | W | W | W | Martin Canonical (H2) |
| 51 | 51 | | I | I | I | . | c | I | I | I | Martin Canonical (H1/H2) |
| 52 | 52 | | N | D* | N | . | c | N | N | N | Martin Canonical (H2) |
| 52a | 53 | | T | P* | P | . | c | T | T | T | Chothia Canonical (H2) Martin Canonical (H2) |
| 52b | | | — | — | Y | — | — | — | — | — | Martin Canonical (H2) |
| 52c | | | — | — | — | — | — | — | — | — | Martin Canonical (H2) |
| 53 | 54 | | D | A | G | N | s | D | D | D | Martin Canonical (H2) |
| 54 | 55 | | S | N | N | T | c | S | S | S | Martin Canonical (H2) |
| 55 | 56 | | G | G | G | . | c | G | G | G | Chothia Canonical (H2); Martin Canonical (H2) |

TABLE 8-continued

| Kabat | # | FR or CDR | Mouse BAT $V_H$ | Mouse Misc. | Human I | Human Accep. hsighv 1295 | Surf. or Core | BAT $RH_A$ | BAT $RH_B$ | BAT $RH_C$ | Comment |
|---|---|---|---|---|---|---|---|---|---|---|---|
| 56 | 57 | | E | N | D | S | s | E | E | E | Martin Canonical (H2) |
| 57 | 58 | | S | T | T | P | c | S | S | S | |
| 58 | 59 | | T | K | N | . | c | T | T | T | Martin Canonical (H2) |
| 59 | 60 | | Y | Y | Y | . | c | Y | Y | Y | Martin Canonical (H2) |
| 60 | 61 | | A | D | A | . | c | A | A | A | |
| 61 | 62 | | E | P* | Q | Q | s | E | E | E | |
| 62 | 63 | | E | K* | K | G | s | E | E | E | |
| 63 | 64 | | F | F* | F | . | c | F | F | F | |
| 64 | 65 | | K | Q* | Q | T | s | K | K | K | |
| 65 | 66 | CDR2 | G | G | G | . | s | G | G | G | |
| 66 | 67 | FR3 | R | K | R | . | C | R | R | R | |
| 67 | 68 | | F | A | V | . | C | F | F | F | |
| 68 | 69 | | A | T* | T | V | C | <u>V</u> | <u>V</u> | <u>V</u> | |
| 69 | 70 | | F | I | I | . | C | F | F | F | Martin Canonical (H1/H2) |
| 70 | 71 | | S | T* | T | . | C | S | S | S | |
| 71 | 72 | | L | A* | A | . | C | L | L | L | Chothia Canonical (H2); Martin Canonical (H2) |
| 72 | 73 | | E | D | D | D | c | <u>D</u> | <u>D</u> | <u>D</u> | |
| 73 | 74 | | T | T* | T | . | S | T | T | T | |
| 74 | 75 | | S | S* | S* | . | s | S | S | S | |
| 75 | 76 | | A | S* | T | V | c | <u>V</u> | <u>V</u> | <u>V</u> | |
| 76 | 77 | | N | N* | S | S | c | <u>S</u> | <u>S</u> | N | (Δ3) |
| 77 | 78 | | T | T* | T | . | c | T | T | T | |
| 78 | 79 | | A | A* | A | . | c | A | A | A | Martin Canonical (H1/H2) |
| 79 | 80 | | Y | Y* | Y | . | c | Y | Y | Y | |
| 80 | 81 | | L | L | M | . | c | L | L | L | Martin Canonical (H1) |
| 81 | 82 | | Q | Q* | E | . | c | Q | Q | Q | |
| 82 | 83 | | I | L* | L | . | c | I | I | I | |
| 82a | 84 | | N | S* | S | T | c | <u>T</u> | <u>T</u> | <u>T</u> | |
| 82b | 85 | | N | S* | S | S | s | <u>S</u> | <u>S</u> | <u>S</u> | |
| 82c | 86 | | L | L | L* | . | c | L | L | L | |
| 83 | 87 | | N | T* | R | T | c | <u>T</u> | <u>T</u> | <u>T</u> | |
| 84 | 88 | | N | S* | S | A | s | <u>A</u> | <u>A</u> | <u>A</u> | |
| 85 | 89 | | E | E* | E | . | s | E | E | E | |
| 86 | 90 | | D | D* | D* | . | c | D | D | D | |
| 87 | 91 | | T | T* | T | . | c | T | T | T | |
| 88 | 92 | | A | A | A | G | c | <u>G</u> | <u>G</u> | <u>G</u> | |
| 89 | 93 | | T | V | V | M | c | <u>M</u> | <u>M</u> | <u>M</u> | |
| 90 | 94 | | Y | Y | Y* | . | c | Y | Y | Y | Martin Canonical (H1) |
| 91 | 95 | | F | Y* | Y | . | C | F | F | F | Packing AA. |
| 92 | 96 | | C | C | C* | . | C | C | C | C | Martin Canonical (H1) |
| 93 | 97 | | V | A | A* | A | C | <u>V</u> | <u>V</u> | A | Packing AA; (Δ4) |
| 94 | 98 | FR3 | R | R | R | K | C | <u>R</u> | <u>R</u> | K | Chothia Canonical (H1); Martin Canonical (H1); (Δ5) |
| 95 | 99 | CDR3 | V | G | A | E | c | V | V | V | Packing AA. |
| 96 | 100 | | G | Y | P | S | c | G | G | G | |
| 97 | 101 | | Y | L | G | H | s | Y | Y | Y | |
| 98 | 102 | | D | R | Y | S | s | D | D | D | |
| 99 | 103 | | A | R | G | S | c | A | A | A | |
| 100 | | | — | D | S | A | | — | — | — | |
| 100 a | | | — | — | G | L | | — | — | — | |
| 100 b | | | — | — | G | D | | — | — | — | |
| 100 c | | | — | — | G | — | | — | — | — | |
| 100 d | | | — | — | C | — | | — | — | — | |
| 100 e | | | — | — | Y | — | | — | — | — | |
| 100 f | | | — | — | R | — | | — | — | — | |
| 100 g | | | . | — | G | — | | . | . | . | |
| 100 h | | | . | — | D | — | | . | . | . | |
| 100 i | | | . | — | Y | — | | . | . | . | |
| 100 j | | | . | — | x | — | | . | . | . | |
| 100 k | 104 | | L | — | F | . | c | L | L | L | Core packing AA. |
| 101 | 105 | | D | D | D | . | c | D | D | D | |
| 102 | 106 | CDR3 | Y | Y | Y | . | c | Y | Y | Y | Martin Canonical (H1) |
| 103 | 107 | FR4 | W | W | W* | . | C | W | W | W | Core packing AA. |
| 104 | 108 | | G | G | G | . | c | G | G | G | |
| 105 | 109 | | Q | Q | Q | . | s | Q | Q | Q | |
| 106 | 110 | | G | G | G* | . | c | G | G | G | |
| 107 | 111 | | T | T* | T | . | c | T | T | T | |
| 108 | 112 | | S | S | L | L | c | <u>L</u> | <u>L</u> | <u>L</u> | |
| 109 | 113 | | V | V | V* | . | c | V | V | V | |

TABLE 8-continued

| Kabat | # | FR or CDR | Mouse BAT $V_H$ | Mouse Misc. | Human I | Human Accep. hsighv 1295 | Surf. or Core | BAT $RH_A$ | BAT $RH_B$ | BAT $RH_C$ | Comment |
|---|---|---|---|---|---|---|---|---|---|---|---|
| 110 | 114 | I | T | T | T | . | c | T | T | T | |
| 111 | 115 | I | V | V* | V* | . | | V | V | V | |
| 112 | 116 | I | S | S | S* | . | | S | S | S | |
| 113 | 117 | FR4 | S | S | S* | . | | S | s | S | |

The third version of the humanized BAT-1 $V_H$ region (BATRH$_C$) incorporated all the substitutions made in BATRH$_B$ and, in addition contained a further three murine amino acids, which were inserted into the human FRs in place of the corresponding human residues. The first of these was the Asn amino acid located at position 76 in FR3. According to the molecular model of the BAT-1 Fv region, the Asn residue was close to CDR H1 and may have been supporting the loop structure. In addition, in the mouse BAT-1 $V_H$ region, the Asn was surface exposed and larger than the Ser in the human hsighv1295 FRs. Consequently, a Ser76Asn substitution was made to the FR.

A further change was made to the amino acid at position 94 in FR3 of the $V_H$ region, a residue position which had been previously identified by Chothia et al. (Chothia et al., 1992 ibid) as well as by Martin and Thornton (Martin et al., ibid), as important for H3 loop conformation. Moreover, the molecular model indicated that the Arg94 could form a salt bridge with Asp101 in CDR H3, stabilizing the loop structure. Consequently, the Arg in the mouse replaced the Lys in the human at this residue position. A final modification was also made at position 93 in FR3 where the human Ala was replaced by the murine Val amino acid. This residue was considered a packing residue, as defined by Chothia (Chothia et al., 1985 ibid), important for the correct packing of the $V_K$ and $V_H$ regions. In addition, this was identified as a Vernier residue position, and therefore important for maintaining CDR loop conformation, a classification confirmed by an analysis of the molecular model. Taken together, all the data and molecular analysis suggested that it was appropriate to conserve these three murine residues in the humanized $V_H$ region of BATRH$_C$, i.e. Ser76Asn, Ala93Val and Lys94Arg.

The construction of the next two humanized variants of the BAT-1 $V_H$ region depended upon the binding affinity of these first three humanized versions i.e. BATRH$_A$, BATRH$_B$ and BATRH$_C$. If all three failed to display an adequate level of binding, then versions BATRH$_D$ and BATRH$_E$ would be synthesized and tested.

Version D of the humanized BAT-1 $V_H$ region (BATRH$_D$) incorporated all the substitutions made in BATRH$_C$ and, in addition, contained one further mouse amino acid located at position 2 in FR1. This location was defined as both a canonical (Martin et al, ibid) and Vernier (Foote et al., ibid) residue position. In addition, from the model of the BAT-1 variable region, the murine Ile amino acid was close to Tyr27 in FR1, which is itself part of the H1 loop structure. Conversely, the murine Ile and human Val amino acids, at this location in the mouse and human FRs, were similar in character and only slightly different in size, i.e. Ile has an extra methyl group. Therefore, it was decided to make the Val21Ile change only at this stage of the humanization procedure and incorporate the mutation into version BATRH$_D$.

The final version of the humanized BAT-1 heavy chain variable region (BATRH$_E$) incorporated all the mouse FR substitutions made in BATRH$_D$ along with three additional amino acid changes at positions 38 (FR2), 46 (FR2) and 68 (FR3).

The Arg38Lys modification was made because the model suggested that the Arg, deeply buried in the core of the $V_H$ region, was close to Phe63 in CDR H2. However, this was not a previously identified canonical or Vernier residue position. In addition, Arg and Lys are relatively similar in structure, although Arg is bulkier, and so the significance of any amino acid change was hard to judge. Consequently, this was considered as only a tentative possibility and the substitution was only going to be made if the binding affinity of the humanized BAT-1 antibody was found to be poor. The same rationale was also behind the selection of the Gln46Lys modification. The Lys amino acid was half-buried, according to the molecular model, but close to Glu62 and Phe63 in CDR H2. There was a faint possibility that the larger, charges Lys46 residue could interact with the antigen directly, therefore it was conserved in BATRH$_E$. The case for preserving the murine 68Ala amino acid was related to its proximity to CDR H2, particularly to residue Tyr59 in the H2 loop, and to the chance of it therefore influencing loop structure. The Ala was unlikely to be important due to its small size, however the larger Val, found in the human hsighv1295 FRs could have adversely affected H2 loop structure, and so was replaced with the murine Ala residue.

A description of the amino acid sequences of all the humanized $V_H$ region variants proposed above is given in FIG. 6.

Although potential N-linked glycosylation sites i.e. Asn-Xaa-(Ser/Thr)-Xaa (Gavel et al., ibid) were searched for in both the donor mouse and acceptor human $V_H$ regions, as well as the humanized constructs themselves, none were identified.

Example 5

Molecular Modeling of the Murine and Humanized BAT-1 Fv Domain

To assist the design of the humanized variable regions of the BAT-1 antibody, a molecular model of the variable regions of both the murine and the humanized antibodies were built. The modeling of these structures was achieved using both the established methods of modeling by homology and ab initio techniques. This was done using AbM molecular modeling package, which was supplied and utilized by Oxford Molecular Limited (OML). Antibody X-ray crystallographic structures from the Brookhaven database available were formatted to allow them to be used for modeling with AbM.

The FRs of the BAT-1 variable regions were modeled on FRs from similar, structurally solved immunoglobulin variable regions. While identical amino acid side-chains were kept in their original orientation, mismatched side-chains were substituted as in the original BAT-1 Fv region. The backbone atoms of the FAB17-1A $V_\kappa$ region were used for the model of the BAT-1 $V_\kappa$ region, while the FRs of the 409.5.3 $V_H$ region were used to model the BAT-1 $V_H$ region (Brookhaven PDB codes 1for and 1iai, respectively). These sequences both represented good matches for the variable region sequences of murine BAT-1 antibody, and their humanized variants. The identities for the mBAT-1 and humanized sequences ranged from 73% to 92% for $V_\kappa$ region sequences and between 65% and 79% for $V_H$ region sequences. Testing of AbM with known structures has shown that FR backbone homology is an important factor in the quality of any model, since the use of FR structures that poorly match a sequence being modeled can significantly and adversely affect the position and orientation of the CDR loop structure.

For the backbone structure of the L1 loop, the loop conformations of the murine BAT-1 $V_\kappa$ region and the humanized BATR$\kappa_B$ sequence (FIG. 5) were taken from canonical classes used by AbM. These canonical classes are based on those described by Chothia and his colleagues, but they have been modified to take into consideration structures that have become available since the original articles were published (Chothia et al., 1987, 1989, 1992 ibid; Tramontano et al., ibid). Testing the performance of AbM predictions for known loop structures has shown that CDR loops which are created in this way are usually modeled very accurately, i.e. to within 1-1.5 Å RMS deviation. For the $V_\kappa$ region sequence BATR$\kappa_A$, the substitution of Phe for Tyr at position 71 (in FR3) meant that it no longer fitted the canonical class (Class 1) seen in the murine $V_\kappa$ region and the humanized BATR$\kappa_B$ $V_\kappa$ region. Tyr71 had an important role in the conformation of the L1 loop, however, analysis of the modeled structures suggested that it was the packing of the L1 loop against the aromatic ring of Tyr which was the key feature of the residue. Thus, there was reason to believe that Phe could also perform this function. In addition, from the models there did not seem to be any strong interactions with the hydroxyl group of Tyr71. Consequently, there was a possibility that the substitution of Tyr with Phe could well have had no affect the actual conformation of the L1 loop.

For the backbone structures of CDRs L2, L3, H1 and H2, conformations for all the models were taken from canonical classes defined by AbM without modification.

The H3 loop in the BAT-1 $V_H$ region was eight residues long, so two methods were used for predicting the H3 loop structure. A database search for the backbone conformations was used for both methods, but in addition, the conformation of the central five residues in the model were searched more thoroughly using a CONGEN search (Bruccoleri, ibid). Although this took longer to compute, it reassuringly produced a conformation which was very similar to those identified from the database search.

After adjusting the whole of the model for obvious steric clashes it was finally subjected to energy minimization, as implemented in MACROMODEL, both to relieve unfavorable atomic contacts and to optimize van der Waals and electrostatic interactions.

Example 6

Construction of Humanized BAT-1 Light Chain Variants

As with all examples, a strict PCR-cloning and sequencing protocol was followed. This was done to minimize the possibility of introducing errors into the humanized versions. The construction of the humanized BAT-1 kappa light chain variable region genes (i.e. BATR$\kappa_A$, BATR$\kappa_B$, and BATR$\kappa_D$) produced an approximately 425 bp product which was then subcloned in pCR2.1™. The PCR reactions were set up using the primers described in Tables 9 and 10.

TABLE 9

| Primer Name | SEQ ID NO | Oligonucleotide used in the construction of the various humanized versions of the BAT-1 antibody kappa light chain variable region gene (5'→ 3') |
|---|---|---|
| BATRκ.1 | 30 | CCCAAGCTTGCCGCCACCATG GACATGAGGGTCCCCGCTCAG C |
| BATRκ.2 | 31 | TCCTGGGGCTCCTGCTGCTCT GGCTCCCAGGTGCCAAATG |
| BATRκ.3 | 32 | TGAAATTGTGTTGACGCAGTC TCCATCCTCCCTGTCTGCA |
| BATRκ.4 | 33 | TCTGTAGGAGACAGAGTCACC ATCACTTGCAGTGCCAGGT |
| BATRκ.5 | 34 | CAAGTGTAAGTTACATGCACT GGTATCAGCAGAAACCAGG |
| BATRκ.6 | 35 | GAAAGCCCCTAAGCTCCTGAT CTATAGGACATCCAACCTG |
| BATRκ.7 | 36 | GCTTCTGGGGTCCCATCTAGA TTCAGCGGCAGTGGATCTG |
| BATRκ.8 | 37 | GGACAGATTTCACTCTCACCA TCAACAGCCTGCAGCCTGA |
| BATRκ.9 | 38 | AGATTTTGCAACTTACTATTG CCAGCAAAGGAGTAGTTTC |
| BATRκ.10 | 39 | CCACTCACGTTCGGCGGAGGG ACCAAGCTGGAGATCAAACGT GAGTGGATCCGCG |
| BATRK.11 | 40 | GAGCAGCAGGAGCCCCAGGAG CTGAGCGGGGACCCTCATG |
| BATRK.12 | 41 | ACTGCGTCAACACAATTTCAC ATTTGGCACCTGGGAGCCA |
| BATRK.13 | 42 | GTGACTCTGTCTCCTACAGAT GCAGACAGGGAGGATGGAG |

TABLE 9-continued

Oligonucleotide used in the construction of the various humanized versions of the BAT-1 antibody kappa light chain variable region gene (5'→ 3')

| Primer Name | SEQ ID NO | Sequence |
|---|---|---|
| BATRK.14 | 43 | GTGCATGTAACTTACACTTGACCTGGCACTGCAAGTGATG |
| BATRK.15 | 44 | TCAGGAGCTTAGGGGCTTTCCCTGGTTTCTGCTGATACCA |
| BATRK.16 | 45 | CTAGATGGGACCCCAGAAGCCAGGTTGGATGTCCTATAGA |
| BATRK.17 | 46 | GGTGAGAGTGAAATCTGTCCCAGATCCACTGCCGCTGAAT |
| BATRK.18 | 47 | AATAGTAAGTTGCAAAATCTTCAGGCTGCAGGCTGTTGAT |
| BATRK.19 | 48 | CCTCCGCCGAACGTGAGTGGGAAACTACTCCTTTGCTGGC |
| BATRK.20 | 49 | CGCGGATCCACTCACGTTTGATCTCCAGCTTGGTC |
| BATRK.5B | 50 | CAAGTGTAAGTTACATGCACTGGTTCCAGCAGAAACCAGG |
| BATRK.6B | 51 | GAAAGCCCCTAAGCTCTGGATCTATAGGACATCCAACCTG |
| BATRK.8B | 52 | GGACAGATTACACTCTCACCATCAACAGCCTGCAGCCTGA |
| BATRK.15B | 53 | TCCAGAGCTTAGGGGCTTTCCCTGGTTTCTGCTGGAACCA |
| BATRK.17B | 54 | GGTGAGAGTGTAATCTGTCCCAGATCCACTGCCGCTGAAC |
| BATRK.17D | 55 | GGTGAGACAGTAAGATGTCCCAGATCCACTGCCGCTGAAC |
| BATRK.8D | 56 | GGACATCTTACTGTCTCACCATCAACAGCCTGCAGCCTGA |

TABLE 10

| Humanized BAT-1 variant | Oligonucleotide primer[1] combinations used for the construction of the kappa light chain of each variant[2] | | | | |
|---|---|---|---|---|---|
| BATRκ_A | BATRκ.1 | BATRκ.2 | BATRκ.3 | BATRκ.4 | BATRκ.5 |
| | BATRκ.6 | BATRκ.7 | BATRκ.8 | BATRκ.9 | BATRκ.10 |
| | BATRκ.11 | BATRκ.12 | BATRκ.13 | BATRκ.14 | BATRκ.15 |
| | BATRκ.16 | BATRκ.17 | BATRκ.18 | BATRκ.19 | BATRκ.20 |
| BATRκ_B | BATRκ.1 | BATRκ.2 | BATRκ.3 | BATRκ.4 | BATRκ.5B |
| | BATRκ.6B | BATRκ.7 | BATRκ.8B | BATRκ.9 | BATRκ.10 |
| | BATRκ.11 | BATRκ.12 | BATRκ.13 | BATRκ.14 | BATRκ.15B |
| | BATRκ.16 | BATRκ.17B | BATRκ.18 | BATRκ.19 | BATRκ.20 |
| BATRκ_D | BATRκ.1 | BATRκ.2 | BATRκ.3 | BATRκ.4 | BATRκ.5B |
| | BATRκ.6B | BATRκ.7 | BATRκ.8D | BATRκ.9 | BATRκ.10 |
| | BATRκ.11 | BATRκ.12 | BATRκ.13 | BATRκ.14 | BATRκ.15B |
| | BATRκ.16 | BATRκ.17D | BATRκ.18 | BATRκ.19 | BATRκ.20 |

[1] Oligonucleotide sequences are given in Table 9.
[2] Oligonucleotide primers BATRκ.1 and BATRκ.20 were also used as the outer amplification primers.

Putative positive transformants were identified using the PCR-screening assay, restriction digest and then ds-DNA sequenced. The humanized Vκ genes (FIGS. 7-9; SEQ ID NOS. 15, 16 and 18) were then subcloned into expression plasmids.

The light chain pKN110 construct included Ampicillin and Neomycin resistance genes. The humanized $V_\kappa$ gene variants of BAT-1 (i.e. BATRκ$_A$, BATRκ$_B$ and BATRκ$_D$) were inserted between the HCMV Immediate Early Promoter and the genomic human kappa constant region resulting in the following expression vectors: pKN110-BATRκ$_A$, pKN110-BATRκ$_B$ and pKN110-BATRκ$_D$, respectively (see FIG. 10 for a representative pKN 110-BATRκ$_D$ vector).

Figure 11:
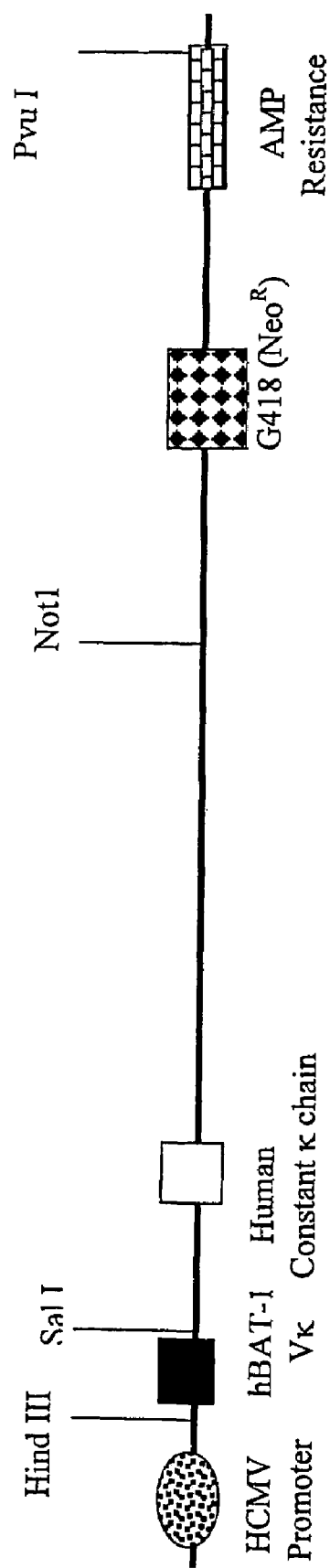
FIG. 11 is a diagrammatic representation of the BAT-1 light chain cassette inserted into BAT-1 light chain expression vectors.

The BAT-1 light chain expression cassette inserted into an expression vector included a DNA fragment encoding a mouse immunoglobulin signal peptide sequence, Kozak sequence and a signal sequence intron which was added to both sides of the humanized $V_\kappa$ gene variants of BAT-1 (FIG. 11). This cassette was inserted between the HCMV Immediate Early Promoter and the genomic human kappa constant region. The complete light chain expression vector also included a BGH polyA transcription terminator and a Neo/G418 selection marker. All constructs were restriction enzyme digested and ds-DNA sequenced to confirm the presence of the correct insert.

Example 7

Construction of Humanized BAT-1 Heavy Chain Variants

The construction of the various versions of the reshaped human BAT-1 heavy chain variable region genes (i.e. BATRH$_A$, BATRH$_B$, BATRH$_C$) produced an approximately 450 bp product which was then subcloned into pCR2.1™. The PCR reactions were set up using the primers described in Tables 11 and 12.

Putative positive transformants were again identified in a PCR screen and then ds-DNA sequenced. The humanized $V_H$ genes (SEQ ID NOS. 20-22) were then subcloned into expression vectors.

Figure 12:
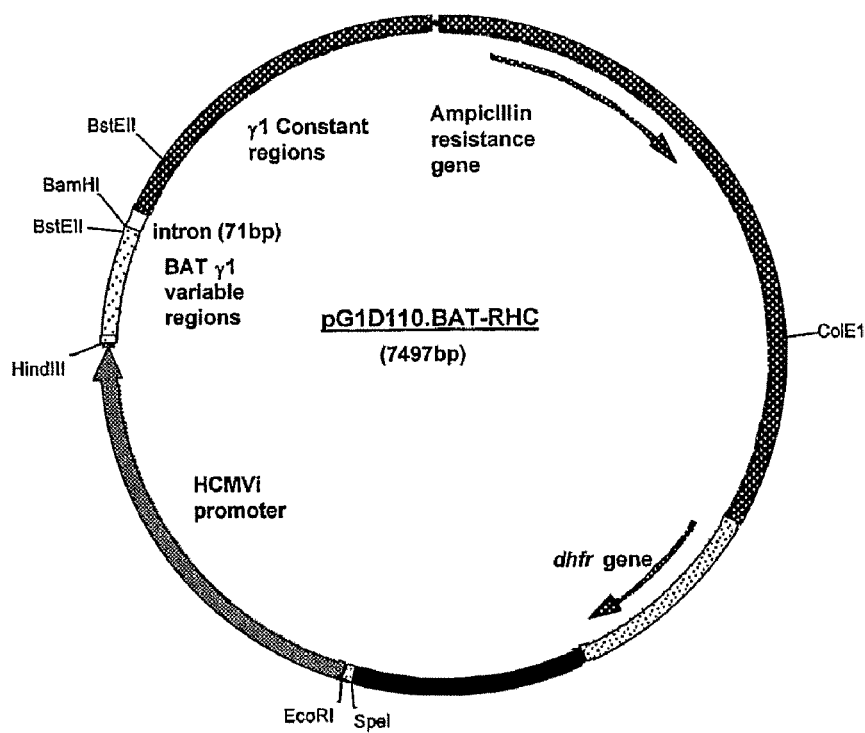
FIG. 12 is a diagrammatic representation of the pG1D110.BAT-1.RH$_c$ vector construct.

The heavy chain pG1D110 construct included Ampicillin resistance gene and the hamster dhfr as the selectable marker. The humanized $V_H$ gene variants of BAT-1 were inserted between the HCMV Immediate Early Promoter and the genomic human IgG1 constant region resulting in the following expression vectors: pG1D110-BATRH$_A$, pG1D110-BATRH$_B$, pG1D110-BATRH$_C$ (see FIG. 12 for a representative pG1D110.BAT-1.RH$_C$ vector).

Figure 13:
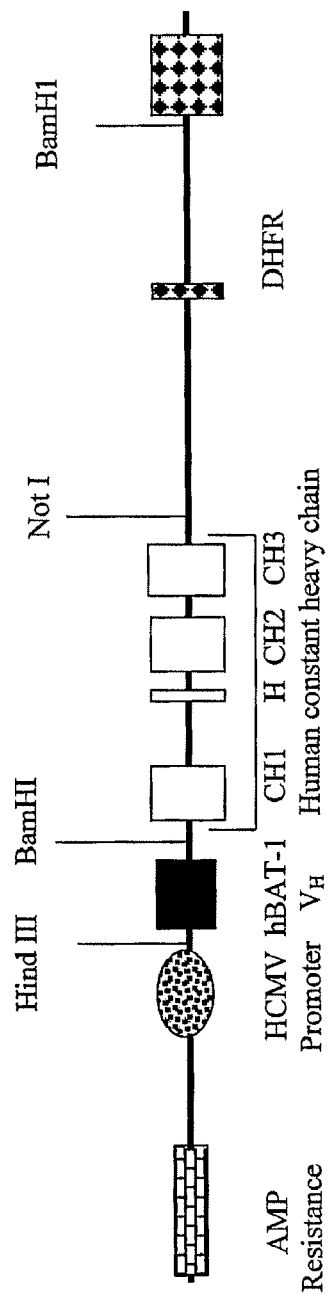
FIG. 13 is a diagrammatic representation of the BAT-1 heavy chain cassette inserted into BAT-1 heavy chain expression vectors.

The BAT-1 heavy chain expression cassette inserted into an expression vector which included a DNA fragment encoding a mouse immunoglobulin signal peptide sequence, Kozak sequence and a signal sequence intron which was added to both sides of the humanized $V_\kappa$ gene variants of BAT-1 (FIG. 13). This cassette was inserted between the HCMV Immediate Early Promoter and the genomic human IgG1 constant region. The complete light chain expression vector also included a BGH polyA transcription terminator and a dhfr selection marker.

The resulting expression vectors were restriction enzyme digested to confirm the presence of the correct insert.

TABLE 11

| Primer Name | SEQ ID NO | Oligonucleotide used in the construction of the various humanized BAT-1 antibody heavy chain variable region gene (5'→3') |
|---|---|---|
| BATRH.1 | 57 | CCCAAGCTTGCCGCCACCATG GACTGGACCTGGAGGATCC |
| BATRH.2 | 58 | TCTTCTTGGTGGCAGCAGCAA CAGGTGCCCACT |
| BATRH.3 | 59 | CCCAGGTGCAGCTGGTGCAAT CTGGGTCTGAGCTTAAGAA |
| BATRH.4 | 60 | GCCTGGGGCCTCAGTGAAGAT CTCCTGCAAGGCTTCTGGA |
| BATRB.5 | 61 | TATAGCTTCAGTAACTATGGA ATGAACTGGGTGCGACAGG |
| BATRH.6 | 62 | CCCCTGGACAAGGGCTTCAGT GGATGGGATGGATAAACAC |
| BATRH.7 | 63 | CGACAGTGGAGAGTCAACATA TGCTGAAGAGTTCAAGGGA |
| BATRH.8 | 64 | CGGTTTGTCTTCTCCTTGGAC ACCTCTGTCAGCACGGCAT |
| BATRH.9 | 65 | ATCTGCAGATCACCAGCCTCA CGGCTGAGGACACTGGCAT |
| BATRH.10 | 66 | GTATTTCTGTGCGAAAGTCGG CTACGATGCTTTGG |
| BATRH.11 | 67 | ACTACTGGGGCCAGGGAACCC TGGTCACCGTCTCCTCAGGTG AGTGGATCCGCG |
| BATRH.12 | 68 | TGCTGCCACCAAGAAGAGGAT CCTTCCAGGTGGAGTCCATGG TGG |
| BATRH.13 | 69 | TTGCACCAGCTGCACCTGGGA GTGGGCACCTGTTGC |
| BATRH.14 | 70 | T CTTCACTGAGGCCCCAGGCT TCTTAAGCTCAGACCCAGA |

TABLE 11-continued

| Primer Name | SEQ ID NO | Oligonucleotide used in the construction of the various humanized BAT-1 antibody heavy chain variable region gene (5'→3') |
|---|---|---|
| BATRH.15 | 71 | CCATAGTTACTGAAGCTATAT CCAGAAGCTTGCAGGAGA |
| BATRH.16 | 72 | CTGAAGCCCTTGTCCAGGGGC CTGTCGCACCCAGTTCATT |
| BATRH.17 | 73 | ATGTTGACTCTCCACTGTCGG TGTTTATCCATCCCATCCA |
| BATRH.18 | 74 | TCCAAGGAGAAGACAAACCGT CCCTTGAACTCTTCAGCAT |
| BATRH.19 | 75 | GAGGCTGGTGATCTGCAGATA TGCCGTGCTGACAGAGGTG |
| BATRH.20 | 76 | CGACTTTCGCACAGAAATACA TGCCAGTGTCCTCAGCCGT |
| BATRH.21 | 77 | TTCCCTGGCCCCAGTAGTCCA AAGCATCGTAGC |
| BATRH.22 | 78 | CGCGGATCCACTCACCTGAGG AGACGGTGACCAGGG |
| BATRH.5B | 79 | TATACTTTCACAAACTATGGA ATGAACTGGGTGCGACAGG |
| BATRH.15B | 80 | CCATAGTTTGTGAAAGTATAT CCAGAAGCTTGCAGGAGA |
| BATRH.8C | 81 | CGGTTTGTCTTCTCCTTGGAC ACCTCTGTCAACACGGCAT |
| BATRH.10C | 82 | GTATTTCTGTGTGAGAGTCGG CTACGATGCTTTGG |
| BATRH.20C | 83 | CGACTCTCACACAGAAATACATG CCAGTGTCCTCAGCCGT |
| BATRH.9C | 84 | ATCTGCAGATCACCAGCC TC AACGCTGAGGACACTGGCAT |
| BATRH.19C | 85 | GAGGCTGGTGATCTGCAGAT ATGCCGTGTTGACAGAGGTG |
| BATRH.5C | 86 | TATACTTTCACAAACTATGG AATGAACTGGGTGAAGCAGG |

TABLE 12

| Humanized BAT-1 variant | Oligonucleotide primer[1] combinations used for the construction of the heavy chain of each variant[2] | | | | |
|---|---|---|---|---|---|
| BATRH$_A$ | BATRH.1 | BATRH.2 | BATRH.3 | BATRH.4 | BATRH.5 |
| | BATRH.6 | BATRH.7 | BATRH.8 | BATRH.9 | BATRH.10 |
| | BATRH.11 | BATRH.12 | BATRH.13 | BATRH.14 | BATRH.15 |
| | BATRH.16 | BATRH.17 | BATRH.18 | BATRH.19 | BATRH.20 |
| | BATRH.21 | BATRH.22 | | | |
| BATRH$_B$ | BATRH.1 | BATRH.2 | BATRH.3 | BATRH.4 | BATRH.5B |
| | BATRH.6 | BATRH.7 | BATRH.8 | BATRH.9 | BATRH.10 |
| | BATRH.11 | BATRH.12 | BATRH.13 | BATRH.14 | BATRH.15B |
| | BATRH.16 | BATRH.17 | BATRH.18 | BATRH.19 | BATRH.20 |
| | BATRH.21 | BATRH.22 | | | |
| BATRH$_C$ | BATRH.1 | BATRH.2 | BATRH.3 | BATRH.4 | BATRH.5C |
| | BATRH.6 | BATRH.7 | BATRH.8C | BATRH.9 | BATRH.10 |
| | BATRH.11 | BATRH.12 | BATRH.13 | BATRH.14 | BATRH.15C |
| | BATRH.16 | BATRH.17 | BATRH.18 | BATRH.19 | BATRH.20 |
| | BATRH.21 | BATRH.22 | | | |

[1]Oligonucleotide sequences are given in Table 11.
[2]Oligonuclotide primers BATRH.1 and BATRH.22 were also used as the outer amplification primers.

Example 8

Figure 14:
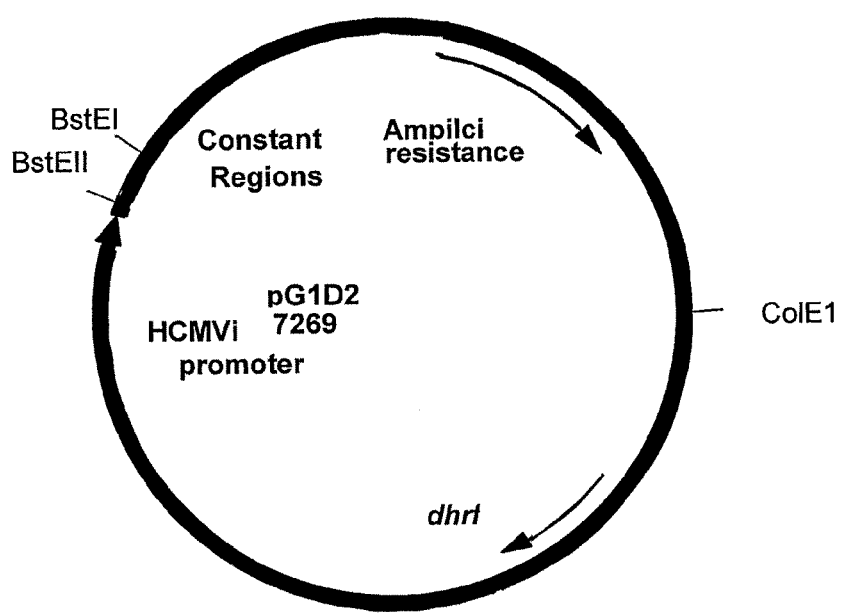
FIG. 14 is a diagrammatic representation of the pG1D200 gamma-1 immunoglobulin heavy chain mammalian expression vector.

Construction of BAT-1 RH$_C$/Rκ$_D$ γ1 Complete Antibody in a Single Expression Vector In order to maximize the achievable expression levels for the BAT-1 γ1 antibody it was decided to remove an intron from the pG1D110.BAT-1.RH$_C$ construct (described in Example 7, see FIG. 12) before making the BAT-1 γ1 single vector construct. This procedure was carried out as follows.

pG1D200 is another γ1 immunoglobulin heavy chain mammalian expression vector (AERES Biomedical; FIG. 14). This vector is a V$_H$:C$_H$ γ1 intron minus version of the pG1D110 vector (i.e. it does not have the 71 bp intron at the V$_H$:C$_H$ junction).

In order to convert the pG1D110.BAT-1.RH$_C$ construct into a construct, a BstEII fragment (219 bp) was excised from the pG1D200 vector and gel purified using a Qiagen gel extraction/purification kit. This fragment contained the intron minus V$_H$:C$_H$ junction.

The pG1D110.BAT-1.RH$_C$ construct (FIG. 12) was also restriction digested with BstEII, releasing a 290 bp fragment which contained the intron plus VH:CH junction. The remaining vector fragment (~7207 bp) was gel purified using a Qiagen gel extraction/purification kit.

The intron minus BstEII fragment (219 bp) from the pG1D200 vector digest was then ligated into the ~7207 bp BstEII digested pG1D110.BAT-1.RH$_C$ vector. 2 µl of ligated DNA was transformed into DH5α cells (Stratagene) according to the manufacturers instructions. Plasmid DNA was prepared from 10 colonies and each plasmid DNA was analyzed for the presence of the correct BstEII fragment by DNA sequence analysis.

Following identification of a perfect clone, the new intron minus construct (pG1D210.BAT-1.RH$_C$) and the light chain construct pKN110.BAT.Rκ$_D$ (see FIG. 10) were used to construct the pG1KD210.BAT-1.RH$_C$/Rκ$_D$ single expression vector (SEQ ID NO. 93).

The component of this pG1KD210.BAT-1.RH$_C$/Rκ$_D$ single expression vector within SEQ ID NO 93 are localized as follows:

1. Nucleotide range: 1 to 2502—pBR322 (pBR322 based sequence including the Amp-resistance gene and ColEI origin plus the SV40 origin and crippled SV40 early promoter)
2. Nucleotide range: 206 to 1067—Amp (Ampicillin resistance gene)
3. Position: 1824—ColE1
4. Nucleotide range: 2502 to 3227—DHFR (Dihydrofolate reductase gene)
5. Nucleotide range: 3233 to 4074—SV40 polyA (SV40 poly A sequence etc)
6. Nucleotide range: 4109 to 5649—HCMVi (HCMVi promoter)
7. Nucleotide range: 5662 to 6067—BAT rKd
Reshaped BAT Kappa Light Chain Variable Region.
8. Nucleotide range: 6073 to 6720—HuK (cDNA copy of human kappa constant region (Km(3)) gene)
9. Nucleotide range: 6726 to 6943—spaC2 Artificial spaC2 termination sequence
10. Nucleotide range: 6949 to 8489—HCMVi (HCMVi promoter)
11. Nucleotide range: 8502 to 8923—BAT rHc
Reshaped BAT Heavy Chain Variable Region
12. Nucleotide range: 8924 to 10297—HG1 (Human gamma-1 constant regions preceded by a 60 bp intron and followed by the 'Arnie' termination sequence)

Figure 15:
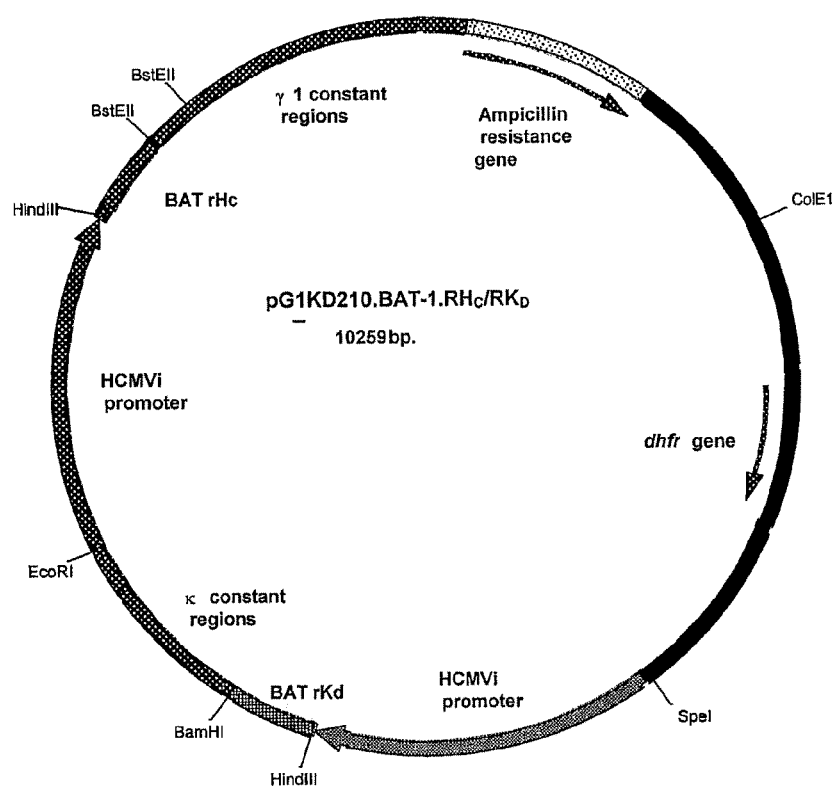
FIG. 15 is a diagrammatic representation of the pG1KD210.BAT-1.RHC/RKD single expression vector (SEQ ID NO. 93).

The BAT-1 kappa light chain expression cassette which contained the HCMVi promoter, the BAT-1 kappa light chain variable region gene, and the kappa light chain constant region gene, was restriction enzyme digested (EcoRI/SpeI) out of the pKN110.BAT-1.Rκ$_D$ construct and subsequently ligated into the pG1D210.BAT-1.RH$_C$ construct via the unique EcoRI and SpeI restriction sites. This ligation resulted in the construction of the single expression vector pG1KD210.BAT-1.RH$_C$/Rκ$_D$, containing both the heavy and kappa light chains of the BAT-1 humanized antibody RH$_C$/Rκ$_D$ (FIG. 15). 2 µl of ligated DNA was transformed into DH5α cells (Stratagene) according to the manufacturers instructions. Mini prep DNA was prepared from ten colonies and each plasmid DNA was analyzed for the presence of the correct single expression construct by restriction digest analysis. One clone of a correct single expression construct was chosen for the transient expression of the BAT-1 gamma-1 antibody in COS cells as will be illustrated in Example 11.

Example 9

Figure 16:
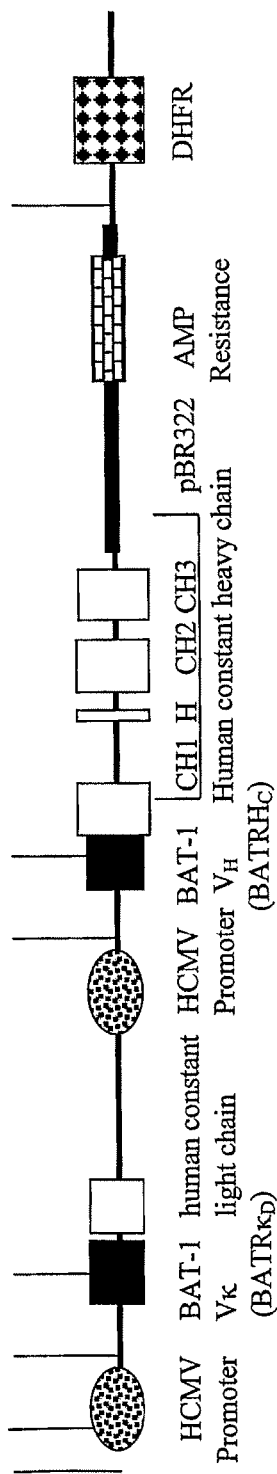
FIG. 16 is a diagrammatic representation of the BATRκ$_D$/BATRH$_C$ heavy and light chains cassette inserted into a single expression vector for the expression of the complete BAT-1 antibody.
Figure 17:
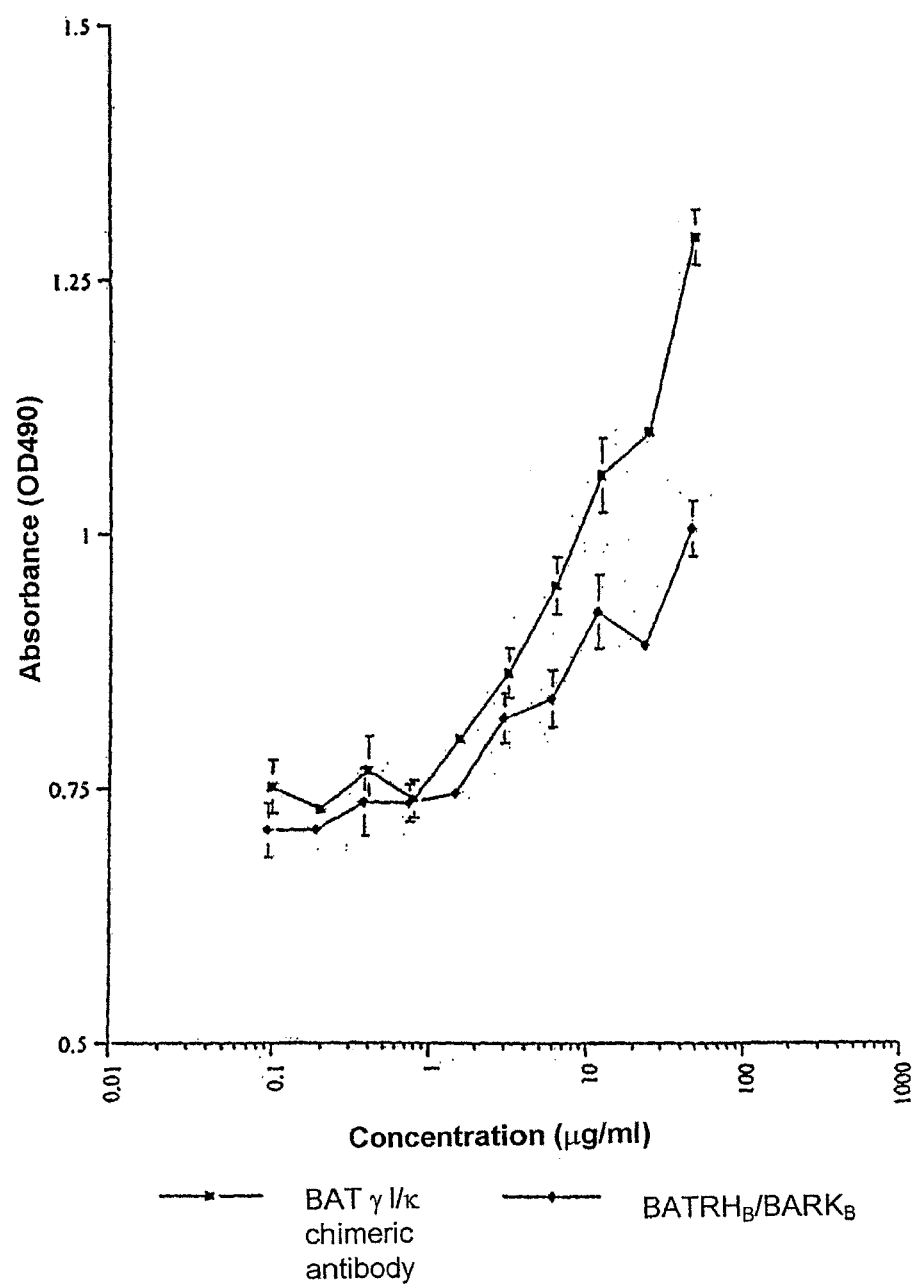
FIG. 17 shows a Daudi cell ELISA of humanized BATRH$_B$/BATRκ$_B$ variant against BAT-1 chimeric antibody.
Figure 18:
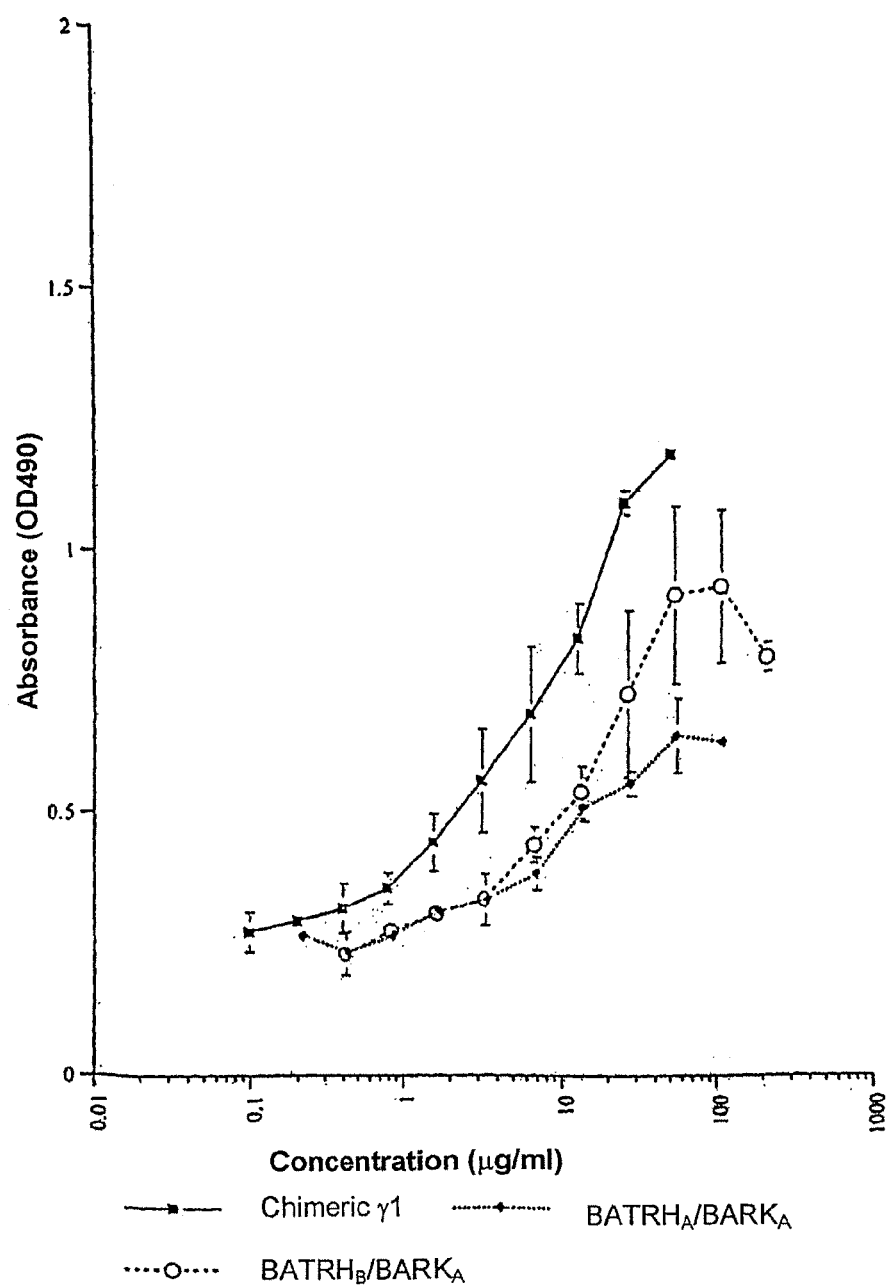
FIG. 18 shows a Daudi cell ELISA of humanized BATRH$_B$/BATRκ$_A$ and BATRH$_A$/BATRκ$_A$ variants against BAT-1 chimeric antibody.
Figure 19:
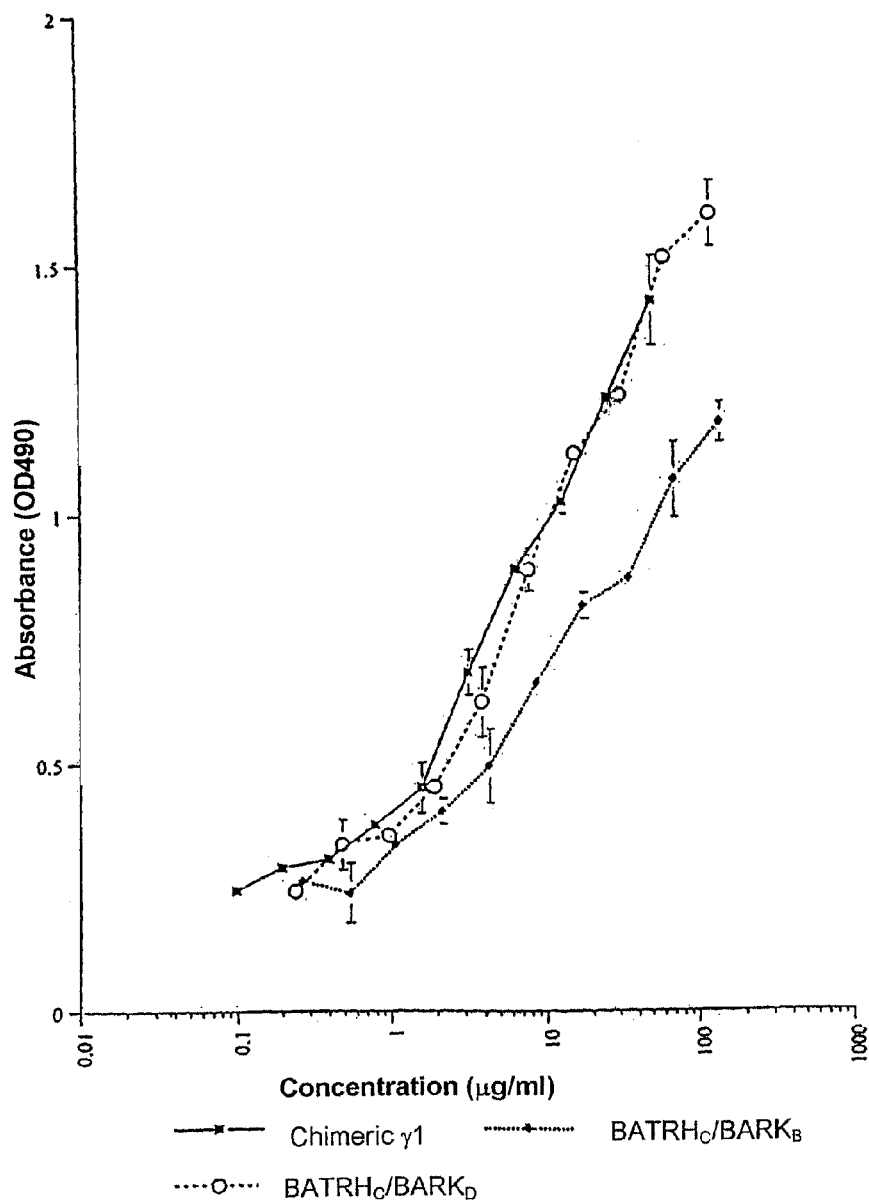
FIG. 19 shows a Daudi cell ELISA of humanized BATRH$_C$/BATRκ$_B$ and BATRH$_C$/BATRκ$_D$ variants against BAT-1 chimeric antibody.
Figure 20:
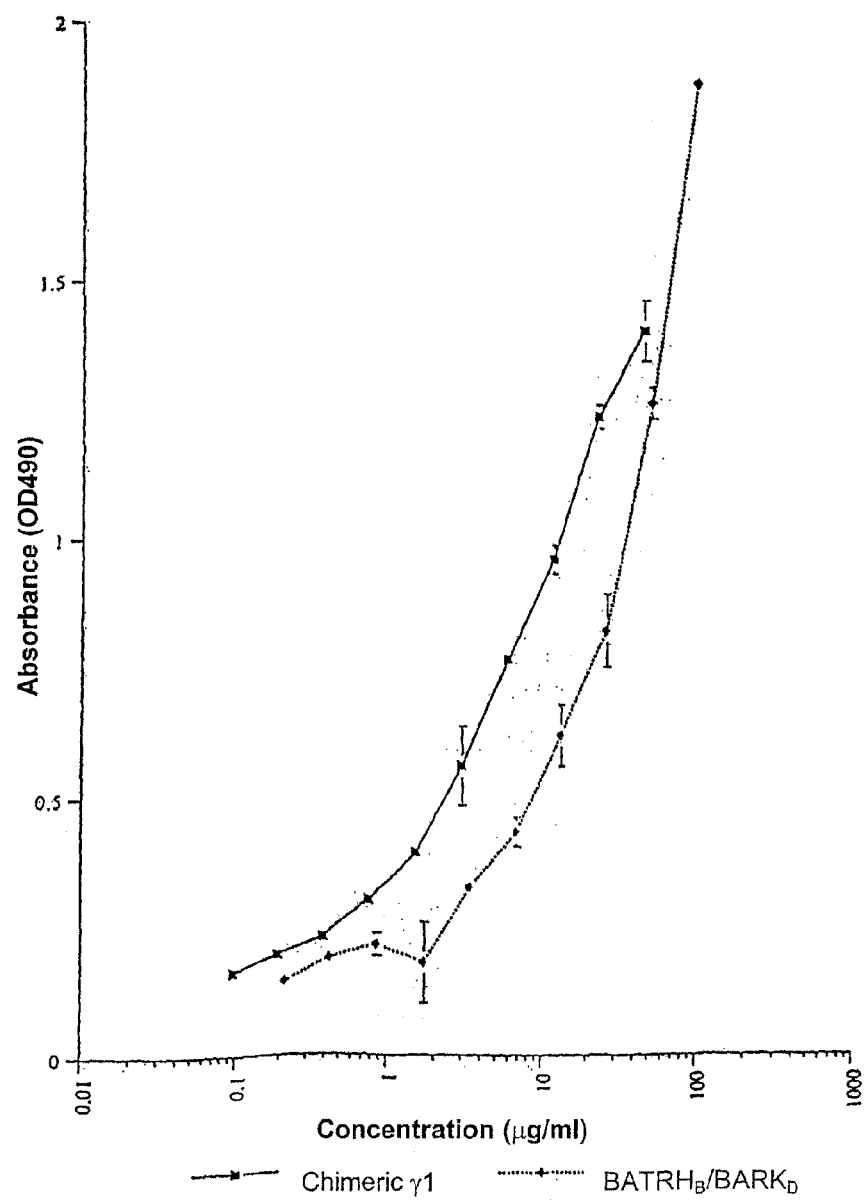
FIG. 20 shows a Daudi cell ELISA of humanized BATRH$_B$/BATRκ$_D$ variant against BAT-1 chimeric antibody.

Construction of the BAT-1.RH$_C$/Rκ$_D$ Gamma-1 (γ1) Complete Antibody Variant in a Single Expression Vector The BATRH$_C$ heavy chain variable region was transferred to the combined (single) expression vector as an XhoI to HindIII fragment. The BATRκ$_D$ light chain variable region was transferred to the combined (single) expression vector as an XbaI to BamHI fragment. The internal XbaI site in the light chain gene was removed without changing the amino acid sequence. The sequences of the BAT-1.Rκ$_D$/BAT-1.RH$_C$ heavy and light chain variable regions in this vector were confirmed. The vector includes genomic human IgG1 and Kappa constant regions. Both heavy and light chain genes were placed under the control of the HCMV Immediate Early promoter. The vector includes a mouse dhfr gene as the selectable marker (see FIG. 16). The same Kozak sequence, signal peptide sequence and intron were added as for the two vector expression system (see Examples 6 and 7).

Example 10

Construction of the BAT-1 Gamma-4 (γ4) PG4KD110.BAT-1. RH$_C$/RK$_D$ in a Single Vector The first step in the construction of the BAT-1 γ4 single expression vector construct was the cloning of the modified BAT-1.RH$_C$ gene out of the pG1D110.BAT-1.RH$_C$ construct by BamHI and HindIII restriction digest, and ligation of this 430 bp fragment into the gamma-4 immunoglobulin heavy chain expression vector pG4D110, again via BamHI and HindIII restriction sites.

2 µl of ligated DNA was transformed into DH5α cells (Stratagene) according to the manufacturers instructions. Plasmid DNA was prepared from 10 colonies and each plasmid DNA was analyzed for the presence of the correct BAT-1.RH$_C$ BamHI/HindIII fragment by DNA sequence analysis.

Following identification of a perfect clone, the new gamma-4 construct (pG4D110.BAT-1.RH$_C$) and the light chain construct pKN110.BAT-1.RK$_D$ (FIG. 10) were used to construct the pG4KD110.BAT-1.HR$_C$/Rκ$_D$ single expression vector in the following way.

The BAT-1 kappa light chain expression cassette which contained the HCMVi promoter, the BAT-1 kappa light chain variable region gene, and the kappa light chain constant region gene, was restriction enzyme digested (EcoRI/SpeI) out of the pKN110.BAT-1.Rκ$_D$ construct and subsequently ligated into pG4D110.BAT-1.RH$_C$ construct via the unique EcoRI and SpeI restriction sites. This ligation resulted in the construction of a single expression vector construct pG4KD110.BAT-1.RH$_C$/Rκ$_D$, containing both the heavy and kappa light chains of the BAT-1 humanized antibody RH$_C$/Rκ$_D$ variant. 2 µl of ligated DNA was transformed into DH5α cells (Stratagene) according to the manufacturers instructions. Mini prep DNA was prepared from ten colonies and each plasmid DNA was analyzed for the presence of the correct single expression vector construct by restriction digest analysis. The correct single expression vector construct digested with BamHI and with HindIII released a 2864 bp fragment and the HindIII digest released a 2840 bp fragment. One clone was chosen for the transient expression of the BAT-1 gamma-4 antibody in COS cells.

Example 11

Co-transfection of Humanized BAT-1 Light and Heavy Chain Vectors, and Transient Expression of the Humanized BAT-1 Variants in COS7 Cells The humanized BAT-1 heavy (pG1D110) and light (pKN110; Example 7) chain expression vectors were co-transfected, at various combinations, into COS7 cells and after 72 hr incubation, the medium was collected, spun to remove cell debris, filtered and analyzed by ELISA for humanized antibody production. The concentration of humanized antibody in the COS7 cell supernatants varied with each combination of reshaped human BAT-1 antibody constructs that were tested (Table 13). For example, version $BATRH_B/BATR\kappa_A$ expressed the highest antibody levels (4800 ng/ml) whilst the $BATRH_B/BATR\kappa_D$ version was the poorest expresser (357 ng/ml).

Example 12

Purification of the Humanized BAT-1 Variants from COS7 Cells

Harvesting approximately 8 ml per co-transfection (see Example 11), a series of transfections were carried out until in excess of 200 ml of COS7 supernatant had been collected. The volume of this supernatant was reduced to 10 ml by passing the supernatant through a stirred ultra-filtration cell with a PM30 filter membrane—which had a molecular weight cut-off of 30 kDa.

The IMMUNOPURE™ IgG purification kit essentially comprised of a 2 ml column of immobilized Protein A Sepharose column. The antibody was eluted from the column with 5 ml of elution buffer, the eluate of which was collected in 1 ml fractions. The concentration of humanized BAT-1 antibody in each fraction was then assayed using ELISA methods. Table 13 describes the final concentrations of the Protein A purified antibodies. On average the purification step increased the antibody concentration by approximately 150-fold.

TABLE 13

Chimeric and hBAT-1 antibody concentrations in COS7 cells supernatants (transient expression experiments)

| Antibody chain | | | After Protein A |
|---|---|---|---|
| Heavy | Kappa Light | Raw supernatants (µg/ml) | Purification (µg/ml) |
| BATCH | BATRκ | 0.358 | 50 |
| $BATRH_A$ | $BATR\kappa_A$ | 2.350 | 110 |
| $BATRH_B$ | $BATR\kappa_A$ | 4.800 | 211 |
| $BATRH_B$ | $BATR\kappa_B$ | 0.757 | 149 |
| $BATRH_C$ | $BATR\kappa_B$ | 1.250 | 137 |
| $BATRH_B$ | $BATR\kappa_D$ | 0.357 | 112 |
| $BATRH_C$ | $BATR\kappa_D$ | 0.718 | 122 |

Example 13

Analysis of Daudi Cell Binding to the Humanized BAT-1 Variants Produced in COS7 Cells Using the Daudi cell ELISA it was clear that the different versions of the Protein A purified humanized BAT-1 antibody bound to Daudi cells to various degrees. FIGS. 17-20 show typical examples for these binding experiments. Sigmoidal dose-response curves of Daudi cell binding by the recombinant antibodies were also plotted and the hill slopes of these binding curves were calculated. The combination of the hill slope data and the positions of the dose-response curves relative to the chimeric antibody dose-response curves suggested a qualitative hierarchy with respect to Daudi cell binding among the various humanized BAT-1 antibody constructs tested (Table 14). At the top of this hierarchy was clearly construct $BATRH_C/BATR\kappa_D$, which exhibited a hill slope (i.e. 0.8818±0.1107) very similar to its chimeric BAT-1 antibody control (i.e. 0.8248±0.1210) and closely tracked the dose-response curve of the chimeric control. Although construct $BATRH_C/BATR\kappa_B$ displayed a steeper hill slope (i.e. 0.6408±0.1622) than the same chimeric BAT-1 antibody control (i.e. 0.8248±0.1210), as calculated from the available binding data, the difference was no statistically significant. In addition, it is clear from FIG. 19 that the dose-response curve for this construct is not as good as for the $BATRH_C/BATR\kappa_D$ construct and was therefore ranked second in the binding hierarchy.

Conversely, construct $BATRH_A/BATR\kappa_A$ clearly has the poorest binding characteristics of all the humanized BAT-1 antibody constructs tested (Table 14) and so was ranked sixth in the binding hierarchy. Although the calculated hill slope for this version (i.e. 1.2730±0.2688) is apparently better than the very similar humanized construct $BATRH_B/BATR\kappa_A$ (i.e. 1.7710±0.6461) this difference is again not statistically significant. In addition, it is clear from FIG. 18 that the CDR-grafted $BATRH_A/BATR\kappa_A$ BAT-1 antibody is reaching its maximum binding response at much lower level than the humanized construct $BATRH_B/BATR\kappa_A$—which was ranked fifth in the binding hierarchy.

Constructs $BATRH_B/BATR\kappa_B$ (FIG. 17; ranked fourth) and $BATRH_B/BATR\kappa_D$ (FIG. 20; ranked third) display intermediate levels of binding between these two sets of extremes. Again these rankings were mainly based upon a subjective interpretation of the binding data available and previous experience.

TABLE 14

Relative binding affinities of Protein A purified humanized versus chimeric BAT-1 antibodies constructs harvested following transient expression in COS cells

| Experiment Number | Heavy Chain | Kappa Light Chain | Hill slope ±SEM[a] | Binding hierarchy from hill slope analysis |
|---|---|---|---|---|
| 1 | BATRH | BATRκ | 0.5422 ± 0.2911 | — |
|  | $BATRH_A$ | $BATR\kappa_A$ | 1.273 ± 0.2688 | 6 |
|  | $BATRH_B$ | $BATR\kappa_A$ | 1.771 ± 0.6461 | 5 |
| 2 | BATRH | BATRκ | 0.8057 ± 0.0849 | — |
|  | $BATRH_B$ | $BATR\kappa_D$ | 0.6555 ± 0.1252 | 3 |
| 3 | BATRH | BATRκ | 0.8248 ± 0.1210 | — |
|  | $BATRH_C$ | $BATR\kappa_B$ | 0.6408 ± 0.1622 | 2 |
|  | $BATRH_C$ | $BATR\kappa_D$ | 0.8818 ± 0.1107 | 1 |
| 4 | BATRH | BATRκ | 0.7090 ± 0.2768 | — |
|  | $BATRH_B$ | $BATR\kappa_B$ | 0.7796 ± 0.3420 | 4 |

[a]Standard error mean of 3 duplicate Daudi cell ELISA calculated after fitting ELISA data onto a sigmoidal dose-response curve.

Example 14

Transient Expression of the BAT-1 RK$_D$/RH$_C$ Variant by Co-transfection or by Single Transfection of COS Cells The method of Kettleborough (Kettleborough et al., Eur. J. Immunol. 23:206, 1993) was followed to transfect the mammalian expression constructs into COS cells. Briefly, the DNA (10 μg each of the kappa light chain expression construct pKN110.BAT-1.RK$_D$ and the heavy chain expression construct pG1D210.BAT-1.RH$_C$, or 13 μg of the single vector construct pG1KD210.BAT-1.RH$_C$/RK$_D$) was added to a 0.7 ml aliquot of $10^7$ cells/ml in PBS and pulsed at 1900 V, 25 μF capacitance using a Bio-Rad Gene Pulser apparatus. Following a 10 minute recovery at room temperature, the electroporated cells were transferred to petri-dishes containing 8 ml of DMEM containing 10% FCS and incubated for 72 hrs in 5% $CO_2$ at 37° C. After 72 hrs incubation, the medium was collected, spun to remove cell debris, and analyzed by capture ELISA for antibody production. The co-transfections, with light chain expression vector and heavy chain expression vector, and transfections with a single-vector expressing both light and heavy chains, were carried out in triplicate. The results are presented in Table 15. The results indicate that expression levels from the single vector are ~6 fold higher than the expression levels observed for the co-transfections.

TABLE 15

| Transfection no. | Construct transfected | Transient COS cell expression levels for the BAT-1 γ1 antibody (μg/ml)* |
|---|---|---|
| 1 | Single vector | 55.451 |
| 2 | " | 49.009 |
| 3 | " | 66.018 |
| 1 | Light and heavy chain vectors | 9.06 |
| 2 | " | 10.232 |
| 3 | " | 9.536 |

*Trasfection levels of humanized RH$_C$/RK$_D$ BAT-1 variant, from co-trasfection using pG1D110 and pKN110 vectors, were 0.718 μg/ml

Example 15

Stable Transfection of CHOdhfr– Mammalian Cells with the Single Vector pG1KD210.BAT-1.RH$_C$/RK$_D$ and Production of Stable Cell Lines CHOdhfr– cells were propagated in a non-selective media consisting of α-MEM with ribonucleosides and deoxyribonucleosides, supplemented with 10% Fetal Clone II and 50 μg/ml Gentamicin. Aliquot, 0.7 ml, of $10^7$ cells/ml in PBS was transfected with 13 μg of pG1KD210.BAT-1.RH$_C$/RK$_D$ at 1900 V, 25 μF capacitance using a Bio-Rad Gene Pulser. The cells were allowed to recover for 10 minutes at RT before being transferred to 10 cm petri-dishes in 8 ml of non-selective media and then incubated in 5% $CO_2$ at 37° C. for 48 hours.

Two days after transfection, the cells were trypsinized, spun down and resuspended in 150 ml of prewarmed selective media (α-MEM without ribonucleosides and deoxyribonucleosides, supplemented with 10% dialyzed FBS and 50 μg/ml Gentamicin, and containing either 10 nM, 50 nM, 100 nM or 500 nM Methotrxate) before being divided equally between fifteen 10 cm petri-dishes. These were then incubated in 5% $CO_2$ at 37° C. for 20-30 days, the selective media being changed every 3-4 days until foci were clearly visible. After 2 weeks from the initial transfection, foci began to develop on the 10 nM plates. Eight days later, one focus developed on the 50 nM plates. No other foci developed after 35 days, on the 50 nM plates and no foci developed on the 100 nM or 500 nM plates.

To "pick" foci, 1 mm squares of Whatman 1 MM filter paper were first immersed in 0.05% trypsin, 0.02% EDTA solution. The selective media was carefully removed from the culture dishes, which were then washed carefully with 5 ml of PBS. The PBS was then removed and, using sterile forceps, the squares of pre-soaked filter paper were carefully placed onto individual focus of cells. The squares were left on the foci for 15 seconds before being transferred into individual wells of a 24-well tissue culture plate containing 1 ml of the appropriate selective media.

A total of 31 gamma-1 foci were picked, 30 were from the 10 nM MTX plates and one was from the 50 nM plates. These cells were allowed to grow in selective media until almost confluent and the media from individual wells was tested for antibody production. Those clones producing human antibody were then selected for expansion and specific production analysis. The results of the specific production assays are presented in Table 16.

TABLE 16

| | Specific CHO cell production levels for the RH$_C$/RK$_D$ BAT-1 γ1 whole antibody variant (ng/$10^6$ cells/day) | | |
|---|---|---|---|
| Clone | ASSAY NO. 1 | Assay No. 2 | Assay No. 3 |
| γ1 B9 | 3284.7 | 2921.5 | 1227.1 |
| γ1 B10 | 297 | 1288 | 268.3 |
| γ1 B13 | 12443 | 5425.2 | 7731.53 |
| γ1 B18 | 6.5 | 10.4 | 4.9 |
| γ1 B19 | 199.7 | 26.9 | 43 |
| γ1 B15 | 5978.6 | 1657.1 | 3015.43 |
| γ1 D6 | 2539.2 | 1605.5 | 2072.40 |

The three cell lines (B9, B13 and B15) which showed the best specific productivity levels were further analyzed and monitored for accurate doubling times. (see Table 17).

TABLE 17

| Cell line | Production levels of the best γ1 CHO cell lines (μg/$10^6$ cells/day) | Doubling time of the best γ1 CHO cell lines (hours) |
|---|---|---|
| B9 | 3.5 | 22.5 |
| B13 | 7.7 | 31.5 |
| B15 | 3 | 21 |

Based on specific productivity levels and doubling times it was decided to begin production of the 500 μg quantity of the BAT-1 γ1 antibody using the B15 cell line.

Example 16

Transient Expression of BAT-1 γ4 RH$_C$/RK$_D$ Variant in COS Cells by Single- and Co-transfections The method of Kettleborough et al. was followed to transfect the mammalian expression constructs into COS cells. Briefly, the DNA (10 kg each of the kappa light chain expression construct pKN110.BAT-1.RK$_D$ and the heavy chain expression construct pG4D110.BAT-1.RH$_C$, or 13 μg of the supervector construct pG4D110.BAT-1.RH$_C$/RK$_D$) was added to a 0.7 ml aliquot of $10^7$ cells/ml in PBS and pulsed at 1900 V, 25 µF capacitance using a Bio-Rad Gene Pulser apparatus. Following a 10 minute recovery at RT, the electroporated cells were transferred to petri-dishes containing 8 ml of DMEM containing 10% FCS and incubated for 72 hrs in 5% $CO_2$ at 37° C. After 72 hrs incubation, the medium was collected, spun to remove cell debris, and analyzed by capture ELISA for antibody production.

Both the co-transfections and single transfections were carried out in triplicate. The results are presented in Table 18. The results indicate that expression levels from this single expression vector are ~4 fold higher than the expression levels observed for the co-transfections.

TABLE 18

| Transfection No. | Construct transfected | Transient COS cell expression levels for the BAT-1 γ4 antibody (ng/ml) |
|---|---|---|
| 1 | Single vector | 519.3 |
| 2 | " | 522 |
| 3 | " | 567.2 |
| 1 | Light and heavy chain vectors | 65.6 |
| 2 | " | 152.3 |
| 3 | " | 129.9 |

Example 17

Stable Transfection of CHOdhfr− Mammalian Cells with the Single Vector pG4KD210.BAT-1.$RH_C$/$Rκ_D$ and Production of Stable Cell Lines CHOdhfr− cells were propagated in a non-selective media consisting of α-MEM with ribonucleosides and deoxyribonucleosides, supplemented with 10% Fetal Clone II and 50 µg/ml Gentamicin. Aliquot, 0.7 ml, of $10^7$ cells/ml in PBS was transfected with 13 µg of pG4KD110.BAT-1.$RH_C$/$Rκ_D$ at 1900 V, 25 µF capacitance using a Bio-Rad Gene Pulser. The cells were allowed to recover for 10 minutes at room temperature before being transferred to 10 cm petri-dishes in 8 ml of non-selective media and then incubated in 5% $CO_2$ at 37° C. for 48 hours. Two days following this incubation, the cells were trypsinized, spun down and resuspended in 150 ml of prewarmed selective media (α-MEM without ribonucleosides and deoxyribonucleosides, supplemented with 10% dialyzed FBS and 50 µg/ml Gentamicin, and containing either 10 nM, 50 nM, 100 nM or 500 nM Methotrexate) before being divided equally between fifteen 10 cm petri-dishes. These were then incubated in 5% $CO_2$ at 37° C. for 20-30 days, the selective media being changed every 3-4 days until foci were clearly visible.

After 2 weeks, foci began to develop on the 10 nM plates. No foci developed after 35 days on the 50 nM plates and on the 100 nM or 500 nM plates. Foci were picked as described earlier (Example 15) and those selected clones producing human antibody were then selected for expansion and specific production analysis. The results of the specific production assays are presented in Table 19.

TABLE 19

| | CHO cell production levels for the BAT-1 γ4 whole antibody (ng/$10^6$ cells/day) | | |
|---|---|---|---|
| Clone | ASSAY NO. 1 | ASSAY NO. 2 | ASSAY NO. 3 |
| γ4 A9 | 4.8 | 6.08 | 5.7 |
| γ4 A13 | 48.5 | 14.8 | 68.8 |

TABLE 19-continued

| | CHO cell production levels for the BAT-1 γ4 whole antibody (ng/$10^6$ cells/day) | | |
|---|---|---|---|
| Clone | ASSAY NO. 1 | ASSAY NO. 2 | ASSAY NO. 3 |
| γ4 A12 | 60.7 | 77.0 | 52.7 |
| γ4 C4 | 66.0 | 141.7 | 104.4 |
| γ4 C8 | 41.7 | 52.4 | 77.6 |
| γ4 C9 | 30.7 | 30.6 | 32.2 |
| γ4 F2 | 40.7 | 17.9 | 29.30 |

Example 18

Co-transfection of NS0 Cells with $BATH_C$ Heavy Chain and $BATκ_D$ Light Chain Amplification Vectors and Selection of Antibody Producing Cell Lines Expression vectors containing the $BATRH_C$ heavy chain cassette (FIG. 13) and the $BATRκ_D$ light chain cassettes (FIG. 11) were mixed and transfected into the NS0 host cell line by electroporation.

Transfected cells were distributed into 10 96-well plates in Dulbecco's Modified Eagles medium (DMEM) supplemented with 10% Foetal Bovine Serum (FBS) and 1 mg/ml G418 (Gentamicin) medium. After 10 to 14 days when colonies of transfected cells have developed, samples of conditioned medium from the wells were assayed for humanized BAT-1 antibody. Cells from the highest producing wells were picked, and expanded in medium including G418.

The transfection was repeated after one week as a back up and to provide more transfected cell clones for selection. After 10 days visible colonies of transfected cells had developed, and conditioned medium from the wells was screened for antibody production. ELISA plates were coated with sheep anti-human κ antibody. 25 µl samples of medium from the wells were transferred to the ELISA plate and diluted to 100 µl in PBS Tween (PBST). The secondary antibody was HRP-conjugated sheep anti-human IgG (γ chain specific) and color was developed with o-Phenylene Diamine (OPD). Positive wells were examined microscopically and the cells from the highest producing wells were picked into 1.5 ml of DMEM supplemented with 10% FBS and 1 mg/ml G418 in 24 well plates. A total of 15 high producing colonies were picked from the two transfections (Table 20). Two independent cell lines gave antibody production levels around 40 µg/ml or greater.

For amplification using the dhfr gene in the heavy chain vector, an initial two high producing cell lines have been transferred to medium (DMEM with 10% FCS and 1 mg/ml G418) with 0.02 µM Methotrexate added.

Example 19

Transfection of NS0 Host Cell Line with a Single Amplification Vector Containing BAT-1.$RH_C$/$Rκ_D$ γ1 Gene and Selection of Antibody Producing Cell Lines The combined (single) antibody expression vector described in Example 9, was transfected into the NS0 host cell line by electroporation.

Transfected cells were distributed into 10 96-well plates in DMEM with 10% FBS. After 2 days an equal amount of medium with 0.1 μM Methotrexate was added. Half the medium was changed with the same volume of 0.1 μM MTX-containing medium every 2 days until the 8$^{th}$ day post transfection. The transfection was repeated after one week as a back up and to provide more transfected cell clones for selection. After 14-21 days visible colonies of transfected cells had developed, and conditioned medium from the wells was screened for antibody production as described in the above Example. Positive wells were examined microscopically and the cells from the highest producing wells were picked into 1.5 ml of DMEM supplemented with 10% FBS and 0.1 μM Methotrexate in 24 well plates. A total of 13 high producing colonies were picked from the two transfections and kept frozen in liquid nitrogen (Table 20). Six independent cell lines gave antibody production levels above 40 μg/ml. Due to the different selection, the cell lines containing the single vector were slower to develop than those containing the antibody genes on 2 different vectors.

TABLE 20

| Two Vector System | | Single Vector System | |
| --- | --- | --- | --- |
| Cell line | Production level (μg/ml) | Cell line | Production level (μg/ml) |
| 31E1 | 43 | 1B7 | 48 |
| 33E5 | 15 | 3E3 | 45 |
| 33B10 | 40 | 3H5 | 35 |
| 34F1 | 8 | 8H7 | 26 |
| 35C12 | 12.5 | 9D7 | 41 |
| 36G4 | 4 | 24B7 | 26 |
| 37H5 | 20 | 26A6 | 24 |
| 38E8 | 15 | 26D6 | 33 |
| 39A3 | 38 | 26E3 | 43 |
| 42G7 | 12 | 27B2 | 23 |
| 44F4 | 7 | 27C4 | 45 |
| 45C2 | 10 | 23E10 | 45 |
| 45H12 | 13 | 29E3 | 22 |
| 46A10 | 7 | | |
| 49H2 | 15 | | |

A representative example of the humanized BAT producing cells after transfection of an NSO host cell line with a single amplification vector containing BAT-1.RH$_C$/Rκ$_D$ γ1 gene and selection of antibody producing cell lines, i.e., cloned cell line 1B7, was deposited at the ATCC Cell Bank using the Budapest Treaty Deposit Form on May 9, 2003 under accession number ATCC# (PTA-5189).

Example 20

Inhibition of Mouse BAT-1 by Humanized BAT-1.RH$_C$/Rκ$_D$ γ1 Variant

To assure that the humanized BAT-1.RH$_C$/Rκ$_D$ γ1 variant can recognize the same epitope as the original murine BAT-1, a competition assay of binding to Daudi cells that express the BAT-1-binding epitope was conducted.

Figure 21:
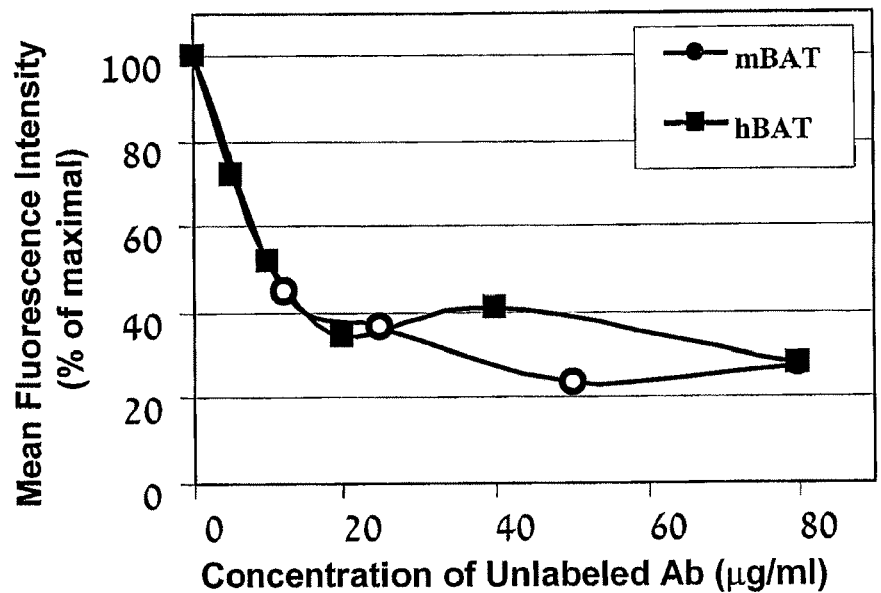
FIG. 21 presents dose dependence binding curves to Daudi cells of the murine BAT-1 mAb and the humanized BATRH$_C$/BATRκ$_D$ γ1 mAb.

Daudi cells were incubated with increasing amounts of the humanized BAT-1 or the mouse BAT-1 as control (0-80 μg/ml). Unbound antibody was discarded and biotinylated murine-BAT-1 (20 μg/ml) added to the cells and stained with streptavidin-FITC. FIG. 21 depicts a decreased binding of murine BAT-1 in the presence of increasing concentrations of both the humanized and original mouse mAb, supporting the recognition of the same epitope as expected. Both antibodies show a similar dose dependency, with an IC$_{50}$ of approximately 10 μg/ml, suggesting a similar affinity of antigen binding.

Example 21

In Vivo Effect of Humanized BAT-1 in a Murine Tumor Model

As shown in Example 20, CDR grafting resulting in the formation of the humanized BAT-1.RH$_C$/Rκ$_D$ γ1 mAb retained recognition of BAT-1 antigen. To examine whether this binding can transmit the biological effects characteristic of murine BAT-1, the efficacy of the humanized BAT-1 was studied in vivo. This is of particular importance in view of the isotype difference between the mouse and human mAbs.

Figure 22:
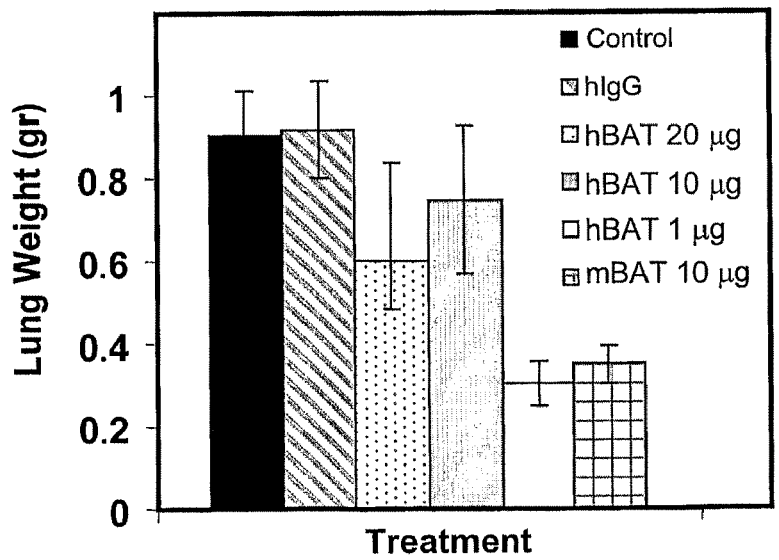
FIG. 22 illustrates the dose-dependent anti-metastatic activity of the humanized BATRH$_C$/BATRκ$_D$ γ1 mAb (hBAT) in murine B16 lung tumors, with respect to control (no treatment) and to treatment with the original murine BAT-1 mAb. All treatments were administered intravenously 14 days post tumor inoculation and lungs were examined 10 days post treatment.

C57BL mice were inoculated with B16 melanoma cells to induce lung metastases. Increasing amounts (1, 10 and 20 μg) of humanized mAb were injected on day 12 post tumor-inoculation and compared to an optimal dose of 10 μg murine-BAT-1. Lung weight measured on Day 24 post tumor inoculation is depicted in FIG. 22 and corresponds to the establishment of a tumor. Both non-treated mice and mice treated with an isotype-matched irrelevant human IgG1, had an average lung weight of 0.9 gr. The humanized BAT-1 exhibited a dose dependent inhibition of metastases growth with the highest inhibition occurring at a low dose of 1 μg/mouse. This resulted in a decrease of 67% in tumor mass and was similar to that achieved by an optimal dose of murine BAT-1 (62%). Importantly, this maximal effect was achieved by a ten-fold lower dose of the humanized mAb, suggesting a higher therapeutic efficacy of this antibody in comparison to the original murine BAT-1 mAb.

Example 22

Inhibition of Human Melanoma (SK-28) in SCID Mice by hBAT-1

Figure 23:
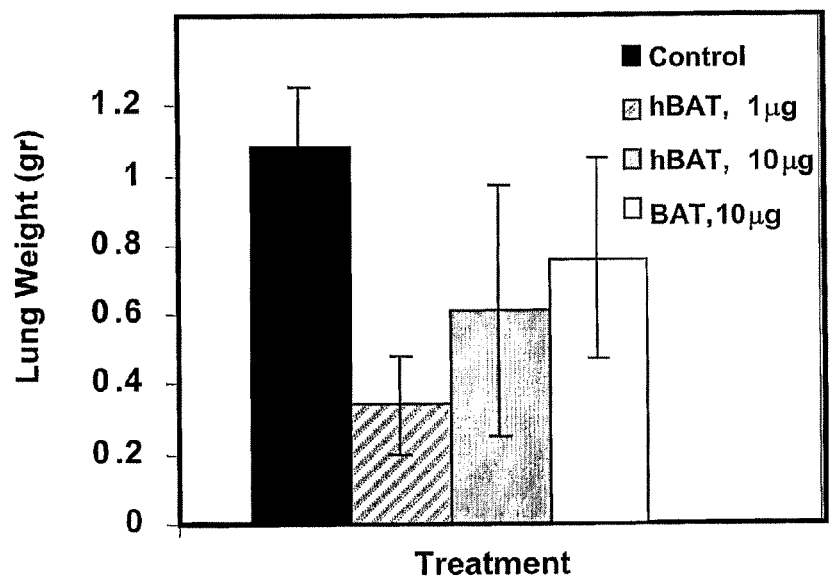
FIG. 23 represents the inhibitory effect of the humanized BATRH$_C$/BATRκ$_D$ γ1 mAb on human melanoma (SK-28) in SCID mice engrafted with human lymphocytes. The effect of the humanized BAT-1 on tumor growth is compared with control (no treatment) or treatment with the murine BAT-1 mAb (mBAT-1).

Mouse-BAT-1 mAb has been shown to inhibit the formation of human-tumor metastases in the presence of human peripheral blood lymphocytes (hPBL). To estimate the efficacy of humanized BAT-1.RH$_C$/Rκ$_D$ γ1 mAb in inhibition of human cancer, the humanized antibody was studied in a model combining both tumors and lymphocytes of human origin. Severe combined immune-deficient mice (SCID) were engrafted with hPBL to restore immune-competence. Mice were challenged with human melanoma cells (SK-28) and treated with increasing concentrations of the humanized antibody, administered in a single i.v. dose on day 11 post tumor inoculation. FIG. 23 depicts lung weight that correlates with the number of metastases observed, as measured on day 23. Both concentrations of the humanized antibody induced tumor inhibition in the presence of hPBL. As observed in the mouse tumor model described above, the humanized antibody could more efficiently inhibit tumor growth in vivo, in comparison to mouse BAT-1. A single dose of 1 μg of this humanized antibody inhibited tumor growth by 68% showing a higher efficacy than 10 μg of the mouse BAT-1 antibody (30%).

Example 23

Immunotherapy of Human Colorectal Cancer Hepatic Metastases by hBAT-1 Monoclonal Antibody in Nude Mice LIM6 and HM7 are two sub-clones of the human CRC cell line LS174T that were selected for their high mucin synthesis and metastatic potential. The tumor cells were injected into the exposed spleen of anesthetized nude mice. After 1 minute, the spleens were removed and the excisions closed. Low doses of murine and humanized BAT-1 antibody were administered 12 days later and mice were sacrificed 35 days post tumor inoculation. The livers were weighed, the number of metastatic nodules was counted, and liver tissue was processed for histology and Immunohistochemistry study.

Figure 24:
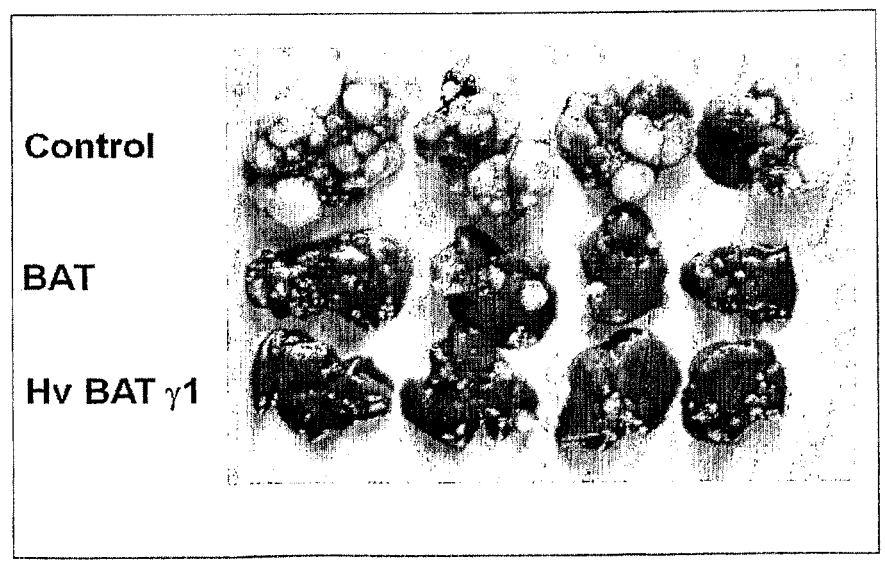
FIG. 24 demonstrates the anti-metastatic activity of the humanized BATRH$_C$/BATRκ$_D$ γ1 mAb in a Murine Tumor Model (HM7) implanted in BALB/c nude mice.

Treatment with BAT-1, murine and humanized antibodies, was found efficient in inhibition of liver metastases establishment in the murine model. Mouse BAT-1 antibody treatment prevented LIM-6 xenografts development. The average weight of xenografts from BAT-1 treated mice and controls were of 0.14±0.17 gr and 0.98±1.12 gr, respectively (P=0.004). HM7 cells injected to the nude mice resulted in large number of bulky metastatic lesions in the liver that were prevented by the single administration of murine BAT-1 and humanized BAT-1 (FIG. 24). A major (over 40%) decrease was observed in the number of metastatic nodules, namely from 134.5±34 in the control mice to 8.36±3 and 4.88±2 in mice treated with murine BAT-1 humanized BAT-1, respectively. Treatment with BAT-1 prevented the accumulation of lymphocytes in the tumor edge. The role of lymphocyte infiltration around the metastatic nodule may be related to outcome of the cancer and may suggest a mechanism for BAT-1 therapy.

Example 24

Co-localization of hBAT with CD4 and CD8

Mouse BAT-1 has been shown to bind human lymphocytes, recognizing both CD4+ and CD8+ subsets. To establish the binding specificity of the humanized BATRH$_C$/BATRκ$_D$ γ1 mAb (hBAT), human Peripheral Blood Lymphocytes (PBL) were isolated from the blood of normal donors, as described hereinbelow, and analyzed for co-localization of hBAT with known lymphocyte markers.

Peripheral blood mononuclear cells (PBMC) were isolated by ficoll and incubated in tissue culture plates to remove adherent cells. Isolated PBL were gated on lymphocytes by size and granularity and on live cells by propidium iodine (PI) exclusion. Binding was performed at 4° C. for 1 hr, and determined by flow cytometry on gated lymphocytes.

Figure 25:
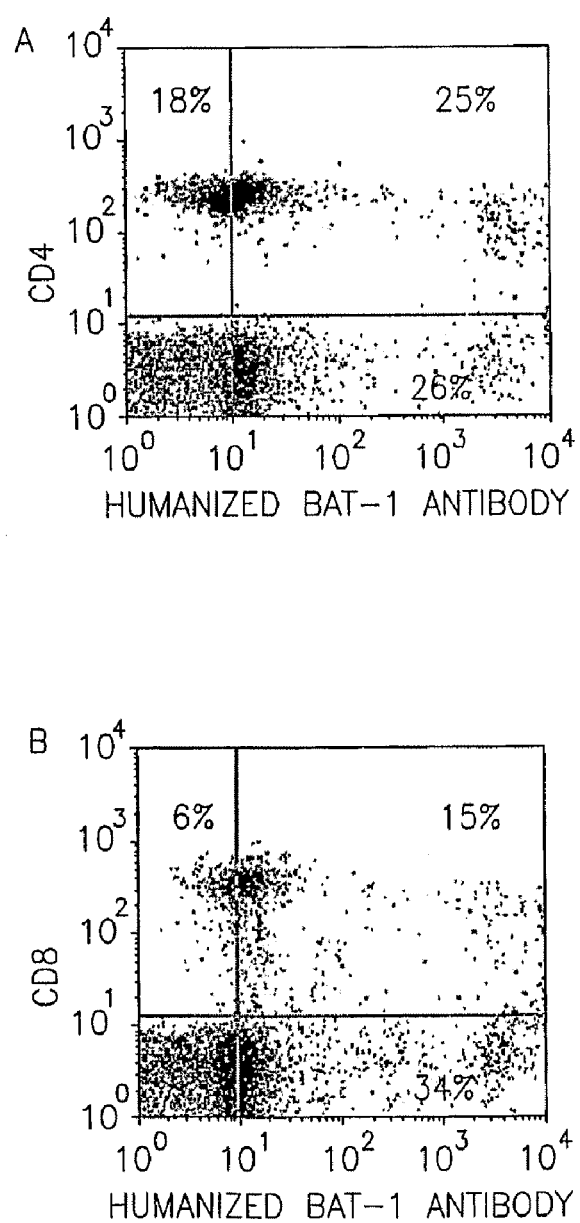
FIG. 25 shows co-localization of the humanized BATRH$_C$/BATRκ$_D$ γ1 mAb (hBAT) with CD4 (A) and CD8 (B) determined by flow cytometry on gated lymphocytes.

In all samples examined at least 20% of PBL exhibited binding to hBAT. FIG. 25 depicts an example of binding to lymphocytes of a selected donor in which 50% of the isolated PBL were positive for hBAT, including both CD4+ cells (25%) and CD8+ cells (15%). Within these subpopulations, the majority of CD4+ as well as CD8+ cells bound the hBAT mAb (58% and 71% respectively).

Example 25

Binding of HBAT to B Lymphocytes

The humanized BATRH$_C$/BATRκ$_D$ γ1 mAb (hBAT) was raised against the membranes of Daudi cells, a human B lymphoma cell-line. PBL from normal donors were isolated by ficoll, as described above, followed by adherence to tissue culture plates. Non-adherent cells were examined for the co-localization of hBAT with B-cell markers including CD19 and CD20. Binding was performed at 4° C. for 1 hr, and determined by flow cytometry on gated lymphocytes. FIG. 26 depicts the evaluation of binding to the cells of a representative normal donor.

25-29% of lymphocytes in the sample were positive for the humanized BAT mAb. These cells included the majority of B cells (70-75%) as demonstrated by both independent markers. 70% of CD20+ were positive for the humanized BAT mAb (Gated on R1 and PI negative; FIG. 26A) and 75% of CD19+ were positive for the humanized BAT mAb (Gated on R1 and PI negative). The results suggest that the BAT-binding moiety on the cell surface could be common to peripheral B cells.

Example 26

Binding of hBAT to CD4+ T Cells Increases Upon Activation of the Cells

Binding of the mouse BAT antibody has been formerly correlated with lymphocyte activation. This binding activity was further studied for the human mAb and the binding level of the human BAT mAB to human CD4+ T cells, subjected to activation, was examined. Cells were isolated from a normal donor by negative selection and stimulated with beads conjugated to anti-CD3 and anti-CD28 (5 μl/ml). This treatment was selected in order to exert polyclonal activation through the T-cell receptor and co-stimulatory molecules.

Cells were examined for binding of the humanized BATRH$_C$/BATRκ$_D$ γ1 mAb (hBAT) and anti-CD4 (4° C., 1 hr) on day 0, 2 and 5 following activation (FIGS. 27A, B and D). Analysis was performed by flow cytometry on cells negative for PI staining. Quadrants were determined by isotype controls.

Figure 27:
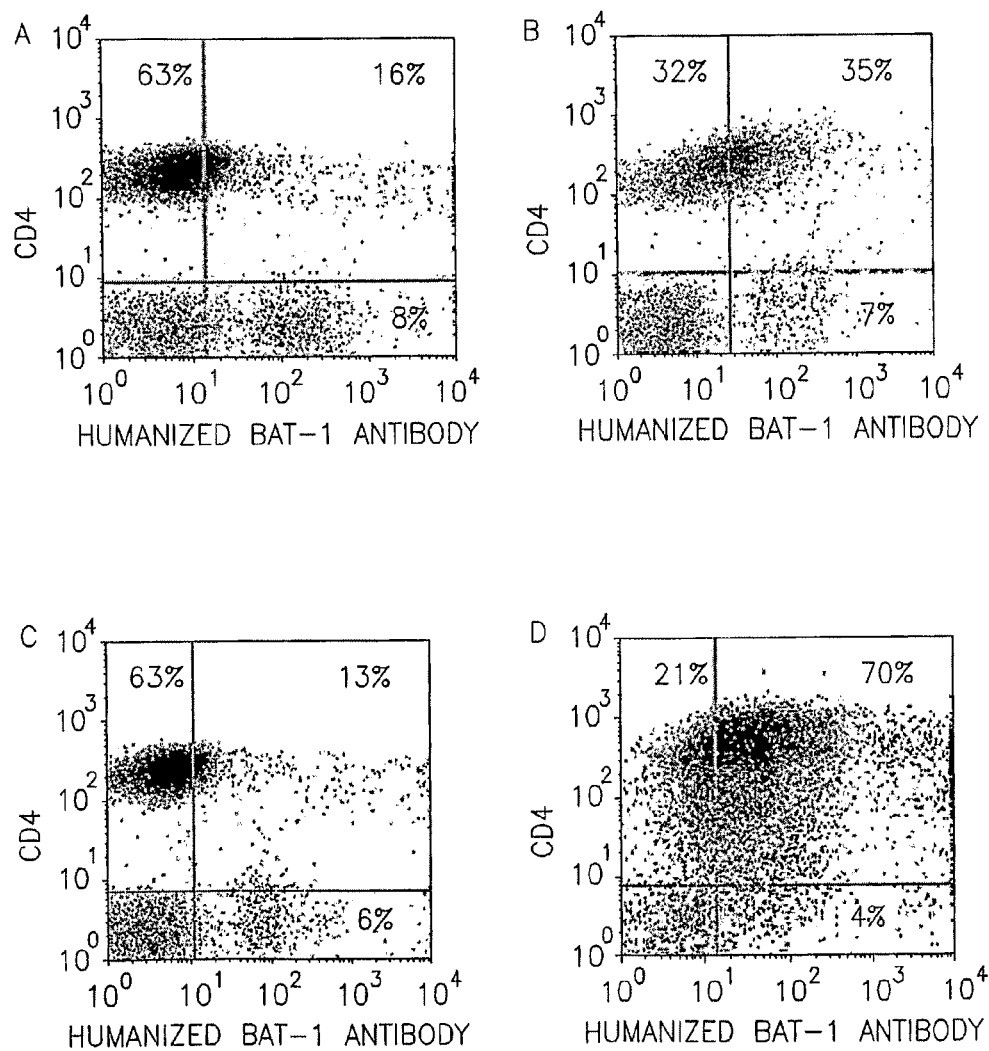
FIG. 27 represents the binding of the humanized BAT mAb to non-activated (day 0, A; day 5, C) and activated (2 days, B; 5 days, D) CD4+ T cells.

The binding of the humanized BATRH$_C$/BATRκ$_D$ γ1 mAb to CD4+ cells increased dramatically following activation (FIG. 27). Whereas non-activated cells, at day 0 (FIG. 27A) and at day 5 (FIG. 27C), exhibited 17-20% positive binding to hBAT, 52% and 77% of CD4+ cells bound hBAT on day 2 (FIG. 27B) and day 5 (FIG. 27D) of activation, respectively. Similar results were obtained with multiple samples and could also be demonstrated for CD8+ cells. This demonstrates that hBAT binding to T cells is increased upon TCR activation.

The dose dependency of this activation was demonstrated by co-localization of hBAT with CD69. T cell activation is characterized by cell-surface expression of various molecules, some of which have been shown to be involved in the activation process. hBAT was studied for its co-expression with different markers including both early and late activation molecules. CD69, an early activation marker, is up-regulated on T cells upon activation. Four days following activation, cells were examined for binding of hBAT and anti-CD69 (4° C., 1 hr). Analysis was performed by flow cytometry on cells negative for PI staining. Quadrants were determined by isotype controls.

Figure 28:
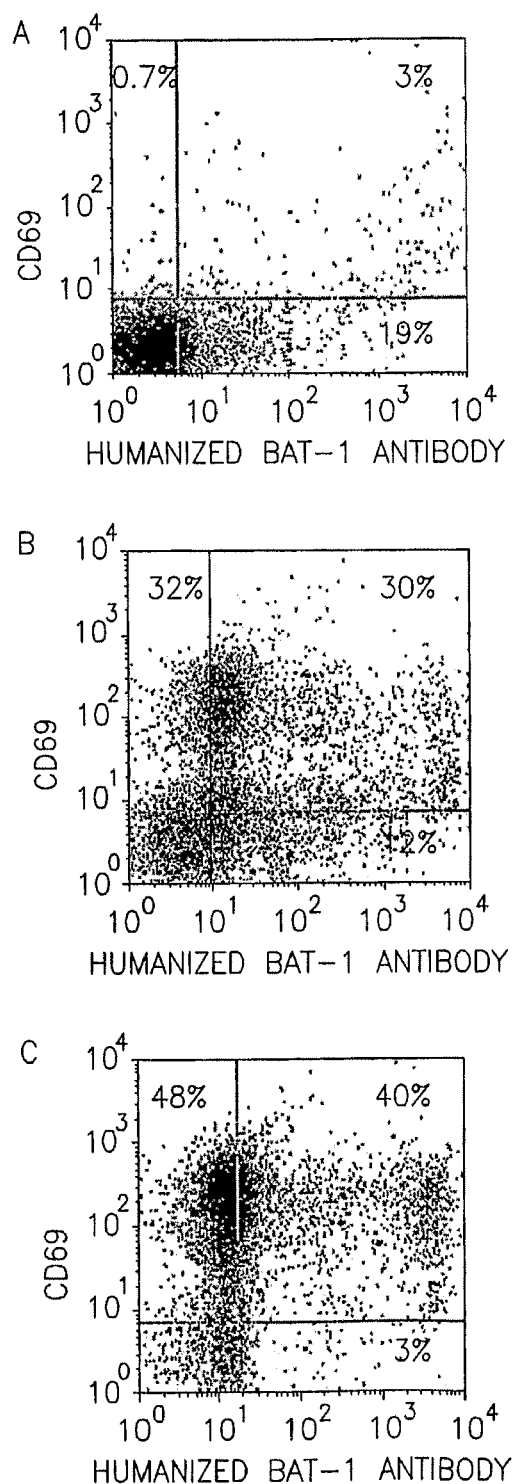
FIG. 28 shows the binding of the humanized BAT mAb to CD69+ T cells activated with beads conjugated to anti-CD3 and anti-CD28 in a dose-dependent manner (no activation, A; 0.25 μl, B; 0.5 μl, C).

A dose-dependent activation of CD4+ T cells from a normal donor is demonstrated in FIG. 28. Upon strong activation (5 μl/ml of beads conjugated to anti-CD3 and anti-CD28; FIG. 28B) most of the cells, which were capable of binding to hBAT (93%), were activated cells and were identified by CD69 expression. Increased time of activation also resulted in increase binding to hBAT beginning at day one of activation. Time dependency of activation could also be demonstrated and resulted in an increase in hBAT binding beginning at day one of activation. Interestingly, hBAT binding to both CD4+ and CD8+ cells remained high even after CD69 decrease (day 5) suggesting a correlation of binding with multiple stages of lymphocyte activation. hBAT binding to CD69+ cells suggests that the expression of hBAT binding protein is correlated with early activation.

Example 27

Binding of HBAT to Activated T Cells Expressing CD25 and CD40-Ligand

CD25, the high-affinity receptor for IL2, is vital for T-cell expansion and is typically increased on the surface of activated cells. Chronologically it follows the appearance of CD69 and its expression is extended several days after the down-regulation of CD69.

CD4+ T cells were isolated from a normal donor by negative selection and stimulated for several days with beads conjugated to anti-CD3 and anti-CD28 (5 µl/ml). Cells were examined for binding of hBAT and anti-CD25 (4° C., 1 hr) on day 0 (FIG. 29A), day 1 (FIG. 29B), and day 5 (FIG. 29D) of activation with respect to controls (day 0, FIG. 29A and day 5 of no activation, FIG. 29C). Analysis was performed by flow cytometry on cells negative for PI staining. Quadrants were determined by isotype controls.

Figure 29:
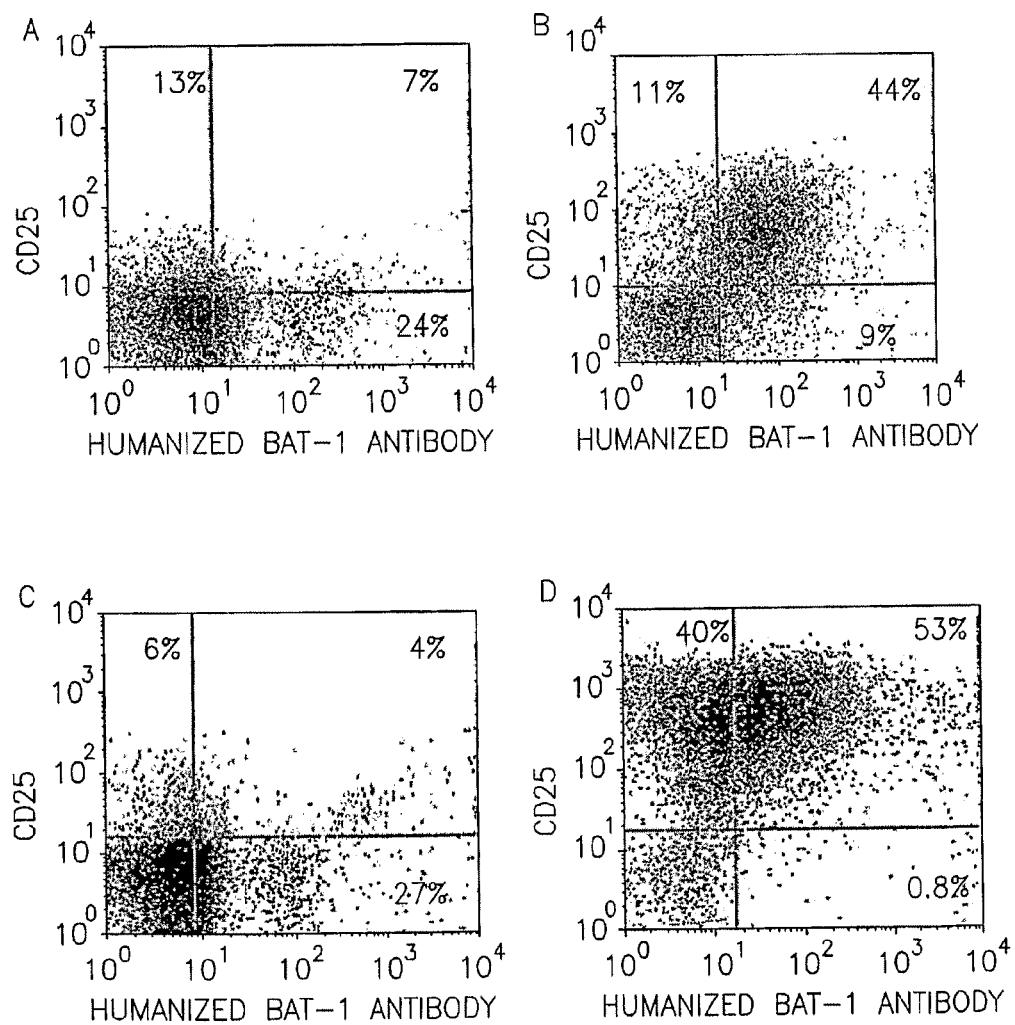
FIG. 29 presents co-localization of the humanized BATRH$_C$/BATRκ$_D$ γ1 mAb with CD25 marker of T cells in a time dependent manner: day 0, A; day 2 and day 5 of activation, B and D respectively; day 5 of no activation, C.

Both CD4+ and CD8+ T cells showed a time dependent increase in CD25 expression upon anti-CD3 and anti-CD28 stimulation, beginning at day 1 of stimulation. hBAT co-localized with CD25 on these activated cells (FIG. 29).

CD25 expression increased from 55% of the cells on day 1 (FIG. 29B) to 93% on day 5 (FIG. 29D) following activation. At both time points the majority of hBAT binding cells were CD25+ (85% and 98% respectively).

Figure 30:
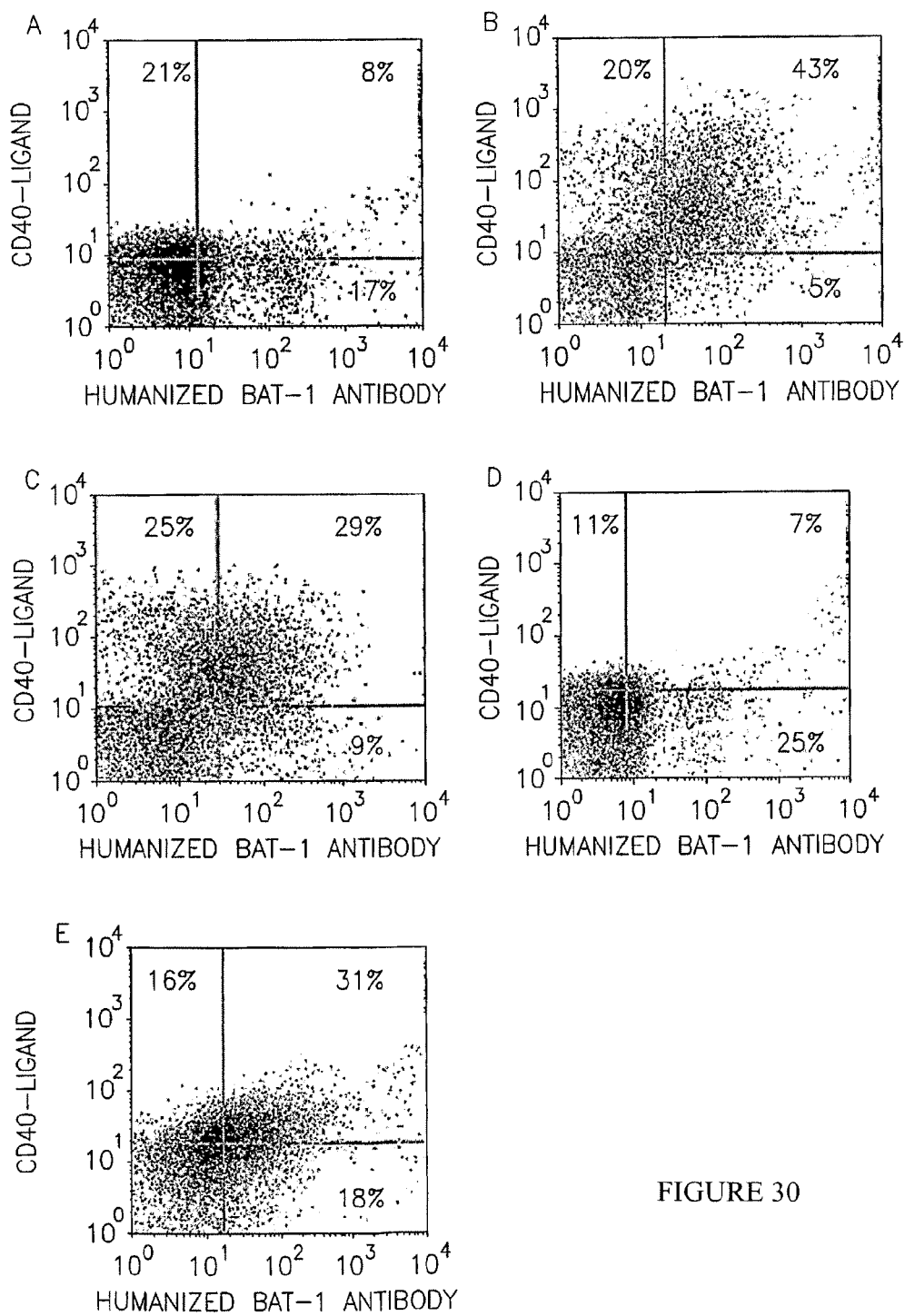
FIG. 30 shows co-localization of the humanized BATRH$_C$/BATRκ$_D$ γ1 mAb with CD40-Ligand marker of T cells in a time dependent manner: day 0, A; day 1, day 2 and day 5 of activation, B-C and E, respectively; day 5 of no activation, D.

Correlation with activation markers was further extended to the late activation marker CD40-Ligand (FIG. 30). hBAT binding positively correlated with the expression of CD40-Ligand in CD4+ (FIG. 30) and CD8+ T cells in a time dependent manner. The results culminate to suggest that activation of T cells induces the expression of the hBAT binding protein in a manner that correlates with different activation stages.

Example 28 hBAT Increases Survival of activated CD4+ Cells

To examine whether activated T cells can be further stimulated by the hBAT, human CD4+ cells were isolated from normal donors by negative selection and activated with a suboptimal concentration (0.25 µl/ml) of anti-CD3/CD28 beads (FIG. 31). hBAT (0.5 µg/ml) was added 2 days following activation and its effect was evaluated by determining the number of viable cells. The results indicate that hBAT induced a significant increase in the number of viable CD4+ cells isolated from the two separate donors (FIGS. 31A and B). Control nonstimulated cells died within eight days of isolation whereas activated cells expanded in a manner that is typical of lymphocytes, commencing with cell proliferation followed by a stage of stable cell number leading to a stage dominated by cell death. The addition of hBAT enhanced the expansion of CD4+ cell and increased the number of cells by 1.5 folds with respect to cells in the absence of the mAb.

The fact that the efficacy of BAT antibody in vivo is increased in the presence of tumor together with the results herein, suggests that the increased efficacy may depend on the presence of activated BAT target cells. Lymphocytes directed against tumor antigens have been observed in cancer patients, albeit inefficient in the inhibition of tumor growth, and may serve as target cells for BAT activity. Thus, in view of the results it may be implied that hBAT activates CD4+ cells by stimulating cell proliferation and/or by inhibiting cell death.

Example 29

Binding of HBAT to Daudi and Jurkat Cell Lines

Mouse BAT-1 was raised against membranes of the Daudi B-cell line and has been shown to bind human T cells. To verify the specificity of the humanized antibody, hBAT was examined for its binding to two human cell lines of myeloid origin: Daudi cells—a human B cell lymphoma line and Jurkat cells—a human T cell leukemia line. hBAT conjugated to FITC was incubated with Daudi and Jurkat cells at a concentration of 150 ug/ml (4° C. for 1 hr). Binding was determined by flow cytometry.

Figure 32:
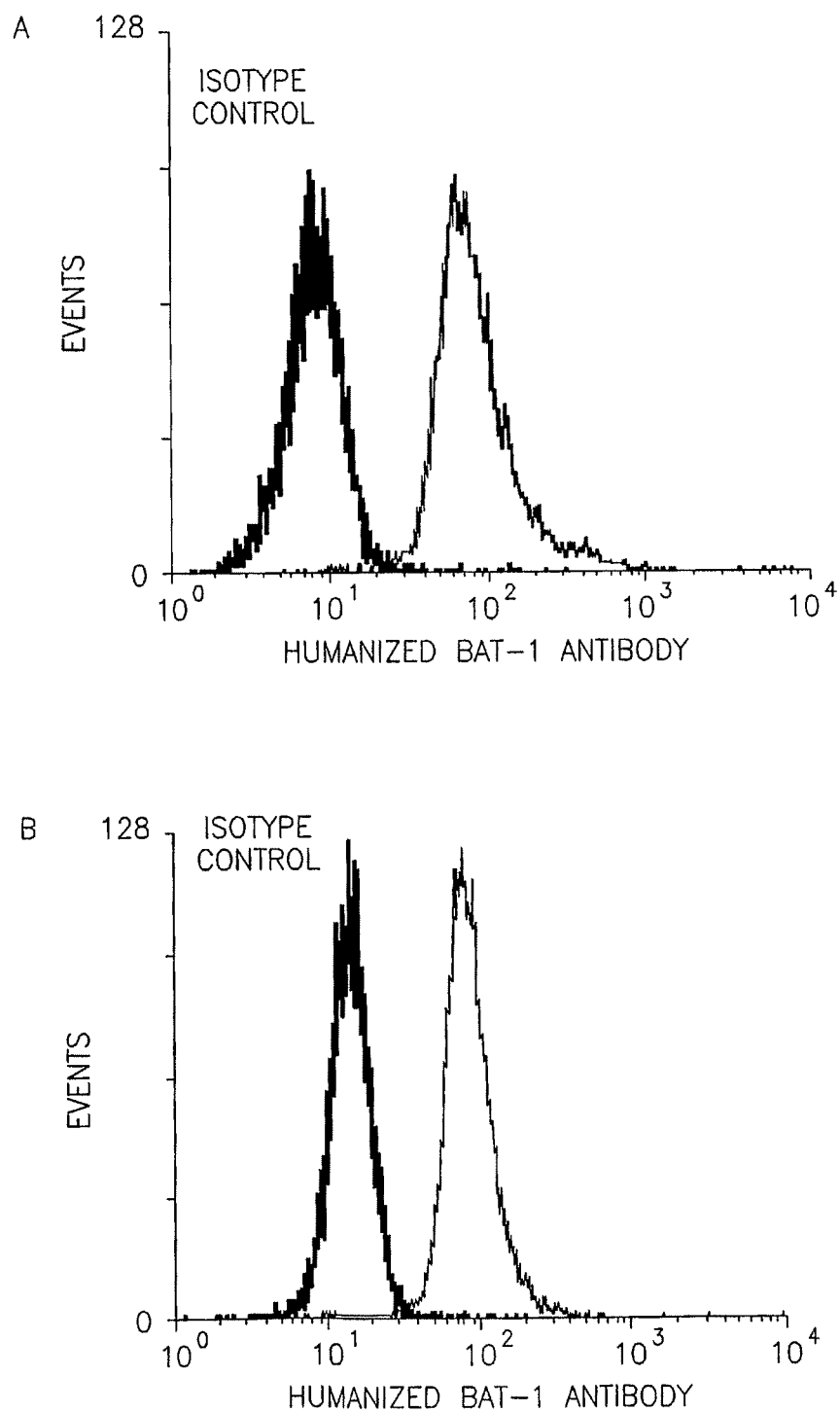
FIG. 32 presents hBAT binding to Daudi (A) and Jurkat (B) cell lines.

Both cell lines, Daudi (FIG. 32A) and Jurkat (FIG. 32B) bound the humanized antibody. Moreover, most of the cells in culture of both lines were capable of binding the antibody. An isotype matched human-IgG1 served as a negative control (FIG. 32; isotype control) and established the reading threshold. Both cell lines demonstrated a similar intensity of antibody staining suggesting that they express a similar number of hBAT binding molecules.

Example 30

Binding of HBAT to PBL of Cancer Patients

Figure 33:
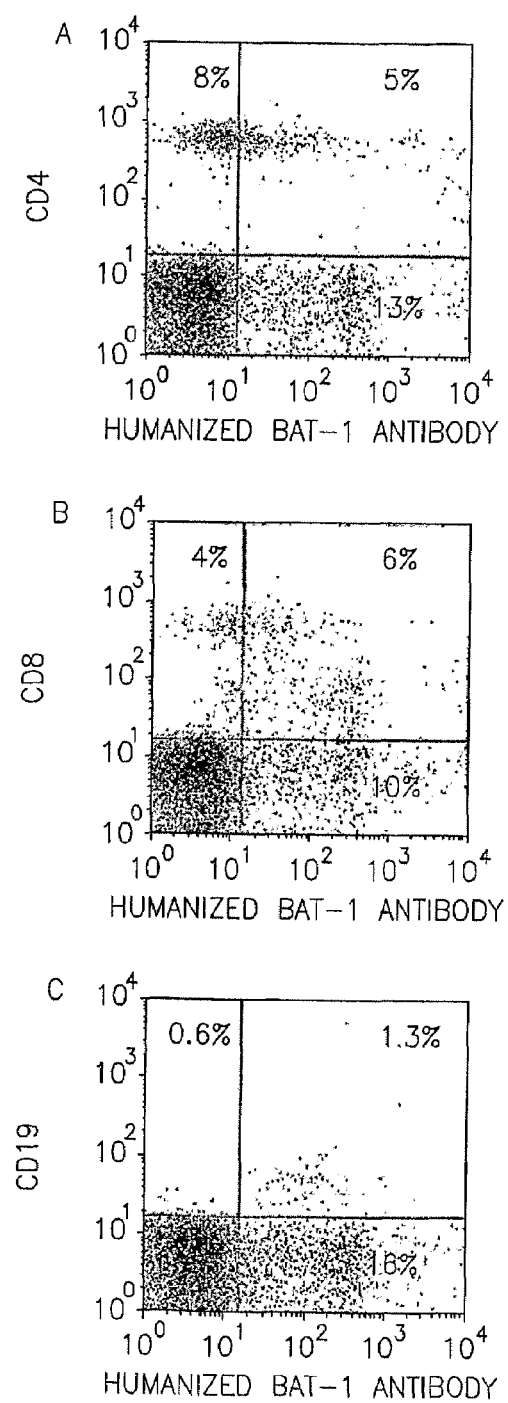
FIG. 33 demonstrates hBAT binding to peripheral blood lymphocytes, namely CD4+ cells (A), CD8+ cells (B) and B cells (C), of cancer patients.

Following the observation that hBAT is capable of binding human T cells from normal donors, we compared its ability to bind lymphocytes collected from cancer patients. PBL were isolated from the blood of a prostate cancer patient by ficoll followed by adherence to tissue culture plates. Non-adherent cells were examined for binding of hBAT and lymphocyte markers. Binding was performed at 4° C. for 1 hr, and determined by flow cytometry on gated lymphocytes. Isotype controls were used to determine the quadrants. These patients have formerly undergone therapy that often affects the presence and phenotype of lymphocytes. hBAT binding to these cells is a pre-requisite for its activity and as depicted in FIG. 33, resembles the binding to lymphocytes of normal donors. Although total lymphocyte numbers were low, hBAT could still bind a large proportion of the lymphocyte subpopulations which we examined including 39% of CD4+ cells, 60% of CD8+ cells and 68% of B cells.

Example 31

Cross Reactivity of HBAT with Human, Primate and Murine Tissues

The purpose of this study was to examine the cross reactivity of hBAT-1 monoclonal antibody with a range of normal human tissue. This study involved immunohistochemical testing of the monoclonal antibody against a range of human tissues. A comparison of in vitro cross-reactivity in tissues from cynomologus monkey and CD-1 mice was also undertaken.

(i) Tissue Source

The tissues used in this study were each obtained from three unrelated donors to minimize the chances of donor specific factors affecting antibody binding. The human tissue was provided by an ethical source. The primate and murine tissues used in this study were obtained from two animals of each species, by an ethical source. The murine and primate are potential test systems that may be evaluated in pre-clinical toxicology Studies. The tissues selected were those specified in the FDA Points to Consider in the Manufacture and Testing of Monoclonal Antibody Products for Human Use (Office of Biologics Research and Review. Center for Biologics Evaluation and Research FDA. 1997) and the Rules Governing Medicinal Products in the European Community Vol. 3a (Production and Quality Control of Monoclonal Antibodies Dec. 1994, 3AB4a). All tissues used in this investigation were snap frozen in liquid nitrogen and stored at or below −70° C. until required. Cryostat sections were prepared at a nominal thickness of 5 μm to 8 μm. The positive control was Jurkat E6 cells. Samples of fresh blood were collected from 3 donors and smears prepared on the day of use.

(ii) FITC Conjugation

The humanized monoclonal hBAT-1 antibody was conjugated to FITC by the Custom Antibody Services Division of Serotec Ltd (ISO 9001, Certification) before the study was started. The final concentration of the conjugated antibody was 1.99 mg/ml.

Initial validation of the methodology was performed on control tissue (Jurkat E6 cell line) to determine the titer concentration for antibody-tissue binding with frozen sections and other conditions relevant to the proper performance of the antibody-tissue binding. Slides were microscopically examined and scored subjectively against the antibody specificity (Table 21). Based on these data, the concentrations of hBAT-1 that were used throughout the study were 1:100, 1:250 and 1:500.

TABLE 21

| hBAT-1 dilution | [1]Specificity | Signal Strength | Background |
|---|---|---|---|
| 1:25 | 3 | +++ | 3 |
| 1:50 | 3 | +++ | 2 |
| 1:100 | 3 | +++ | 1 |
| 1:250 | 3 | +++ | 0 |
| 1:500 | 2 | ++ | 0 |
| 1:1000 | 1 | + | 0 |
| 1:2000 | 0 | 0 | 0 |
| 1:4000 | 0 | 0 | 0 |
| 1:8000 | 0 | 0 | 0 |
| Negative | 0 | 0 | 0 |

[1]Key: 3 refers to strong positive-staining, 2 refers to positive staining, 1 refers to weak positive staining and 0 refers to no staining/signal. +++ refers to strong visual signal, ++ refers to good visual signal and + refers to weak visual signal.

(iii) Controls.

Negative control reactions, in which the antibody was substituted with a buffer, were carried out for each tissue. Each detection reaction included positive control cells, Jurkat E6, reacted at the three predetermined dilutions of the antibody. This allowed the consistency of the reaction to be monitored. Sections of thyroid, incubated with anti actin antibody, were included in each assay run as controls for the detection system.

(iv) Cross-reactivity Assessment

Sections of each tissue were stained with Haematoxylin and Eosin (H&E) to confirm their identity and suitability for the study. Sections were also incubated with anti smooth muscle actin (SMA; Table 22) or rabbit anti human transferrin control sera, which showed the tissues were suitable for immunohistochemistry. Three sections of each of the tissues were prepared and incubated with the antibody, which had been conjugated to FITC, at concentrations of 1:100, 1:250 and 1:500 as determined during the validation phase. After washing in buffer and blocking with normal serum, the sections were incubated with the appropriate secondary and tertiary antibodies for alkaline-phosphatase detection, and counter-stained with haematoxylin before microscopical examination to determine sites of binding.

The FITC-conjugated staining method with Alkaline Phosphatase detection contained the following steps:

1. Air dry cryostat sections.
2. Fix by immersion in acetone, 10 minutes at room temperature
3. Air dry.
4. Buffer wash.
5. Normal serum, 1:5, at least 20 minutes.
6. Buffer wash
7. 1022292 test FITC conjugated antibody at 1:100, 1:250 and 1:500,:. overnight at 2-8° C.
8. Buffer wash.
9. Monoclonal anti FITC antibody, 1:50, 30 minutes.
10. Buffer wash.
11. Alkaline phosphatase conjugated antibody, 1:200, 2 hours.
12. Buffer wash.
13. Vector red and levamisole, 20 minutes.
14. Buffer wash.
15. Counterstain and mount.

Endogenous alkaline phosphatase was minimized by using Levamisole incorporated into the chromogen. In tissues where endogenous alkaline phosphatase activity could not be suppressed (human colon, ileum, placenta and endothelium, murine colon and pancreas, primate stomach, ileum and prostate), horseradish peroxidase conjugated antibody at 1:200 for 2 hours was used, followed by Diaminobenzidene (DAB) reagent for 20 minutes.

(v) Results

Samples of individual tissues stained with H&E were examined for quality of tissue, presence of normal histological features and adequacy of preservation. All samples that were tested were considered to be suitable for the purposes of this study. Positive staining was achieved in the Jurkat E6 cell line for hBAT-1 and in the thyroid sections treated with smooth muscle actin. As the controls gave the expected results, the test was considered valid.

Individual cross reactivity results for hBAT-1 and human tissues are shown in Tables 22. Positive staining was detected in blood vessels human endothelium at a dilution of 1:100 and was probably a result of hBAT-1 binding to lymphocytes. Positive staining indicates probable tissue binding of the humanized monoclonal hBAT-1 antibody. No staining, i.e. cross reactivity with hBAT-1, was observed in spleen sections, blood smears or other human tissues (except human endothelium-blood vessels). None of the murine and primate tissues showed evidence of cross reactivity with hBAT-1.

TABLE 22

| Tissue | SMA | hBAT-1 Antibody | | | |
|---|---|---|---|---|---|
| | | 1:100 | 1:250 | 1:500 | 1:100 |
| Adrenal | + | − | − | − | − |
| Bladder | + | − | − | − | − |
| Blood Cells | [1]N/A | − | − | − | − |
| Blood Vessel (endothelium) | + | + | − | − | − |
| Bone Marrow | N/A | − | − | − | − |
| Breast | + | − | − | − | − |
| Cerebellum | + | − | − | | |
| Cerebral Cortex | + | − | − | − | − |
| Colon | + | − | − | − | − |
| Eye (Retina) | + | − | − | − | − |
| Fallopian tube | + | − | − | − | − |
| Heart | + | − | − | − | − |
| Ileum (GI tract) | + | − | − | − | − |
| Kidney | + | − | − | − | − |
| Liver | + | − | − | − | − |
| Lung | + | − | − | − | − |
| Lymph node | + | − | − | − | − |
| Ovary | + | − | − | − | − |
| Pancreas | + | − | − | − | − |
| Parathyroid | + | − | − | − | − |
| Parotid | + | − | − | − | − |
| Pituitary | + | − | − | − | − |
| Placenta | + | − | − | − | − |
| Prostate | + | − | − | − | − |
| Skin | + | − | − | − | − |
| Spinal cord | + | − | − | − | − |
| Spleen | + | − | − | − | − |
| Stomach | + | − | − | − | − |
| Striated muscle | + | − | − | − | − |
| Testes | + | − | − | − | − |
| Thymus | + | − | − | − | − |
| Thyroid | + | − | − | − | − |
| Tonsil | + | − | − | − | − |
| Ureter | + | − | − | − | − |
| Uterus-cervix | + | − | − | − | − |
| Uterus-endometrium | + | − | − | − | − |

[1]N/A - result not applicable

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

What is claimed is:

1. A humanized antibody comprising the complementarity-determining regions (CDRs) of murine monoclonal antibody BAT-1 (mBAT-1), wherein the humanized antibody comprises:
 a light chain variable region selected from the group consisting of: BATRKA (SEQ. ID NO. 15), BATRKB (SEQ. ID NO. 16), BATRKC (SEQ. ID NO. 17), and BATRKD (SEQ. ID NO. 18), and
 a heavy chain variable region selected from the group consisting of: BATRHA (SEQ. ID NO. 20), BATRHB (SEQ. ID NO. 21), BATRHC (SEQ. ID NO. 22), BATRHD (SEQ. ID NO. 23) and BATRHE (SEQ. ID NO. 24); wherein the humanized antibody retains the anti-tumor activity of mBAT-1 and is less immunogenic in a human subject than mBAT-1.

2. The humanized antibody of claim 1, wherein the variable regions are selected from the group consisting of: BATRHA/BATRKA (SEQ. ID NO. 20/SEQ. ID NO. 15), BATRHB/BATRKA (SEQ. ID NO. 21/SEQ. ID NO. 15), BATRHB/BATRKB (SEQ. ID NO. 21/SEQ. ID NO. 16), BATRHC/BATRKB (SEQ. ID NO. 22/SEQ. ID NO. 16), BATRHB/BATRKD (SEQ. ID NO. 21/SEQ. ID NO. 18), and BATRHC/BATRKD (SEQ. ID NO. 22/SEQ. ID NO. 18).

3. An antibody fragment of the humanized antibody of claim 1, wherein the antibody fragment is selected from the group consisting of: Fv, F(ab'), F(ab')2, and a single chain antibody.

4. A pharmaceutical composition comprising the humanized antibody according to claim 1, and a physiologically acceptable carrier, diluent, or stabilizer.

5. A method for treating cancer cells that express the BAT-1 antigen in a subject in need of such treatment which comprises the step of treating the subject with a therapeutically effective amount of a pharmaceutical composition containing as an active ingredient the humarized antibody of claim 1 and optionally including a physiologically acceptable carrier, diluent, or stabilizer.

6. The method of claim 5 further comprising treating the subject with an additional therapeutic agent.

7. The method of claim 6 wherein the additional therapeutic agent is selected from IL-1, IL-2, IL-6, IFN-α (interferon-α), T-cell stimulatory antibody, or anti-tumor therapeutic antibody.

8. The method of claim 6, wherein the humanized antibody and the additional agent is administered substantially at the same time in a single composition or sequentially in separate compositions.

9. The method of claim 6, further comprising applying a cell therapy treatment to the subject.

10. The method of claim 9, wherein the cells are autologous or allogeneic cells.

11. The method of claim 6 wherein the cancer is selected from the group consisting of melanoma, a lung tumor, colorectal cancer and hepatic metastasis.

12. A method for producing the humanized antibody of claim 1, which comprises:
 a) transfecting a host cell with a vector comprising a polynucleotide sequence encoding the humanized antibody, or co-transfecting the host cell with 2 vectors each comprising a polynucleotide sequence encoding the heavy or light chain regions of the humanized antibody;
 b) culturing the host cell so that said humanized antibody is expressed; and
 c) recovering the humanized antibody from the host cell culture.

* * * * *

UNITED STATES PATENT AND TRADEMARK OFFICE
CERTIFICATE OF CORRECTION

PATENT NO. : 7,332,582 B2
APPLICATION NO. : 10/994091
DATED : February 19, 2008
INVENTOR(S) : Hardy et al.

It is certified that error appears in the above-identified patent and that said Letters Patent is hereby corrected as shown below:

Drawings:
Delete Drawing Sheets 5 and 6, and replace with Drawing Sheets 5 and 6. (Attached)

Column 8:
Line 1, change "ENGHTSRAOHAD" to -- ENGHTSRAQHAD --.
Line 17, change "HENOSYT" to -- HENQSYT --.
Line 21, change "REWYGOVLNKA" to -- REWYGQVLNKA --.

Column 57:
Line 59, change "$RH_c/RK_D$" to -- $RH_c/R\kappa_D$ --.

Signed and Sealed this

Second Day of December, 2008

JON W. DUDAS
*Director of the United States Patent and Trademark Office*

```
CDRs Kabat NO                          ===L1====                             ===L2===
           SEQ ID NO.
                           1         2         3         4         5         6         7
                   1234567890123456789012345678901234567890123456789012345678901234567890
Mouse BATVk    129 QIVLTQSPAIMSASPGEKVTITCSARSSVSYMHWFQQKPGTSPKLWIYRTSNLASGVPARFSGSGSGTSY
Human TEL9Vk   130 E......SSL...V.DR.....R.SQSISN.LN.Y....KA...L..AA.T.Q....S.......D
Variants
BATRKA          15 EIVLTQSPSSLSASVGDRVTITCSARS-SVSYMHWYQQKPGKAPKLLIYRTSNLASGVPSRFSGSGSGTD
BATRKB          16 EIVLTQSPSSLSASVGDRVTITCSARS-SVSYMHWFQQKPGKAPKLWIYRTSNLASGVPSRFSGSGSGTD
BATRKC          17 EIVLTQSPSSLSASVGDRVTITCSARS-SVSYMHWFQQKPGKAPKLWIYRTSNLASGVPSRFSGSGSGTD
BATRKD          18 EIVLTQSPSSLSASVGDRVTITCSARS-SVSYMHWFQQKPGKAPKLWIYRTSNLASGVPSRFSGSGSGTS CDRs Kabat NO                 ===L3====
           SEQ ID NO
                           8         9        10
                   12345678901234567890123456789012345 67
Mouse BATVk    129 CLTISRMEAEDAATYYCQQRSSFPLTFGSGTKLEIK
Human TEL9V    130 FT...NSLQP..F......TN.......G........
Variants
BATRKA          15 FTLTINSLQPEDFATYYCQQRSSFPLTFGGGTKLEIK
BATRKB          16 YTLTINSLQPEDFATYYCQQRSSFPLTFGGGTKLEIK
BATRKC          17 YCLTINSLQPEDFATYYCQQRSSFPLTFGGGTKLEIK
BATRKD          18 YCLTINSLQPEDFATYYCQQRSSFPLTFGGGTKLEIK
```

FIGURE 5

```
CDRs Kabat Numbers                     ------=H1=                                    ==========H2==========
                          1               2         3         4         5         6         7
                 123456789012345678901234567890123456789012A345678901234567890123456
Mouse BATVH      QIQLVQSGPELKKPGETVKISCKASGYTFTNYGMNWVKQAPGKGLKWMGWINTDSGESTYAEEFKGRFAFSLETSAN
(SEQ ID NO:145)
hsighv 1295 VH   .V......S.......AS........S.SSHAI...R....Q...Q.......NT.SP...QG.T...V...D..VS
(SEQ ID NO:146)
Variant SEQ ID NO.
BATRHA    20     QVQLVQSGSELKKPGASVKISCKASGYSFSNYGMNWVRQAPGQGLQWMGWINTDSGESTYAEEFKGRFVFSLDTSVS
BATRHB    21     QVQLVQSGSELKKPGASVKISCKASGYTFTNYGMNWVRQAPGQGLQWMGWINTDSGESTYAEEFKGRFVFSLDTSVS
BATRHC    22     QVQLVQSGSELKKPGASVKISCKASGYTFTNYGMNWVRQAPGQGLQWMGWINTDSGESTYAEEFKGRFVFSLDTSVN
BATRHD    23     QIQLVQSGSELKKPGASVKISCKASGYTFTNYGMNWVRQAPGQGLKWMGWINTDSGESTYAEEFKGRFVFSLDTSVN
BATRHE    24     QIQLVQSGSELKKPGASVKISCKASGYTFTNYGMNWVRQAPGQGLKWMGWINTDSGESTYAEEFKGRFAFSLDTSVN CDRs Kabat Numbers                         ====H3====
                          8         9         10        11
                 789012ABC345678901234567890ABC123456789 0123
Mouse BATVH      TAYLQINNLNNEDTATYFCVRVGYDAL----DYWGQGTSVTVSS
(SEQ ID NO:145)
hsighv 1295 VH   ......TS..TA...GM...AKESHSSA LDL.......L......
(SEQ ID NO:146)
Variant SEQ ID NO.
BATRHA    20     TAYLQITSLTAEDTGMYFCAKVGYDAL----DYWGQGTLVTVSS
BATRHB    21     TAYLQITSLTAEDTGMYFCAKVGYDAL----DYWGQGTLVTVSS
BATRHC    22     TAYLQITSLTAEDTGMYFCVRVGYDAL----DYWGQGTLVTVSS
BATRHD    23     TAYLQITSLTAEDTGMYFCVRVGYDAL----DYWGQGTLVTVSS
BATRHE    24     TAYLQITSLNAEDTGMYFCVRVGYDAL----DYWGQGTLVTVSS
```

FIGURE 6

UNITED STATES PATENT AND TRADEMARK OFFICE
CERTIFICATE OF CORRECTION

PATENT NO.       : 7,332,582 B2
APPLICATION NO.  : 10/994091
DATED            : February 19, 2008
INVENTOR(S)      : Hardy et al.

It is certified that error appears in the above-identified patent and that said Letters Patent is hereby corrected as shown below:

Sequence listing:
Replace SEQ ID NO: 18 with the following sequence to change amino acid 69 from Aspartic acid (Asp) to Serine (Ser):

```
Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Phe Gln Gln Lys Pro Gly Lys Ala Pro Lys Leu Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Ser Tyr Cys Leu Thr Ile Asn Ser Leu Gln Pro Glu
65                  70                  75                  80

Asp Phe Ala Thr Tyr Tyr Cys Gln Gln Arg Ser Ser Phe Pro Leu Thr
                85                  90                  95

Phe Gly Gly Gly Thr Lys Leu Glu Ile Lys
        100                 105
```

Signed and Sealed this

Fifteenth Day of December, 2009

David J. Kappos
*Director of the United States Patent and Trademark Office*